US010047072B2

(12) United States Patent
Ashford et al.

(10) Patent No.: US 10,047,072 B2
(45) Date of Patent: Aug. 14, 2018

(54) THERAPEUTIC POLYMERIC NANOPARTICLES AND METHODS OF MAKING AND USING SAME

(71) Applicant: ASTRAZENECA AB, Sodertalje (SE)

(72) Inventors: Marianne Bernice Ashford, Macclesfield (GB); James Martin Nolan, III, Cambridge, MA (US); Eyoung Shin, Cambridge, MA (US); Young-Ho Song, Cambridge, MA (US); Greg Troiano, Cambridge, MA (US); Hong Wang, Cambridge, MA (US)

(73) Assignee: ASTRAZENECA AB, Sodertalje (SE)

( * ) Notice: Subject to any disclaimer, the term of this patent is extended or adjusted under 35 U.S.C. 154(b) by 0 days.

(21) Appl. No.: 14/485,875

(22) Filed: Sep. 15, 2014

(65) Prior Publication Data
US 2015/0140104 A1 May 21, 2015

Related U.S. Application Data

(60) Provisional application No. 61/878,227, filed on Sep. 16, 2013, provisional application No. 61/939,332, filed on Feb. 13, 2014.

(51) Int. Cl.
| | | |
|---|---|---|
| *A61K 9/16* | (2006.01) | |
| *C07D 403/12* | (2006.01) | |
| *A61K 47/12* | (2006.01) | |
| *A61K 9/51* | (2006.01) | |
| *A61K 31/675* | (2006.01) | |
| *A61K 45/06* | (2006.01) | |
| *A61K 31/517* | (2006.01) | |
| *A61K 9/00* | (2006.01) | |

(52) U.S. Cl.
CPC .......... *C07D 403/12* (2013.01); *A61K 9/0019* (2013.01); *A61K 9/16* (2013.01); *A61K 9/5123* (2013.01); *A61K 9/5153* (2013.01); *A61K 31/517* (2013.01); *A61K 31/675* (2013.01); *A61K 45/06* (2013.01); *A61K 47/12* (2013.01)

(58) Field of Classification Search
CPC ........ A61K 31/675; A61K 45/06; A61K 9/16; C07D 403/12
See application file for complete search history.

(56) References Cited

U.S. PATENT DOCUMENTS

| | | | |
|---|---|---|---|
| 5,480,883 A | 1/1996 | Spada et al. | |
| 5,543,158 A | 8/1996 | Gref et al. | |
| 5,578,325 A | 11/1996 | Domb et al. | |
| 5,710,158 A | 1/1998 | Myers et al. | |
| 6,007,845 A | 12/1999 | Domb et al. | |
| 6,610,677 B2 | 8/2003 | Davies et al. | |
| 6,919,338 B2 | 7/2005 | Mortlock et al. | |
| 7,214,518 B2 | 5/2007 | Anderson et al. | |
| 7,772,274 B1 | 8/2010 | Palepu | |
| 8,628,801 B2 | 1/2014 | Garreta et al. | |
| 8,916,206 B2 | 12/2014 | Ishihara et al. | |
| 2003/0181530 A1 | 9/2003 | Ursin | |
| 2004/0096477 A1 | 5/2004 | Chauhan | |
| 2008/0045481 A1 | 2/2008 | Sependa | |
| 2009/0022806 A1 | 1/2009 | Mousa | |
| 2009/0155326 A1 | 6/2009 | Mack | |
| 2009/0247552 A1 | 10/2009 | Sawa | |
| 2009/0312402 A1 | 12/2009 | Contag | |
| 2010/0068286 A1 | 3/2010 | Troiano | |
| 2010/0129456 A1 | 5/2010 | Ishihara et al. | |
| 2011/0125090 A1 | 5/2011 | Peyman | |
| 2011/0200677 A1 | 8/2011 | Chandan | |
| 2014/0178475 A1* | 6/2014 | Figueiredo ............. | A61K 47/12 424/489 |
| 2014/0186452 A1 | 7/2014 | Figueiredo et al. | |
| 2014/0248358 A1* | 9/2014 | Figueiredo ............. | A61K 47/12 424/489 |
| 2014/0249158 A1* | 9/2014 | Figueiredo ............. | A61K 47/12 514/252.18 |
| 2015/0056300 A1 | 2/2015 | Dewitt et al. | |

FOREIGN PATENT DOCUMENTS

| | | |
|---|---|---|
| EP | 0326330 B1 | 8/1989 |
| KR | 20120046595 A | 5/2012 |
| WO | WO 1992/020642 A1 | 11/1992 |
| WO | WO 1995/015758 A1 | 6/1995 |
| WO | WO 1996/009294 A1 | 3/1996 |
| WO | WO 1996/015118 A1 | 5/1996 |
| WO | WO 1996/020698 A2 | 7/1996 |
| WO | WO 1996/039145 A1 | 12/1996 |
| WO | WO 1997/002022 A1 | 1/1997 |
| WO | WO 1997/003069 A1 | 1/1997 |

(Continued)

OTHER PUBLICATIONS

Sarvagalla et al. Therapeutic polymeric nanoparticles and the methods of making and using thereof: a patent evaluation of WO2015036792. Expert Opinion on Therapeutic Patents, 2016, 26(7):751-755. (Year: 2016).*
Balaram, V.M; Asian Journal of Chemistry 2009; vol. 21 No. 7 p. 5241-5244.
Choi, S; International Journal of Pharmaceutics; 2000; vol. 203; p. 193-202.
Faivre, S et al; Nature Rewiews; 2007; vol. 6; p. 734-745.
Govender, T; Journal of Controlled Release; 1999; vol. 57; p. 171-185.
Green, P et al; International Journal of Pharmaceutics; 1987; vol. 37; p. 251-255.

(Continued)

*Primary Examiner* — Robert A Wax
*Assistant Examiner* — Olga V Tcherkasskaya
(74) *Attorney, Agent, or Firm* — Meaghan L. Richmond

(57) ABSTRACT

Described herein are polymeric nanoparticles that include a therapeutic agent which is 2-(3-((7-(3-(ethyl(2-hydroxyethyl)amino)propoxy)quinazolin-4-yl)amino)-1H-pyrazol-5-yl)-N-(3-fluorophenyl)acetamide (also known as AZD1152 hqpa) or a pharmaceutically acceptable salt thereof, and methods of making and using such therapeutic nanoparticles.

5 Claims, 23 Drawing Sheets

(56) References Cited

FOREIGN PATENT DOCUMENTS

| | | |
|---|---|---|
| WO | WO 1999/006378 A1 | 2/1999 |
| WO | WO 2000/021955 A1 | 4/2000 |
| WO | WO 2001/021596 A1 | 3/2001 |
| WO | WO 2001/021597 A1 | 3/2001 |
| WO | WO 2001/087264 A2 | 11/2001 |
| WO | WO 2002/000649 A1 | 1/2002 |
| WO | WO 2002/078674 A1 | 10/2002 |
| WO | WO 2003/000188 A2 | 1/2003 |
| WO | WO 2003/030872 A2 | 4/2003 |
| WO | WO 2003/055491 A1 | 7/2003 |
| WO | WO 2004/006959 A1 | 1/2004 |
| WO | WO 2004/011054 A2 | 2/2004 |
| WO | WO 2004/058781 A1 | 7/2004 |
| WO | WO 2004/089291 A2 | 10/2004 |
| WO | WO 2005/009357 A2 | 2/2005 |
| WO | WO 2005/046572 A2 | 5/2005 |
| WO | WO 2005/104648 A2 | 11/2005 |
| WO | WO 2006/110811 A1 | 10/2006 |
| WO | WO 2007/001356 A2 | 1/2007 |
| WO | WO 2007/069272 A2 | 6/2007 |
| WO | WO 2007/070682 A2 | 6/2007 |
| WO | WO 2007/074604 A1 | 7/2007 |
| WO | WO 2007/133807 A2 | 11/2007 |
| WO | WO 2007/137117 A2 | 11/2007 |
| WO | WO 2007/150030 A2 | 12/2007 |
| WO | WO 2008/019142 A2 | 2/2008 |
| WO | WO 2008/091465 A2 | 7/2008 |
| WO | WO 2008/105773 A2 | 9/2008 |
| WO | WO 2008/109163 A1 | 9/2008 |
| WO | WO 2008/124632 A1 | 10/2008 |
| WO | WO 2008/124639 A2 | 10/2008 |
| WO | WO 2008/128123 A1 | 10/2008 |
| WO | WO 2008/139804 A1 | 11/2008 |
| WO | WO 2008/147456 A2 | 12/2008 |
| WO | WO 2009/040818 A1 | 4/2009 |
| WO | WO 2009/073193 A2 | 6/2009 |
| WO | WO 2009/075401 A1 | 6/2009 |
| WO | WO 2009/117410 A2 | 9/2009 |
| WO | WO 2010/005721 A2 | 1/2010 |
| WO | WO 2010/005723 A2 | 1/2010 |
| WO | WO 2010/005725 A2 | 1/2010 |
| WO | WO 2010/005726 A2 | 1/2010 |
| WO | WO 2010/005740 A2 | 1/2010 |
| WO | WO 2010/009146 A1 | 1/2010 |
| WO | WO 2010005721 A2 * | 1/2010 ............ A61K 9/10 |
| WO | WO 2010/030763 A2 | 3/2010 |
| WO | WO 2010/042555 A2 | 4/2010 |
| WO | WO 2010/068866 A2 | 6/2010 |
| WO | WO 2010/075072 A2 | 7/2010 |
| WO | WO 2010/091187 A2 | 8/2010 |
| WO | WO 2011/075255 A1 | 6/2011 |
| WO | WO 2011/084513 A2 | 7/2011 |
| WO | WO 2011/084518 A2 | 7/2011 |
| WO | WO 2011/084521 A2 | 7/2011 |
| WO | WO 2011/116963 A2 | 9/2011 |
| WO | WO 2011/119262 A1 | 9/2011 |
| WO | WO 2011/150240 A1 | 12/2011 |
| WO | WO 2011/150249 A1 | 12/2011 |
| WO | WO 2011/150258 A1 | 12/2011 |
| WO | WO 2011/150264 A2 | 12/2011 |
| WO | WO 2012/038061 A2 | 3/2012 |
| WO | WO 2012/039979 A2 | 3/2012 |
| WO | WO 2012/040513 A1 | 3/2012 |
| WO | WO 2012/051426 A2 | 4/2012 |
| WO | WO 2012/054923 A2 | 4/2012 |
| WO | WO 2012/066117 A1 | 5/2012 |
| WO | WO 2012/074588 A2 | 6/2012 |
| WO | WO 2012/101639 A2 | 8/2012 |
| WO | WO 2012/142292 A2 | 10/2012 |
| WO | WO 2013/044219 A1 | 3/2013 |
| WO | WO 2013/090840 A1 | 6/2013 |
| WO | WO 2013/127490 A1 | 9/2013 |
| WO | WO 2013/138346 A1 | 9/2013 |
| WO | WO 2014/043618 A1 | 3/2014 |
| WO | WO 2014/043625 A1 | 3/2014 |
| WO | WO 2014147611 A1 * | 9/2014 ............ A61K 45/06 |

OTHER PUBLICATIONS

Gulati, M; International Journal of Pharmaceutics; 1998; vol. 165; p. 129-168.
Jenning, V et al; Internation Journal of Pharmaceutics; 2000; vol. 199; p. 167-177.
Kimura, S; Circulation; 2008; vol. 118; No. 14; S65-S70 & 1-18.
Li; J et al; European Journal of Surgical Oncology; 2011; vol. 37; No. 4; p. 319-324.
Meyer, J et al; Pharmaceutical Research: 1998; vol. 15; No. 2 p. 186-193.
Mortlock, A et al; Chemistry, Molecular Sciences and Chemical Engineering; 2014; p. 3-77.
Okassa, L et al; European Journal of Pharmaceutics and Biopharmaceutics; 2007: vol. 67; No. 1; p. 31-38.
Physical-Chemical Properties and Enviromental Fate for Organic Chemicals; 2006; Ch 13; p. 2668-2776.
Pinkerton, N; Molecular Pharmaceutics; 2013; vol. 10; p. 319-328.
Song, I.S. et al; Pharmacology & Therapeutics; 2013; vol. 138; p. 142-154.
Takacs-Novak, K et al; Pharmaceutical Research; 1999; vol. 16; No. 10; p. 1633-1638.
Vlerken, L; Expert Opinion on Drug Delivery; 2006; vol. 3; No. 2; p. 205-216.
Yoo, H; Journal of Pharmaceutical Sciences; 2000; vol. 90; No. 2; p. 194-201.
Heron et al; SAR and inhibitor complex structure determination of a novel class of potent and specific Aurora kinase inhibitors; Bioorganic & Medicinal Chemistry Letters; 2006; 1320-1323; 16.
Ishihara et al; Efficient Entrapment of Poorly Water-Soluble Pharmaceuticals in Hybrid Nanoparticles; Journal of Pharmaceutical Sciences; 2009; 2357-2363; 98(7).
Jung el al; Discovery of Novel and Potent Thiazoloquinazolines as Selective Aurora A and B Kinase Inhibitors; Journal of Medicinal Chemistry; 2006; 955-970; 49(3).
Mortlock et al; Discovery, Synthesis, and in Vivo Activity of a New Class of Pyrazoloquinazolines as Selective Inhibitors of Aurora B Kinase; Journal of Medicinal Chemistry; 2007; 2213-2224; 50(9).
Mortlock et al; Progress in the Development of Selective Inhibitors of Aurora Kinases; Current Topics in Medicinal Chemistry; 2005; 807-821; 5(8).
Sun et ak; Hydrophobic ion pairing of an insulin-sodium deoxycholate complex for oral delivery of insulin; International Journal of Nanomedicine; 2011; 3049-3056; 6.
Voskoglou-Nomikos et al; Clinical Predictive Value of the in Vitro Cell Line, Human Xenograft, and Mouse Allograft Preclinical Cancer Models; Clinical Cancer Research; 2003; 4227-4239; 9.
Wilkinson et al; AZD1152, a Selective Inhibitor of Aurora B Kinase, Inhibits Human Tumor Xenograft Growth by Inducing Apoptosis; Clinical Cancer Research; 2007; 3682-3688; 13(12).
International Search Report for corresponding PCT Application No. PCT/GB2014/052787; dated Nov. 12, 2014.
Ashton, S; Sci Transl Med; vol. 8 (325) : ra17 325ra17-325ra17 Feb. 10, 2016 Poster.
Ashton, S; Sci Transl Med; vol. 8 (325) : ra17 325ra17 Feb. 10, 2016.
Bavetsias et al. "Aurora Kinase Inhibitors: Current Status and Outlook" Frontiers in Oncology, vol. 5, Art. 278 (2015).
Helfrich, B; The aurora kinase B inhibitor AZD1152-HQPA inhibitor in small cell lung cancer (SCLC) Sep. 6, 2015 Abstract.
Sarvagalla et al. Therapeutic polymeric nanoparticles and the methods of making and using thereof: a patent evaluation of WO2015036792, Exp. Opin. Ther. Pat. 26(7):751-5 (2016).
Song, Y, Journal of Controlled Release; 2016; 229; p. 106-119.
Ashford, M; "Nanomedicines, Designing Formulations to Optimise Benefits;" APS PharmSci 2015—The Science of Medicines; Nottingham, England, Sep. 9, 2015, pp. 1-36.

(56) References Cited

OTHER PUBLICATIONS

Ashford, M; "Examining Novel Delivery Methods for Drug Targeting—Utilising Nanotechnology to Enable New Targets;" Drug Delivery and Formulation Americas, San Diego, CA; May 1, 2014, pp. 1-29.
Ashford, M; "Nanomedicines to Enable innovative Cancer Medicines," European Nanomedicine Meeting, Grenoble, France; Dec. 9, 2015, pp. 1-38.
Ashford, M; "Nanomedicines to Enable Innovative Cancer Medicines;" European Nanomedicine Meeting, Grenoble, France, Dec. 7, 2015, p. 1.
Ashford, M; "Using Nanomedicines to Address Therapeutic Index Challenges;" Nanotechnologies in Drug Delivery Congress, London; England, Apr. 28, 2015, pp. 1-27.
Ashford, M; "Designing Nanomedicines to Improve the Therapeutics Index of Drugs," 10th International Symposium on Polymer Therapeutics From Laboratory to Clinic, CIPF Valencia, Spain, May 19-21, 2014, pp. 1-49.
Ashton, S et al; "AZD1152-hQPA Accurins: nanoparticle formulations showing extended release and the potential for improved therapeutic index;" American Association of Cancer Research Annual Meeting 2014; San Diego; CA; Apr. 5-9, 2014, p. 1.
Ashton, S et al; "Accurin-AZD1152 hQPA nanoparticles inhibit growth of Diffuse Large B-Cell Lymphomas and Small Cell Lung Cancer in preclinical models" American Association of Cancer Research Annual Meeting 2015; Philadelphia, PA; Apr. 18-22, 2015, p. 1.
Ashton, S; "AZD2811(AZD1152 hQPA) Accurins Nanoparticles encapsulating a small molecule Aurora B kinase inhibitor show tumour targeting, extended release and improved therapeutic index;" Cambridge Cancer Symposium; Cambridge, England; Sep. 21-22, 2015, pp. 1-13.
Barry, S; "Imaging Accurin-AZD1152 hQPA nanoparticle accumulation in pre-clinical tumours," American Association of Cancer Research Annual Meeting; Philadelphia, PA; Apr. 18-22, 2015, p. 1.
Barry, S; "Imaging Accurin-AZD1152HQPA nanoparticle accumulation in pre-clinical tumours (Abstract);" American Association of Cancer Research Annual Meeting Philadelphia, PA; Apr. 2015, p. 1.
Cully, M; 'Nanoparticles improve profile of molecularly targeted cancer drug,' Nature Reviews Drug Discovery, vol. 15, No. 4, Apr. 1, 2016, p. 231.
Dixon, L; "From lab to clinic realising the potential of innovation in parenteral drug delivery;" APS PharmSci 2015—The Science of Medicines; Nottingham, England, Sep. 8, 2015, pp. 1-19.
Goodwin, R; "Pharmaceutical MS imaging: A cross platform approach for both targeted and untargeted molecular histology;" American Society for Mass Spectrometry Annual Conference; Baltimore, MD; Jun. 15-19, 2014, pp. 1-35.
Goodwin, R; "Multiplatform mass spectrometry imaging to detect and differentiate nanoparticle formulated and released drug in preclinical tumors;" American Society for Mass Spectrometry Annual Conference; St. Louis, MO; May 31-Jun. 4, 2015, pp. 1-36.
Helfrich B et al; "The aurora kinase B inhibitor AZD1152-HQPA inhibitor in small cell lung cancer (SCLC);" $16^{th}$ World Conference on Lung Cancer; Denver, CO; Sep. 6-9, 2015, pp. 1-9.
Hrkach, J; "Accurins Targeted Nanomedicines through Medicinal Nanoengineering;" Drug Delivery and Formulation Americas; San Diego, CA; May 1, 2014, pp. 1-24.
Swales, J et al; "Assessment of nanoparticle accumulation and drug release in xenografts by high spatial resolution mass spectrometry imaging;" Ourcon II Mass Spectrometry Imaging Conference; Antalya, Turkey; Nov. 18-21, 2014, p. 1.
Toxnet Database, Oleic Acid, CASRN:112-80-1, retrieved from <http://toxnet.nlm.nih.gov/> on Sep. 3, 2014, 22 pages.
Extended European Search Report of EP 17181565.7 filed Jul. 14, 2017; Search Report dated Feb. 16, 2018, pp. 1-2.

* cited by examiner

Plasma concentrations (1207)
Total extracted levels of AZD1152hqpa

Two representations showing in-vivo exposure results from Example 6

Formulation F1 and F2 give equivalent tumour control to Formulation E in rats bearing SW620 tumours. Mean tumour size for each group is represented. Bars represent standard error of mean.

In vivo activity of AZD1152 and AZD1152-HQPA nanoparticle Formulations E/F1/F2

Effects of Formulations E, F1, F2 on Bone marrow integrity.

Effects of Formulations E, F1, F2 on Bone marrow integrity.

In vivo activity of AZD1152 and AZD1152- HQPA nanoparticle Formulations G1 and G2

Effects of Formulations G1 and G2 on Bone marrow integrity.

Formulation G1 gives equivalent tumour control to AZD1152 in mice bearing U2932 tumours. Mean tumour size for each group is represented. Bars represent standard error of mean.

Formulation G1 gives longer tumour control than AZD1152 in
mice bearing SC-61 primary tumours. Mean tumour size for each group is represented in
$mm^3$. Bars represent standard error of mean (SEM)

In-vitro release at 37 °C of batches shown in Example 11.

THERAPEUTIC POLYMERIC NANOPARTICLES AND METHODS OF MAKING AND USING SAME

This application claims the benefit under 35 U.S.C. § 119(e) of Application No. 61/878,227 filed on 16 Sep. 2013 and Application No. 61/939,332 filed on 13 Feb. 2014.

BACKGROUND

Systems that deliver certain drugs to a patient (e.g., distributed preferentially to a particular tissue or cell type or to a specific diseased tissue more than to normal tissue) or that control release of drugs have long been recognized as beneficial.

For example, therapeutics that include an active agent distributed preferentially to a specific diseased tissue more than to normal tissue, may increase the exposure of the drug in those tissues over others in the body. This is particularly important when treating a condition such as cancer where it is desirable that a cytotoxic dose of the drug is delivered to cancer cells without killing the surrounding non-cancerous tissue. Effective drug distribution may reduce the undesirable and sometimes life threatening side effects common in anticancer therapy.

Nanoparticles, by virtue of their size and surface properties, should allow prolonged circulation in the vasculature and preferential tissue accumulation through defective architecture of diseased tissues/tumours via the Enhanced Permeation and Retention effect.

Therapeutics that offer controlled release therapy also must be able to deliver an effective amount of drug, which is a known limitation in some nanoparticle delivery systems. For example, it can be a challenge to prepare nanoparticle systems that have an appropriate amount of drug associated with each nanoparticle, while keeping the size of the nanoparticles small enough to have advantageous delivery properties.

Accordingly, a need exists for nanoparticle therapeutics and methods of making such nanoparticles that are capable of delivering therapeutic levels of the therapeutic agent to treat diseases such as cancer, while also reducing patient side effects.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, an ordered cascade of protein phosphorylation is thought to control the cell cycle. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

Aurora Kinases (Aurora-A, Aurora-B and Aurora-C) encode cell cycle regulated serine-threonine protein kinases (summarised in Adams et al., 2001, Trends in Cell Biology. 11(2): 49-54). These show a peak of expression and kinase activity through G2 and mitosis and a role for human Aurora kinases in cancer has long been implicated.

The Aurora Kinase inhibitor known as AZD1152 (2-(ethyl (3-((4-((5-(2-((3-fluorophenyl)amino)-2-oxoethyl)-1H-pyrazol-3-yl)amino)quinazolin-7-yl)oxy)propyl)amino) ethyl dihydrogen phosphate), pictured below, also known as barasertib, was first disclosed in International Patent Application WO2004/058781 (Example 39) and has been studied by AstraZeneca as a potential treatment for various cancers. However there are practical challenges in the clinical administration of AZD1152 as an intravenous solution delivered continuously over multiple days.

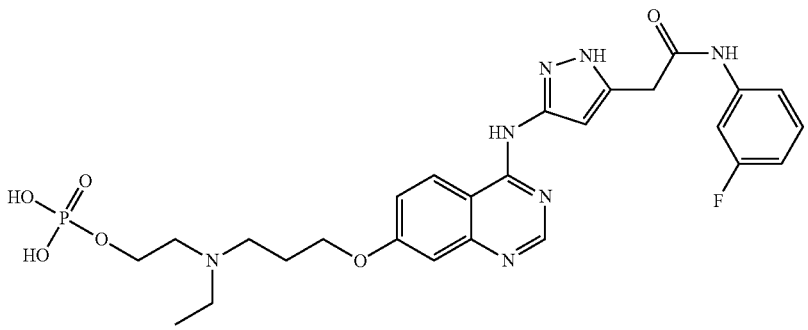

AZD1152

It is known that AZD1152 is metabolized in vivo to a compound known as AZD1152 hqpa (2-(3-((7-(3-(ethyl(2-hydroxyethyl)amino)propoxy)quinazolin-4-yl)amino)-1H-pyrazol-5-yl)-N-(3-fluorophenyl)acetamide), also disclosed in WO2004/058781. AZD1152 hqpa is in fact, to a large extent, the moiety exerting the biological effect when AZD1152 itself is administered. However pharmaceutical compositions of AZD1152 hqpa, particularly those suitable for commercial administration, have not previously been specifically described or tested.

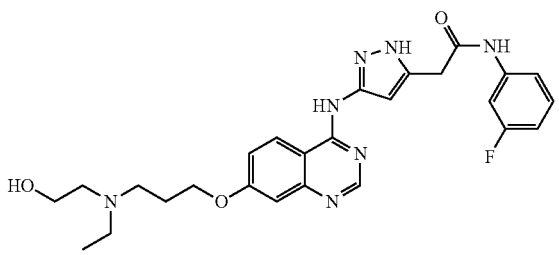

AZD1152 hqpa

Nanoparticulate formulations including basic therapeutic agents with a protonatable nitrogen are described in WO2014/043625.

SUMMARY

Described herein are polymeric nanoparticles that include AZD1152 hqpa or a pharmaceutically acceptable salt thereof as a therapeutic agent, and methods of making and using such therapeutic nanoparticles.

References herein to "the" or "a" "therapeutic agent" should be understood to mean AZD1152 hqpa or a pharmaceutically acceptable salt thereof, unless the context dictates otherwise.

In particular, the therapeutic agent is AZD1152 hqpa.

In one aspect, a therapeutic nanoparticle is provided. The therapeutic nanoparticle comprises about 50 to about 99.75 weight percent of a diblock poly(lactic) acid-poly(ethylene) glycol copolymer or a diblock poly(lactic acid-co-glycolic acid)-poly(ethylene)glycol copolymer, wherein the therapeutic nanoparticle comprises about 10 to about 30 weight percent poly(ethylene)glycol, and about 0.2 to about 30 weight percent of AZD1152 hqpa or a pharmaceutically acceptable salt thereof, particularly AZD1152 hqpa.

In another aspect there is provided a therapeutic nanoparticle comprising AZD1152 hqpa and a suitable polymer.

In another aspect, there is provided a therapeutic nanoparticle comprising AZD1152 hqpa, a suitable polymer and a hydrophobic acid.

In another aspect, there is provided a therapeutic nanoparticle comprising AZD1152 hqpa, a suitable polymer and a hydrophobic acid selected from cholic acid, deoxycholic acid, pamoic acid and dioctyl sulfosuccinic acid.

Dioctyl sulfosuccinic acid is also referred to as docusate acid herein. Dioctyl sodium sulfosuccinate is also known as sodium docusate.

In another aspect, there is provided a therapeutic nanoparticle comprising AZD1152 hqpa, a suitable polymer and pamoic acid.

In another aspect, there is provided a therapeutic nanoparticle comprising a suitable polymer and a mixture of AZD1152 hqpa and a hydrophobic acid.

In another aspect there is provided a therapeutic nanoparticle comprising a suitable polymer and the product obtained by interaction of AZD1152 hqpa and a hydrophobic acid.

In a further aspect there is provided a therapeutic nanoparticle comprising a suitable polymer and a hydrophobic ion pair formed between AZD1152 hqpa and a hydrophobic acid.

In another aspect, there is provided a therapeutic nanoparticle comprising AZD1152 hqpa, a diblock poly(lactic) acid-poly(ethylene)glycol copolymer and a hydrophobic acid.

In another aspect, there is provided a therapeutic nanoparticle comprising a diblock poly(lactic) acid-poly(ethylene)glycol copolymer and a mixture of AZD1152 hqpa and a hydrophobic acid.

In another aspect, there is provided a therapeutic nanoparticle comprising a diblock poly(lactic) acid-poly(ethylene)glycol copolymer and the product obtained by interaction of AZD1152 hqpa and a hydrophobic acid.

In a further aspect there is provided a therapeutic nanoparticle comprising a diblock poly(lactic) acid-poly(ethylene)glycol copolymer and a hydrophobic ion pair formed between AZD1152 hqpa and a hydrophobic acid.

In another aspect, there is provided a therapeutic nanoparticle comprising AZD1152 hqpa, a diblock poly(lactic) acid-poly(ethylene)glycol copolymer and a hydrophobic acid selected from cholic acid, deoxycholic acid, pamoic acid and dioctyl sulfosuccinic acid.

In another aspect, there is provided a therapeutic nanoparticle comprising AZD1152 hqpa, a diblock poly(lactic) acid-poly(ethylene)glycol copolymer and pamoic acid.

In another aspect, there is provided a therapeutic nanoparticle comprising a diblock poly(lactic) acid-poly(ethylene)glycol copolymer and a mixture of AZD1152 hqpa and a hydrophobic acid selected from cholic acid, deoxycholic acid, pamoic acid and dioctyl sulfosuccinic acid.

In another aspect there is provided a therapeutic nanoparticle comprising a diblock poly(lactic) acid-poly(ethylene)glycol copolymer and the product obtained by interaction of AZD1152 hqpa and a hydrophobic acid selected from cholic acid, deoxycholic acid, pamoic acid and dioctyl sulfosuccinic acid.

In a further aspect there is provided a therapeutic nanoparticle comprising a diblock poly(lactic) acid-poly(ethylene)glycol copolymer and a hydrophobic ion pair formed between AZD1152 hqpa and a hydrophobic acid selected from cholic acid, deoxycholic acid, pamoic acid and dioctyl sulfosuccinic acid.

In another aspect, there is provided a therapeutic nanoparticle comprising a diblock poly(lactic) acid-poly(ethylene)glycol copolymer and a mixture of AZD1152 hqpa and pamoic acid.

In another aspect there is provided a therapeutic nanoparticle comprising a diblock poly(lactic) acid-poly(ethylene)glycol copolymer and the product obtained by interaction of AZD1152 hqpa and pamoic acid.

In a further aspect there is provided a therapeutic nanoparticle comprising a diblock poly(lactic) acid-poly(ethylene)glycol copolymer and a hydrophobic ion pair formed between AZD1152 hqpa and pamoic acid.

In another aspect, there is provided a therapeutic nanoparticle comprising AZD1152 hqpa, a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene) glycol) and a hydrophobic acid selected from cholic acid, deoxycholic acid, pamoic acid and dioctyl sulfosuccinic acid.

In another aspect there is provided a therapeutic nanoparticle comprising about 50 to about 94.95 weight percent of a diblock poly(lactic) acid-poly(ethylene)glycol copolymer or a diblock poly(lactic acid-co-glycolic acid)-poly(ethylene)glycol copolymer, wherein the therapeutic nanoparticle comprises about 10 to about 30 weight percent poly(ethylene)glycol, about 0.05 to about 35 weight percent of a substantially hydrophobic acid and about 5 to about 30 weight percent of AZD1152 hqpa or a pharmaceutically acceptable salt thereof, particularly AZD1152 hqpa.

In another aspect there is provided a therapeutic nanoparticle comprising about 50 to about 94 weight percent of a diblock poly(lactic) acid-poly(ethylene)glycol copolymer or a diblock poly(lactic acid-co-glycolic acid)-poly(ethylene)glycol copolymer, wherein the therapeutic nanoparticle comprises about 10 to about 30 weight percent poly(ethylene)glycol, about 1 to about 35 weight percent of a substantially hydrophobic acid and about 5 to about 30 weight percent of AZD1152 hqpa or a pharmaceutically acceptable salt thereof, particularly AZD1152 hqpa.

In another aspect, a therapeutic nanoparticle is provided. The therapeutic nanoparticle comprises about 50 to about 99.75 weight percent of a diblock poly(lactic) acid-poly(ethylene)glycol copolymer, wherein the therapeutic nanoparticle comprises about 10 to about 30 weight percent poly(ethylene)glycol, about 0.05 to about 35 weight percent of a substantially hydrophobic acid selected from the group consisting of deoxycholic acid, cholic acid and dioctyl sulfosuccinic acid, and about 5 to about 30 weight percent of AZD1152 hqpa or a pharmaceutically acceptable salt thereof. In another aspect, a mixture of cholic acid and deoxycholic acid are used in a total of about 0.05 to about 35 weight percent of the nanoparticle. In a further aspect the hydrophobic acid is oleic acid.

In another aspect, the therapeutic nanoparticle comprises about 35 to about 94.75 weight percent of a diblock poly(lactic) acid-poly(ethylene)glycol copolymer, wherein the therapeutic nanoparticle comprises about 10 to about 30 weight percent poly(ethylene)glycol, about 0.05 to about 35 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 30 weight percent of AZD1152 hqpa or a pharmaceutically acceptable salt thereof.

In another aspect, the therapeutic nanoparticle comprises about 35 to about 94 weight percent of a diblock poly(lactic) acid-poly(ethylene)glycol copolymer, wherein the therapeutic nanoparticle comprises about 10 to about 30 weight percent poly(ethylene)glycol, about 1 to about 35 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 30 weight percent of AZD1152 hqpa or a pharmaceutically acceptable salt thereof.

In another aspect, the therapeutic nanoparticle comprises about 65 to about 90 weight percent of a diblock poly(lactic) acid-poly(ethylene)glycol copolymer, wherein the therapeutic nanoparticle comprises about 10 to about 30 weight percent poly(ethylene)glycol, about 5 to about 15 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 20 weight percent of AZD1152 hqpa or a pharmaceutically acceptable salt thereof.

In another aspect, there is provided a therapeutic nanoparticle comprising about 35 to about 94 weight percent of a diblock poly(lactic) acid-poly(ethylene)glycol copolymer, wherein the therapeutic nanoparticle comprises about 10 to about 30 weight percent poly(ethylene)glycol, and a mixture of:
  a) about 1 to about 35 weight percent of a substantially hydrophobic acid selected from the group consisting of deoxycholic acid, cholic acid, a mixture of cholic and deoxycholic acid, dioctyl sulfosuccinic acid and pamoic acid; and
  b) about 5 to about 30 weight percent of AZD1152 hqpa.

In another aspect there is provided a therapeutic nanoparticle comprising about 35 to about 94 weight percent of a diblock poly(lactic) acid-poly(ethylene)glycol copolymer, wherein the therapeutic nanoparticle comprises about 10 to about 30 weight percent poly(ethylene)glycol, and the product obtained by interaction of:
  a) about 1 to about 35 weight percent of a substantially hydrophobic acid selected from the group consisting of deoxycholic acid, cholic acid, a mixture of cholic and deoxycholic acid, dioctyl sulfosuccinic acid and pamoic acid; and
  b) about 5 to about 30 weight percent of AZD1152 hqpa.

In a further aspect there is provided a therapeutic nanoparticle comprising about 35 to about 94 weight percent of a diblock poly(lactic) acid-poly(ethylene)glycol copolymer, wherein the therapeutic nanoparticle comprises about 10 to about 30 weight percent poly(ethylene)glycol, and a hydrophobic ion pair formed between:
  a) about 1 to about 35 weight percent of a substantially hydrophobic acid selected from the group consisting of deoxycholic acid, cholic acid, a mixture of cholic and deoxycholic acid, dioctyl sulfosuccinic acid and pamoic acid; and
  b) about 5 to about 30 weight percent of AZD1152 hqpa.

In another aspect, the therapeutic nanoparticle comprises about 35 to about 94.75 weight percent of a diblock poly(lactic) acid-poly(ethylene)glycol copolymer, wherein the therapeutic nanoparticle comprises about 10 to about 30 weight percent poly(ethylene)glycol, about 0.05 to about 35 weight percent of pamoic acid and about 5 to about 30 weight percent of AZD1152 hqpa or a pharmaceutically acceptable salt thereof.

In another aspect, the therapeutic nanoparticle comprises about 35 to about 94 weight percent of a diblock poly(lactic) acid-poly(ethylene)glycol copolymer, wherein the therapeutic nanoparticle comprises about 10 to about 30 weight percent poly(ethylene)glycol, about 1 to about 35 weight percent of pamoic acid and about 5 to about 30 weight percent of AZD1152 hqpa or a pharmaceutically acceptable salt thereof.

In another aspect, the therapeutic nanoparticle comprises about 55 to about 80 weight percent of a diblock poly(lactic) acid-poly(ethylene)glycol copolymer, wherein the therapeutic nanoparticle comprises about 10 to about 30 weight percent poly(ethylene)glycol, about 10 to about 20 weight percent of pamoic acid and about 10 to about 25 weight percent of AZD1152 hqpa or a pharmaceutically acceptable salt thereof.

In another aspect, the therapeutic nanoparticle comprises about 35 to about 94.75 weight percent of a diblock poly(lactic) acid-poly(ethylene)glycol copolymer, wherein the therapeutic nanoparticle comprises about 10 to about 30 weight percent poly(ethylene)glycol, about 0.05 to about 35 weight percent of pamoic acid and about 5 to about 30 weight percent of AZD1152 hqpa.

In another aspect, the therapeutic nanoparticle comprises about 35 to about 94 weight percent of a diblock poly(lactic) acid-poly(ethylene)glycol copolymer, wherein the therapeutic nanoparticle comprises about 10 to about 30 weight percent poly(ethylene)glycol, about 1 to about 35 weight percent of pamoic acid and about 5 to about 30 weight percent of AZD1152 hqpa.

In another aspect, the therapeutic nanoparticle comprises about 55 to about 85 weight percent of a diblock poly(lactic) acid-poly(ethylene)glycol copolymer, wherein the therapeutic nanoparticle comprises about 10 to about 30 weight percent poly(ethylene)glycol, about 5 to about 20 weight percent of pamoic acid and about 10 to about 25 weight percent of AZD1152 hqpa.

In another aspect, there is provided a therapeutic nanoparticle comprising about 55 to about 85 weight percent of a diblock poly(lactic) acid-poly(ethylene)glycol copolymer, wherein the therapeutic nanoparticle comprises about 10 to about 30 weight percent poly(ethylene)glycol, and a mixture of about 10 to about 25 weight percent of AZD1152 hqpa and about 5 to about 20 weight percent pamoic acid.

In another aspect there is provided a therapeutic nanoparticle comprising about 55 to about 85 weight percent of a diblock poly(lactic) acid-poly(ethylene)glycol copolymer, wherein the therapeutic nanoparticle comprises about 10 to about 30 weight percent poly(ethylene)glycol, and the product obtained by interaction of about 10 to about 25 weight percent of AZD1152 hqpa and about 5 to about 20 weight percent of pamoic acid.

In a further aspect there is provided a therapeutic nanoparticle comprising about 55 to about 85 weight percent of a diblock poly(lactic) acid-poly(ethylene)glycol copolymer, wherein the therapeutic nanoparticle comprises about 10 to about 30 weight percent poly(ethylene)glycol, and a hydrophobic ion pair formed between about 10 to about 25 weight percent of AZD1152 hqpa and about 5 to about 20 weight percent of pamoic acid.

In another aspect, the therapeutic nanoparticle comprises a diblock poly(lactic) acid-poly(ethylene)glycol copolymer, wherein the therapeutic nanoparticle comprises about 10 to about 30 weight percent poly(ethylene)glycol, about 7 to about 15 weight percent of pamoic acid and about 15 to about 22 weight percent of AZD1152 hqpa.

In another aspect there is provided a therapeutic nanoparticle comprising a diblock poly(lactic) acid-poly(ethylene)glycol copolymer, wherein the therapeutic nanoparticle comprises about 10 to about 30 weight percent poly(ethylene)glycol, and the product obtained by interaction of about 15 to about 22 weight percent of AZD1152 hqpa and about 7 to about 15 weight percent of pamoic acid.

In a further aspect there is provided a therapeutic nanoparticle comprising a diblock poly(lactic) acid-poly(ethylene)glycol copolymer, wherein the therapeutic nanoparticle comprises about 10 to about 30 weight percent poly(ethylene)glycol, and a hydrophobic ion pair formed between about 15 to about 22 weight percent of AZD1152 hqpa and about 7 to about 15 weight percent of pamoic acid.

In another aspect, the therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol), about 7 to about 15 weight percent of pamoic acid and about 15 to about 22 weight percent of AZD1152 hqpa.

In another aspect there is provided a therapeutic nanoparticle comprising a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and the product obtained by interaction of about 15 to about 22 weight percent of AZD1152 hqpa and about 7 to about 15 weight percent of pamoic acid.

In a further aspect there is provided a therapeutic nanoparticle comprising a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and a hydrophobic ion pair formed between about 15 to about 22 weight percent of AZD1152 hqpa and about 7 to about 15 weight percent of pamoic acid.

In another aspect, the therapeutic nanoparticle comprises about 65 to about 76 weight percent of a diblock poly(lactic) acid-poly(ethylene)glycol copolymer, wherein the therapeutic nanoparticle comprises about 10 to about 20 weight percent poly(ethylene)glycol, about 9 to about 15 weight percent of pamoic acid and about 15 to about 20 weight percent of AZD1152 hqpa or a pharmaceutically acceptable salt thereof.

In some embodiments, the poly(lactic) acid-poly(ethylene)glycol copolymer has a poly(lactic) acid number average molecular weight fraction of about 0.7 to about 0.9. In other embodiments, the poly(lactic) acid-poly(ethylene)glycol copolymer has a poly(lactic) acid number average molecular weight fraction of about 0.75 to about 0.85.

In certain embodiments, contemplated nanoparticles comprise about 10 to about 25 weight percent poly(ethylene)glycol. In other embodiments, contemplated nanoparticles comprise about 20 to about 30 weight percent poly(ethylene)glycol.

In some embodiments, the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol. In other embodiments, the poly(lactic) acid-poly(ethylene)glycol copolymer has a number average molecular weight of about 16 kDa poly(lactic acid) and a number average molecular weight of about 5 kDa poly(ethylene)glycol.

In certain embodiments, contemplated nanoparticles comprise about 65 weight percent to about 85 weight percent of the copolymer.

In some embodiments, contemplated nanoparticles have a hydrodynamic diameter of <200 nm, such as 70-140 nm.

In some embodiments, contemplated nanoparticles comprise a substantially hydrophobic acid, also referred to herein as "hydrophobic acid". For example, contemplated nanoparticles may comprise about 0.05 to about 35 weight percent of a substantially hydrophobic acid, about 5 to about 15 weight percent of a substantially hydrophobic acid, or about 10 to about 20 weight percent of a substantially hydrophobic acid. Contemplated nanoparticles may, in other embodiments, comprise about 5 to about 20 weight percent of a substantially hydrophobic acid. In certain embodiments more than one substantially hydrophobic acid may be used, and the contemplated nanoparticles may comprise about 5 to about 15 weight percent, or about 10 to about 20 weight percent of the total hydrophobic acids together. Contemplated nanoparticles may, in other embodiments, comprise about 5 to about 15 weight percent of a substantially hydrophobic acid selected from deoxycholic acid, cholic acid, a mixture of deoxycholic acid and cholic acid, dioctyl sulfosuccinic acid and pamoic acid.

In certain embodiments, the molar ratio of the substantially hydrophobic acid to the therapeutic agent is about 0.9:1 to about 1.1:1, wherein the acid is deoxycholic acid. In other embodiments, the molar ratio of the substantially hydrophobic acid to the therapeutic agent is about 0.9:1 to about 1.1:1, wherein the acid is dioctyl sulfosuccinic acid. In a further embodiment, the hydrophobic acid content comprises a mixture of deoxycholic acid and cholic acid, for example in a ratio of between 1:5 and 5:1 deoxycholic acid:cholic acid, such as about 3:2 deoxycholic acid:cholic acid. In other embodiments the molar ratio of the substantially hydrophobic acid to the therapeutic agent is about 0.75:1 to about 1.0:1, wherein the acid is pamoic acid.

In some embodiments, a $pK_a$ of the therapeutic agent is at least about 1.0 $pK_a$ units greater than a $pK_a$ of the hydrophobic acid.

In certain embodiments, the substantially hydrophobic acid and the therapeutic agent form a hydrophobic ion pair in a contemplated therapeutic nanoparticle. In some embodiments, the hydrophobic acid is a bile acid. For example, in some embodiments, the bile acid is deoxycholic acid. In other embodiments, the bile acid is cholic acid. In still further embodiments the bile acid is a mixture of deoxycholic acid and cholic acid. In other embodiments, the hydrophobic acid is dioctyl sulfosuccinic acid. In still further embodiments the hydrophobic acid is oleic acid. In further embodiments, the hydrophobic acid is pamoic acid.

In some embodiments, contemplated nanoparticles comprise about 5 to about 20 weight percent of the therapeutic agent. In other embodiments, contemplated nanoparticles comprise about 10 to about 20 weight percent of the therapeutic agent. In other embodiments, contemplated nanoparticles comprise about 15 to about 20 weight percent of the therapeutic agent. In other embodiments, contemplated nanoparticles comprise about 8 to about 15 weight percent of the therapeutic agent. In other embodiments, contemplated nanoparticles comprise about 8 to about 20 weight percent of the therapeutic agent.

It will be understood that the composition of any preferred formulation may be a balance of several factors, including but not limited to:

a formulation with increased drug loading where possible to minimize the volume of pharmaceutical composition which must be administered to the patient;

the formulation which can be achieved reproducibly and reliably on large scale manufacture;

the formulation which optimizes release profile of the therapeutic agent over time;

the formulation which preferentially distributes to diseased sites.

A further factor may be a formulation which has reduced or minimal detrimental effect on the bone marrow of a patient after dosing, as exemplified in animal models in the Examples hereinafter.

In any particular preferred formulation, any one or more of the above factors may be taken into consideration.

In another aspect, there is provided a nanoparticle obtainable by any process described or exemplified herein. In another aspect, there is provided a nanoparticle obtained by any process described or exemplified herein. In a further aspect, there is provided a therapeutic nanoparticle substantially as described herein.

In another aspect, a pharmaceutically acceptable composition is provided. The pharmaceutically acceptable composition comprises a plurality of contemplated therapeutic nanoparticles and a pharmaceutically acceptable excipient.

In yet another aspect, a method of treating cancer (for example including, but not limited to, haematological cancers such as Acute Myeloid Leukaemia (AML) and Diffuse Large B-Cell Lymphoma, and solid tumour cancers such as colorectal cancer and lung cancer) in a patient in need thereof is provided. The method comprises administering to the patient a therapeutically effective amount of a composition comprising therapeutic nanoparticles contemplated herein.

DETAILED DESCRIPTION

Figure 1:
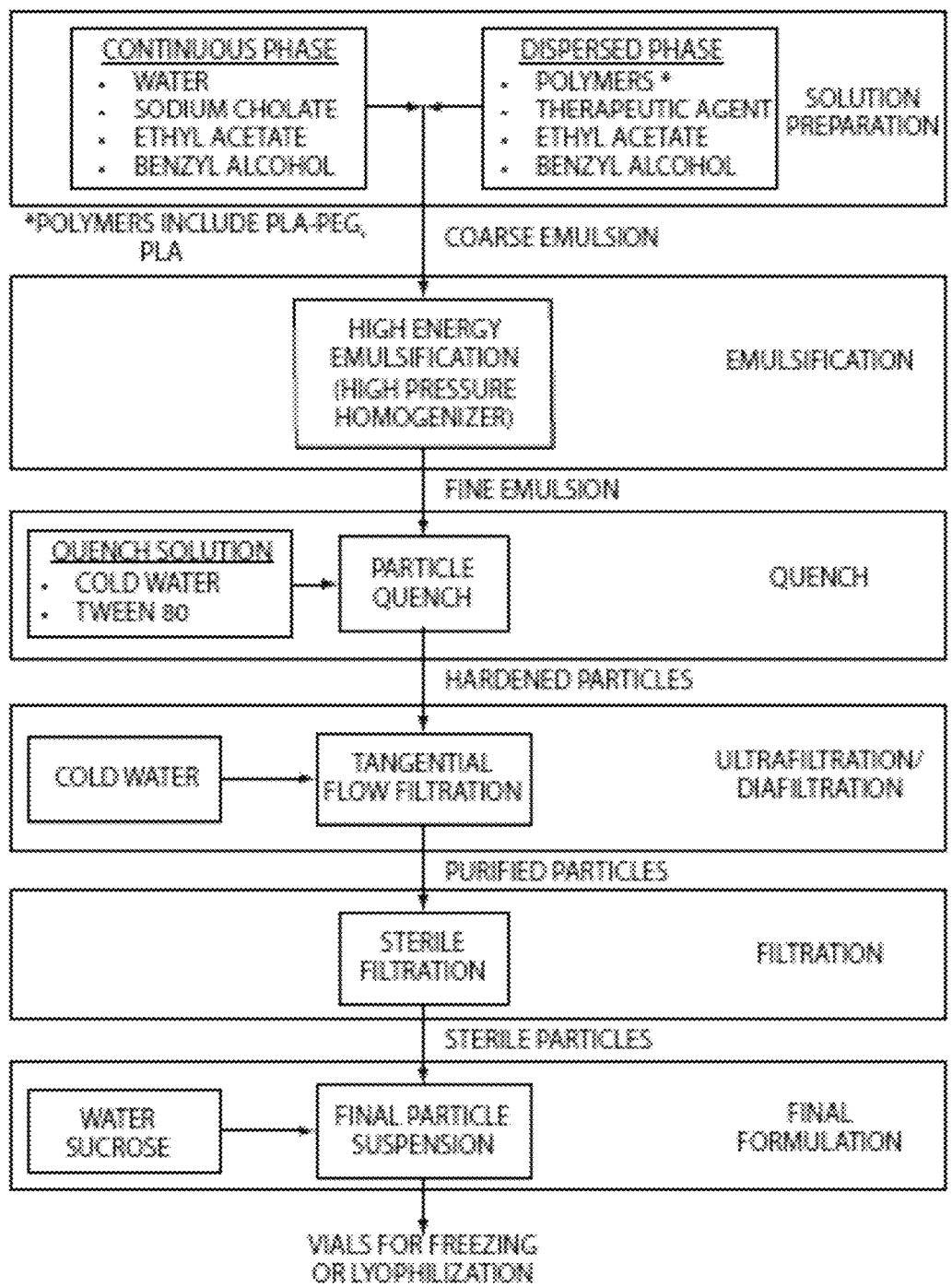
FIG. 1 is flow chart for an emulsion process for forming a disclosed nanoparticle.

Described herein are polymeric nanoparticles that include AZD1152 hqpa or a pharmaceutically acceptable salt thereof as a therapeutic agent, and methods of making and using such therapeutic nanoparticles. In some embodiments, inclusion (doping) of a substantially hydrophobic acid (such as a bile acid or other suitable acids as disclosed herein) in a disclosed nanoparticle and/or included in a nanoparticle preparation process may result in nanoparticles that include improved drug loading. Furthermore, in certain embodiments, nanoparticles that include and/or are prepared in the presence of the hydrophobic acid may exhibit improved controlled release properties. For example, disclosed nanoparticles may more slowly release the therapeutic agent as compared to nanoparticles prepared in the absence of the hydrophobic acid.

Without wishing to be bound by any theory, it is believed that the disclosed nanoparticle formulations that include a hydrophobic acid (such as a bile acid or other suitable acids as disclosed herein) have significantly improved formulation properties (e.g., drug loading and/or release profile) which may occur through formation of a hydrophobic ion-pair (HIP), between the substantially hydrophobic acid and, e.g., an amine group of the therapeutic agent. As used herein, a HIP is a pair of oppositely charged ions held together by Coulombic attraction. Also without wishing to be bound by any theory, in some embodiments, a HIP can be used to increase the hydrophobicity of the therapeutic agent. In some embodiments, a therapeutic agent with increased hydrophobicity can be beneficial for nanoparticle formulations and result in HIP formation that may provide higher solubility of the therapeutic agent in organic solvents. HIP formation, as contemplated herein, can result in nanoparticles having for example, increased drug loading. Slower release of the therapeutic agent from the nanoparticles may also occur, for example in some embodiments, due to a decrease in the therapeutic agent's solubility in aqueous solution. Furthermore, complexing the therapeutic agent with large hydrophobic counter ions may slow diffusion of the therapeutic agent within the polymeric matrix. Advantageously, HIP formation occurs without the need for covalent conjugation of the hydrophobic group to the therapeutic agent.

Without wishing to be bound by any theory, it is believed that the strength of the HIP may impact the drug load and release rate of the contemplated nanoparticles. For example, the strength of the HIP may be increased by increasing the magnitude of the difference between the $pK_a$ of the therapeutic agent and the $pK_a$ of the hydrophobic acid, as discussed in more detail below. Also without wishing to be bound by any theory, it is believed that the conditions for ion pair formation may impact the drug load and release rate of the contemplated nanoparticles.

Whatever the exact nature of the interaction (as described above) between AZD1152 hqpa and the hydrophobic acids in the disclosed formulations, preferred formulations are those comprising a hydrophobic acid and which have high drug loading (for example about 15 to about 25 weight percent (wt %) AZD1152 hqpa, such as about 15 to about 22 wt %, or about 15 to about 20 wt % AZD1152 hqpa) and a suitable release profile, as discussed in more detail hereinafter. Suitably, such formulations also have reduced impact on bone marrow in comparison with other formulations which comprise AZD1152.

Nanoparticles disclosed herein include one, two, three or more biocompatible and/or biodegradable polymers. For example, a contemplated nanoparticle may include about 35 to about 99.75 weight percent, in some embodiments about 50 to about 99.75 weight percent, in some embodiments about 50 to about 99.5 weight percent, in some embodiments about 50 to about 99 weight percent, in some embodiments about 50 to about 98 weight percent, in some embodiments about 50 to about 97 weight percent, in some embodiments about 50 to about 96 weight percent, in some embodiments about 50 to about 95 weight percent, in some embodiments about 50 to about 94 weight percent, in some embodiments about 50 to about 93 weight percent, in some embodiments about 50 to about 92 weight percent, in some embodiments about 50 to about 91 weight percent, in some embodiments about 50 to about 90 weight percent, in some embodiments about 50 to about 85 weight percent, in some embodiments about 50 to about 80 weight percent, and in some embodiments about 65 to about 85 weight percent of one or more block copolymers that include a biodegradable polymer and poly(ethylene glycol) (PEG), and about 0 to about 50 weight percent of a biodegradable homopolymer.

AZD1152 hqpa

The disclosed nanoparticles include AZD1152 hqpa ($pK_{a1}$=5.7; $pK_{a2}$=8.46) or a pharmaceutically acceptable salt thereof as a therapeutic agent. Reference herein to a therapeutic agent should be understood as referring to AZD1152 hqpa or a pharmaceutically acceptable salt thereof, but particularly AZD1152 hqpa, unless the context indicates otherwise.

In a first aspect of the invention there is provided a nanoparticle comprising AZD1152 hqpa. In a further aspect of the invention there is provided a therapeutic nanoparticle comprising AZD1152 hqpa and a hydrophobic acid. In a further aspect of the invention there is provided a therapeutic nanoparticle comprising the product obtained by the interaction of AZD1152 hqpa and a hydrophobic acid. In a further aspect of the invention there is provided a therapeutic nanoparticle comprising the product obtained by mixing AZD1152 hqpa and a hydrophobic acid. In a further aspect of the invention there is provided a therapeutic nanoparticle comprising a hydrophobic ion pair between AZD1152 hqpa and a hydrophobic acid.

In another aspect of the invention there is provided a pharmaceutical composition comprising AZD1152 hqpa in a nanoparticle. In a further aspect of the invention there is provided a therapeutic nanoparticle comprising AZD1152 hqpa and a hydrophobic acid. In a further aspect of the invention there is provided a pharmaceutical composition comprising a therapeutic nanoparticle which comprises the product obtained by the interaction of AZD1152 hqpa and a hydrophobic acid. In a further aspect of the invention there is provided a pharmaceutical composition comprising a therapeutic nanoparticle which comprises the product obtained by mixing AZD1152 hqpa and a hydrophobic acid. In a further aspect of the invention there is provided a pharmaceutical composition comprising a therapeutic nanoparticle which comprises a hydrophobic ion pair between AZD1152 hqpa and a hydrophobic acid.

In another aspect of the invention there is provided a pharmaceutical composition comprising a plurality of therapeutic nanoparticles containing AZD1152 hqpa as an active ingredient. Such nanoparticles suitably also contain a hydrophobic acid, such as pamoic acid, mixed with the AZD1152 hqpa in the nanoparticles and further contain a suitable polymer such as a 16/5 PLA-PEG copolymer.

A suitable pharmaceutically-acceptable salt of AZD1152 hqpa may be, for example, an acid-addition salt of AZD1152 hqpa, for example an acid-addition salt with a strong inorganic or organic acid such as hydrochloric, hydrobromic, sulphuric or trifluoroacetic acid. Other suitable pharmaceutically-acceptable salts include phosphate, acetate, fumarate, maleate, tartrate, citrate, methanesulphonate, and p-toluenesulphonate. Still further suitable pharmaceutically-acceptable salts include salts of AZD1152 hqpa with acids such as hydrophobic acids defined herein. It will be understood that a counterion for a suitable salt of AZD1152 hqpa input into the manufacturing process must be chosen such that it does not interfere with the process for formation of the nanoparticles as described herein. Counterions which are readily washed out from the solutions or which correspond to counterions already present in the process may conveniently be used.

In some embodiments, disclosed nanoparticles may include about 0.2 to about 35 weight percent, about 0.2 to about 20 weight percent, about 0.2 to about 10 weight percent, about 0.2 to about 5 weight percent, about 0.5 to about 5 weight percent, about 0.75 to about 5 weight percent, about 1 to about 5 weight percent, about 2 to about 5 weight percent, about 3 to about 5 weight percent, about 1 to about 20 weight percent, about 2 to about 20 weight percent, about 5 to about 20 weight percent, about 1 to about 15 weight percent, about 2 to about 15 weight percent, about 3 to about 15 weight percent, about 4 to about 15 weight percent, about 5 to about 15 weight percent, about 1 to about 10 weight percent, about 2 to about 10 weight percent, about 3 to about 10 weight percent, about 4 to about 10 weight percent, about 5 to about 10 weight percent, about 10 to about 30 weight percent, about 15 to about 25, or about 15 to about 20 weight percent of the therapeutic agent.

In particular aspects, disclosed nanoparticles may include about 5 to about 20, preferably about 10 to about 20, even more preferably about 15 to about 20 weight percent of AZD1152 hqpa, or about 15 to about 22 weight percent of AZD1152 hqpa.

Hydrophobic Acid

In certain embodiments, disclosed nanoparticles comprise a hydrophobic acid (e.g., a bile acid) and/or are prepared by a process that includes a hydrophobic acid. Such nanoparticles may have a higher drug loading than nanoparticles prepared by a process without a hydrophobic acid. For example, drug loading (e.g., by weight) of disclosed nanoparticles prepared by a process comprising the hydrophobic acid may be between about 2 times to about 10 times higher, or even more, than disclosed nanoparticles prepared by a process without the hydrophobic acid. In some embodiments, the drug loading (by weight) of disclosed nanoparticles prepared by a first process comprising the hydrophobic acid may be at least about 2 times higher, at least about 3 times higher, at least about 4 times higher, at least about 5 times higher, or at least about 10 times higher than disclosed nanoparticles prepared by a second process, where the second process is identical to the first process except that the second process does not include the hydrophobic acid.

Any suitable hydrophobic acid is contemplated. In some embodiments, the hydrophobic acid may be a carboxylic acid (e.g., a monocarboxylic acid, dicarboxylic acid, tricarboxylic acid, or the like), a sulfinic acid, a sulfenic acid, or a sulfonic acid. In some cases, a contemplated hydrophobic acid may include a mixture of two or more acids. In some cases, a salt of a hydrophobic acid may be used in a formulation. Reference herein to "the hydrophobic acid" will be understood to apply equally to a mixture of contemplated hydrophobic acids unless the context demands otherwise.

For example, a disclosed carboxylic acid may be an aliphatic carboxylic acid (e.g., a carboxylic acid having a cyclic or acyclic, branched or unbranched, hydrocarbon chain). Disclosed carboxylic acids may, in some embodiments, be substituted with one or more functional groups including, but not limited to, halogen (F, Cl, Br, and I), sulfonyl, nitro, and oxo. In certain embodiments, a disclosed carboxylic acid may be unsubstituted.

Exemplary carboxylic acids may include a substituted or unsubstituted fatty acid (e.g., $C_6$-$C_{50}$ fatty acid). In some instances, the fatty acid may be a $C_{10}$-$C_{20}$ fatty acid. In other instances, the fatty acid may be a $C_{15}$-$C_{20}$ fatty acid. The fatty acid may, in some cases, be saturated. In other embodiments, the fatty acid may be unsaturated. For instance, the fatty acid may be a monounsaturated fatty acid or a polyunsaturated fatty acid. In some embodiments, a double bond of an unsaturated fatty acid group can be in the cis conformation. In some embodiments, a double bond of an unsaturated fatty acid can be in the trans conformation. Unsaturated fatty acids include, but are not limited to, omega-3, omega-6, and omega-9 fatty acids.

Non-limiting examples of saturated fatty acids include caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, pentacosanoic acid, cerotic acid, heptacosanoic acid, montanic acid, nonacosanoic acid, melissic acid, henatriacontanoic acid, lacceroic acid, psyllic acid, geddic acid, ceroplastic acid, hexatriacontanoic acid, and combinations thereof.

Non-limiting examples of unsaturated fatty acids include hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, oleic acid ($pK_a$=~4-5; log P=6.78), eicosenoic acid, mead acid, erucic acid, nervonic acid, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, palmitoleic acid, vaccenic acid, gadoleic acid, erucic acid, and combinations thereof.

Other non-limiting examples of hydrophobic acids include aromatic acids, such as 1-hydroxy-2-naphthoic acid (also known as xinafoic acid) ($pK_a$=~2-3; log P=2.97), naphthalene-1,5-disulfonic acid ($pK_a$=~2; log P=1.3), naphthalene-2-sulfonic acid ($pK_a$=−1.8; log P=2.1), pamoic acid ($pK_a$=2.4), cinnamic acid, phenylacetic acid, (±)-camphor-10-sulfonic acid, dodecylbenzenesulfonic acid ($pK_a$=−1.8; log P=6.6), and combinations thereof. Other non-limiting examples of hydrophobic acids include dodecylsulfuric acid ($pK_a$=−0.09; log P=4.5), dioctyl sulfosuccinic acid ($pK_a$=−0.8; log P=5.2), dioleoyl phosphatidic acid ($pK_a$=~2), and Vitamin $D_3$-sulfate ($pK_a$=−1.5).

In some embodiments, the hydrophobic acid may be a bile acid. Non-limiting examples of bile acids include chenodeoxycholic acid, ursodeoxycholic acid, deoxycholic acid ($pK_a$=4.65; log P=3.79), hycholic acid, beta-muricholic acid, cholic acid ($pK_a$=~4.5; log P=2.48), taurocholic acid, cholesteryl sulfate ($pK_a$=−1.4), lithocholic acid, an amino acid-conjugated bile acid, and combinations thereof. In some embodiments, a mixture of cholic acid and deoxycholic acid may be used. An amino-acid conjugated bile acid may be conjugated to any suitable amino acid. In some embodiments, the amino acid-conjugated bile acid is a glycine-conjugated bile acid or a taurine-conjugated bile acid.

In certain instances, the hydrophobic acid may be a polyelectrolyte. For example, the polyelectrolyte may be a polysulfonic acid (e.g., poly(styrene sulfonic acid) or dextran sulfate) or a polycarboxylic acid (e.g., polypolyacrylic acid or polymethacrylic acid).

In one aspect, the hydrophobic acid is selected from cholic acid, deoxycholic acid (including a mixture of cholic acid and deoxycholic acid), dioctylsulfosuccinic acid and pamoic acid.

In another aspect, the hydrophobic acid is pamoic acid.

In some instances, a contemplated acid may have a molecular weight of less than about 1000 Da, in some embodiments less than about 500 Da, in some embodiments less than about 400 Da, in some embodiments less than about 300 Da, in some embodiments less than about 250 Da, in some embodiments less than about 200 Da, and in some embodiments less than about 150 Da. In some cases, the acid may have a molecular weight of between about 100 Da and about 1000 Da, in some embodiments between about 200 Da and about 800 Da, in some embodiments between about 200 Da and about 600 Da, in some embodiments between about 100 Da and about 300 Da, in some embodiments between about 200 Da and about 400 Da, in some embodiments between about 300 Da and about 500 Da, and in some embodiments between about 300 Da and about 1000 Da. In certain embodiments, a contemplated acid may have a molecular weight of greater than about 300 Da, in some embodiments greater than 400 Da, and in some embodiments greater than 500 Da. In certain embodiments, the release rate of a therapeutic agent from a nanoparticle can be slowed by increasing the molecular weight of the hydrophobic acid used in the nanoparticle formulation.

In some embodiments, a hydrophobic acid may be chosen, at least in part, on the basis of the strength of the acid. For example, the hydrophobic acid may have an acid dissociation constant in water ($pK_a$) of about −5 to about 7, in some embodiments about −3 to about 5, in some embodiments about −3 to about 4, in some embodiments about −3 to about 3.5, in some embodiments about −3 to about 3, in some embodiments about −3 to about 2, in some embodiments about −3 to about 1, in some embodiments about −3 to about 0.5, in some embodiments about −0.5 to about 0.5, in some embodiments about 1 to about 7, in some embodiments about 2 to about 7, in some embodiments about 3 to about 7, in some embodiments about 4 to about 6, in some embodiments about 4 to about 5.5, in some embodiments about 4 to about 5, and in some embodiments about 4.5 to about 5, determined at 25° C. In some embodiments, the acid may have a $pK_a$ of less than about 7, less than about 5, less than about 3.5, less than about 3, less than about 2, less than about 1, or less than about 0, determined at 25° C.

In certain embodiments, the hydrophobic acid may be chosen, at least in part, on the basis of the difference between the $pK_a$ of the hydrophobic acid and the $pK_a$ of the therapeutic agent. For example, in some instances, the difference between the $pK_a$ of the hydrophobic acid and the $pK_a$ of the therapeutic agent may be between about 1 $pK_a$ unit and about 15 $pK_a$ units, in some embodiments between about 1 $pK_a$ unit and about 10 $pK_a$ units, in some embodiments between about 1 $pK_a$ unit and about 5 $pK_a$ units, in some embodiments between about 1 $pK_a$ unit and about 3 $pK_a$ units, in some embodiments between about 1 $pK_a$ unit and about 2 $pK_a$ units, in some embodiments between about 2 $pK_a$ units and about 15 $pK_a$ units, in some embodiments between about 2 $pK_a$ units and about 10 $pK_a$ units, in some embodiments between about 2 $pK_a$ units and about 5 $pK_a$ units, in some embodiments between about 2 $pK_a$ units and about 3 $pK_a$ units, in some embodiments between about 3 $pK_a$ units and about 15 $pK_a$ units, in some embodiments between about 3 $pK_a$ units and about 10 $pK_a$ units, in some embodiments between about 3 $pK_a$ units and about 5 $pK_a$ units, in some embodiments between about 4 $pK_a$ units and about 15 $pK_a$ units, in some embodiments between about 4 $pK_a$ units and about 10 $pK_a$ units, in some embodiments between about 4 $pK_a$ units and about 6 $pK_a$ units, in some embodiments between about 5 $pK_a$ units and about 15 $pK_a$ units, in some embodiments between about 5 $pK_a$ units and about 10 $pK_a$ units, in some embodiments between about 5 $pK_a$ units and about 7 $pK_a$ units, in some embodiments between about 7 $pK_a$ units and about 15 $pK_a$ units, in some embodiments between about 7 $pK_a$ units and about 9 $pK_a$ units, in some embodiments between about 9 $pK_a$ units and about 15 $pK_a$ units, in some embodiments between about 9 $pK_a$ units and about 11 $pK_a$ units, in some embodiments between about 11 $pK_a$ units and about 13 $pK_a$ units, and in some embodiments between about 13 $pK_a$ units and about 15 $pK_a$ units, determined at 25° C.

In some instances, the difference between the $pK_a$ of the hydrophobic acid and the $pK_a$ of the therapeutic agent may be at least about 1 $pK_a$ unit, in some embodiments at least about 2 $pK_a$ units, in some embodiments at least about 3 $pK_a$ units, in some embodiments at least about 4 $pK_a$ units, in some embodiments at least about 5 $pK_a$ units, in some embodiments at least about 6 $pK_a$ units, in some embodiments at least about 7 $pK_a$ units, in some embodiments at least about 8 $pK_a$ units, in some embodiments at least about 9 $pK_a$ units, in some embodiments at least about 10 $pK_a$ units, and in some embodiments at least about 15 $pK_a$ units, determined at 25° C.

In one embodiment, the difference between the pKa of the hydrophobic acid and the first pKa of AZD1152 hqpa is between 2 and 5 $pK_a$ units, determined at 25° C.

For the avoidance of doubt, pamoic acid (4,4'-methylenebis[3-hydroxy-2-naphthoic acid]) has a molecular weight of 388.37 and is reported (SciFinder) to have $pKa^1$=2.67, and log P=6.169.

In some embodiments, the hydrophobic acid may have a log P of between about 2 and about 15, in some embodiments between about 5 and about 15, in some embodiments between about 5 and about 10, in some embodiments between about 2 and about 8, in some embodiments between about 4 and about 8, in some embodiments between about 2 and about 7, or in some embodiments between about 4 and about 7. In some instances, the hydrophobic acid may have a log P greater than about 2, greater than about 4, greater than about 5, or greater than 6.

In some embodiments, a contemplated hydrophobic acid may have a phase transition temperature that is advantageous, for example, for improving the properties of the therapeutic nanoparticles. For instance, the acid may have a melting point of less than about 300° C., in some cases less than about 100° C., and in some cases less than about 50° C. In certain embodiments, the acid may have a melting point of between about 5° C. and about 25° C., in some cases between about 15° C. and about 50° C., in some cases between about 30° C. and about 100° C., in some cases between about 75° C. and about 150° C., in some cases between about 125° C. and about 200° C., in some cases between about 150° C. and about 250° C., and in some cases between about 200° C. and about 300° C. In some cases, the acid may have a melting point of less than about 15° C., in some cases less than about 10° C., or in some cases less than about 0° C. In certain embodiments, the acid may have a melting point of between about −30° C. and about 0° C. or in some cases between about −20° C. and about −10° C.

For example, an acid for use in methods and nanoparticles disclosed herein may be chosen, at least in part, on the basis of the solubility of the therapeutic agent in a solvent comprising the acid. For example, in some embodiments, the therapeutic agent dissolved in a solvent comprising the acid may have a solubility of between about 15 mg/mL to about 200 mg/mL, between about 20 mg/mL to about 200 mg/mL, between about 25 mg/mL to about 200 mg/mL, between about 50 mg/mL to about 200 mg/mL, between about 75 mg/mL to about 200 mg/mL, between about 100 mg/mL to about 200 mg/mL, between about 125 mg/mL to about 175 mg/mL, between about 15 mg/mL to about 50 mg/mL, between about 25 mg/mL to about 75 mg/mL. In some embodiments, the therapeutic agent dissolved in a solvent comprising the acid may have a solubility greater than about 10 mg/mL, greater than about 50 mg/mL, or greater than about 100 mg/mL. In some embodiments, the therapeutic agent dissolved in a solvent comprising the hydrophobic acid (e.g., a first solution consisting of the therapeutic agent, solvent, and hydrophobic acid) may have a solubility of at least about 2 times greater, in some embodiments at least about 5 times greater, in some embodiments at least about 10 times greater, in some embodiments at least about 20 times greater, in some embodiments about 2 times to about 20 times greater or in some embodiments about 10 times to about 20 times greater than when the therapeutic agent is dissolved in a solvent that does not contain the hydrophobic acid (e.g., a second solution consisting of the therapeutic agent and the solvent).

In some instances, the concentration of acid in a drug solution (the solution of therapeutic agent) may be between about 1 weight percent and about 30 weight percent, in some embodiments between about 2 weight percent and about 30 weight percent, in some embodiments between about 3 weight percent and about 30 weight percent, in some embodiments between about 4 weight percent and about 30 weight percent, in some embodiments between about 5 weight percent and about 30 weight percent, in some embodiments between about 6 weight percent and about 30 weight percent, in some embodiments between about 8 weight percent and about 30 weight percent, in some embodiments between about 10 weight percent and about 30 weight percent, in some embodiments between about 12 weight percent and about 30 weight percent, in some embodiments between about 14 weight percent and about 30 weight percent, in some embodiments between about 16 weight percent and about 30 weight percent, in some embodiments between about 1 weight percent and about 5 weight percent, in some embodiments between about 3 weight percent and about 9 weight percent, in some embodiments between about 6 weight percent and about 12 weight percent, in some embodiments between about 9 weight percent and about 15 weight percent, in some embodiments between about 12 weight percent and about 18 weight percent, and in some embodiments between about 15 weight percent and about 21 weight percent. In certain embodiments, the concentration of hydrophobic acid in a drug solution may be at least about 1 weight percent, in some embodiments at least about 2 weight percent, in some embodiments at least about 3 weight percent, in some embodiments at least about 5 weight percent, in some embodiments at least about 10 weight percent, in some embodiments at least about 15 weight percent, and in some embodiments at least about 20 weight percent.

In certain embodiments, the molar ratio of hydrophobic acid to therapeutic agent (e.g., initially during formulation of the nanoparticles and/or in the nanoparticles) may be between about 0.25:1 to about 6:1, in some embodiments between about 0.25:1 to about 5:1, in some embodiments between about 0.25:1 to about 4:1, in some embodiments between about 0.25:1 to about 3:1, in some embodiments between about 0.25:1 to about 2:1, in some embodiments between about 0.25:1 to about 1.5:1, in some embodiments between about 0.25:1 to about 1:1, in some embodiments between about 0.25:1 to about 0.5:1, in some embodiments between about 0.5:1 to about 6:1, in some embodiments between about 0.5:1 to about 5:1, in some embodiments between about 0.5:1 to about 4:1, in some embodiments between about 0.5:1 to about 3:1, in some embodiments between about 0.5:1 to about 2:1, in some embodiments between about 0.5:1 to about 1.5:1, in some embodiments between about 0.5:1 to about 1:1, in some embodiments between about 0.5:1 to about 0.75:1, in some embodiments between about 0.75:1 to about 2:1, in some embodiments between about 0.75:1 to about 1.5:1, in some embodiments between about 0.75:1 to about 1.25:1, in some embodiments between about 0.75:1 to about 1:1, in some embodiments between about 1:1 to about 6:1, in some embodiments between about 1:1 to about 5:1, in some embodiments between about 1:1 to about 4:1, in some embodiments between about 1:1 to about 3:1, in some embodiments between about 1:1 to about 2:1, in some embodiments between about 1:1 to about 1.5:1, in some embodiments between about 1.5:1 to about 6:1, in some embodiments between about 1.5:1 to about 5:1, in some embodiments between about 1.5:1 to about 4:1, in some embodiments between about 1.5:1 to about 3:1, in some embodiments between about 2:1 to about 6:1, in some embodiments between about 2:1 to about 4:1, in some embodiments between about 3:1 to about 6:1, in some embodiments between about 3:1 to about 5:1, and in some embodiments between about 4:1 to about 6:1. In some embodiments, the ratio is about 2:1.

In other embodiments the molar ratio of hydrophobic acid to AZD1152 hqpa during the formation of the nanoparticles (when they are first mixed together) is about 0.75:1 to about 1:1, for example about 0.8:1 to about 1:1. In one embodiment, the hydrophobic acid is pamoic acid and the molar ratio of pamoic acid to AZD1152 hqpa during the formation of the nanoparticles (when they are first mixed together) is about 0.75:1 to about 1:1, for example about 0.8:1 to about 1:1. This embodiment is illustrated in examples 7, 7a and 7b herein. In one embodiment, the molar ratio of pamoic acid to AZD1152 hqpa when they are first mixed together is about 0.8:1—this is illustrated in Example 7 and 7b. In one embodiment, the molar ratio of pamoic acid to AZD1152 hqpa when they are first mixed together is about 1:1—this is illustrated in Example 7a.

In some instances, the initial molar ratio of hydrophobic acid to therapeutic agent (during formulation of the nanoparticles) may be different from the molar ratio of hydrophobic acid to therapeutic agent in the nanoparticles (after removal of unencapsulated hydrophobic acid and therapeutic agent). In other instances, the initial molar ratio of hydrophobic acid to therapeutic agent (during formulation of the nanoparticles) may be essentially the same as the molar ratio of hydrophobic acid to therapeutic agent in the nanoparticles (after removal of unencapsulated hydrophobic acid and therapeutic agent). For example, in the formulations referred to herein as G1, illustrated by Examples 7 and 7b, the input molar ratio of pamoic acid to AZD1152 hqpa is about 0.8:1 but the final molar ratio in the exemplified G1 is about 0.76:1 and typical batches of formulations G1 are between about 0.65-0.75:1. Similarly the input ratio for G2 in Example 7a is about 1:1 and the final molar ratio as exemplified is about 0.87:1, with typical batches being between about 0.85-0.95:1.

In some cases, a solution containing the therapeutic agent may be prepared separately from a solution containing the polymer, and the two solutions may then be combined prior to nanoparticle formulation. For instance, in one embodiment, a first solution contains the therapeutic agent and the hydrophobic acid, and a second solution contains the polymer and optionally the hydrophobic acid. Formulations where the second solution does not contain the hydrophobic acid may be advantageous, for example, for minimizing the amount of hydrophobic acid used in a process or, in some cases, for minimizing contact time between the hydrophobic acid and, e.g., a polymer that can degrade in the presence of the hydrophobic acid. In other cases, a single solution may be prepared containing the therapeutic agent, polymer, and hydrophobic acid.

In some embodiments, a hydrophobic ion pair may be formed prior to formulation of the nanoparticles. For example, a solution containing a hydrophobic ion pair may be prepared prior to formulating the contemplated nanoparticles (e.g., by preparing a solution containing suitable amounts of the therapeutic agent and the hydrophobic acid). In other embodiments, a hydrophobic ion pair may be formed during formulation of the nanoparticles. For example, a first solution containing the therapeutic agent and a second solution containing the hydrophobic acid may be combined during a process step for preparing the nanoparticles (e.g., prior to emulsion formation and/or during emulsion formation). In certain embodiments, a hydrophobic ion pair may form prior to encapsulation of the therapeutic agent and hydrophobic acid in a contemplated nanoparticle. In other embodiments, a hydrophobic ion pair may form in the nanoparticle, e.g., after encapsulation of the therapeutic agent and hydrophobic acid.

In certain embodiments, the hydrophobic acid may have a solubility of less than about 2 g per 100 mL of water, in some embodiments less than about 1 g per 100 mL of water, in some embodiments less than about 100 mg per 100 mL of water, in some embodiments less than about 10 mg per 100 mL of water, and in some embodiments less than about 1 mg per 100 mL of water, determined at 25° C. In other embodiments, the acid may have a solubility of between about 1 mg per 100 mL of water to about 2 g per 100 mL of water, in some embodiments between about 1 mg per 100 mL of water to about 1 g per 100 mL of water, in some embodiments between about 1 mg per 100 mL of water to about 500 mg per 100 mL of water, and in some embodiments between about 1 mg per 100 mL of water to about 100 mg per 100 mL of water, determined at 25° C. In some embodiments, the hydrophobic acid may be essentially insoluble in water at 25° C.

In some embodiments, disclosed nanoparticles may be essentially free of the hydrophobic acid used during the preparation of the nanoparticles. In other embodiments, disclosed nanoparticles may comprise the hydrophobic acid. For instance, in some embodiments, the acid content in disclosed nanoparticles may be between about 0.05 weight percent to about 30 weight percent, in some embodiments between about 0.5 weight percent to about 30 weight percent, in some embodiments between about 1 weight percent to about 30 weight percent, in some embodiments between about 2 weight percent to about 30 weight percent, in some embodiments between about 3 weight percent to about 30 weight percent, in some embodiments between about 5 weight percent to about 30 weight percent, in some embodiments between about 7 weight percent to about 30 weight percent, in some embodiments between about 10 weight percent to about 30 weight percent, in some embodiments between about 15 weight percent to about 30 weight percent, in some embodiments between about 20 weight percent to about 30 weight percent, in some embodiments between about 0.05 weight percent to about 0.5 weight percent, in some embodiments between about 0.05 weight percent to about 5 weight percent, in some embodiments between about 1 weight percent to about 5 weight percent, in some embodiments between about 3 weight percent to about 10 weight percent, in some embodiments between about 5 weight percent to about 15 weight percent, and in some embodiments between about 10 weight percent to about 20 weight percent.

Release Profile

In some embodiments, disclosed nanoparticles substantially immediately release (e.g., over about 1 minute to about 30 minutes, about 1 minute to about 25 minutes, about 5 minutes to about 30 minutes, about 5 minutes to about 1 hour, about 1 hour, or about 24 hours) less than about 2%, less than about 5%, less than about 10%, less than about 15%, less than about 20%, less than about 25%, less than about 30%, or less than 40% of the therapeutic agent, for example when placed in a phosphate buffer solution at room temperature (e.g., 25° C.) and/or at 37° C. In certain embodiments, nanoparticles comprising the therapeutic agent may release the therapeutic agent when placed in an aqueous solution (e.g., a phosphate buffer solution), e.g., at 25° C. and/or at 37° C., at a rate substantially corresponding to about 0.01 to about 50%, in some embodiments about 0.01 to about 25%, in some embodiments about 0.01 to about 15%, in some embodiments about 0.01 to about 10%, in some embodiments about 1 to about 40%, in some embodiments about 5 to about 40%, and in some embodiments about 10 to about 40% of the therapeutic agent released over about 1 hour. In some embodiments, nanoparticles comprising the therapeutic agent may release the therapeutic agent when placed in an aqueous solution (e.g., a phosphate buffer solution), e.g., at 25° C. and/or at 37° C., at a rate substantially corresponding to about 10 to about 70%, in some embodiments about 10 to about 45%, in some embodiments about 10 to about 35%, or in some embodiments about 10 to about 25%, of the therapeutic agent released over about 4 hours.

In some embodiments, disclosed nanoparticles may substantially retain the therapeutic agent, e.g., for at least about 1 minute, at least about 1 hour, or more, when placed in a phosphate buffer solution at 37° C.

In some embodiments, a contemplated therapeutic nanoparticle substantially retains the AZD1152 hqpa for at least 1 minute when placed in a phosphate buffer solution at 37° C.

In some embodiments, a contemplated therapeutic nanoparticle substantially immediately releases less than about 30% of the AZD1152 hqpa when placed in a phosphate buffer solution at 37° C.

In some embodiments, a contemplated therapeutic nanoparticle releases about 10 to about 45% of the AZD1152 hqpa over about 1 hour when placed in a phosphate buffer solution at 37° C.

In-vitro release profiles for the contemplated nanoparticles may be measured as follows:

The release was calculated by dividing the amount of AZD1152 hqpa released from the nanoparticle into the release medium by the amount of total AZD1152 hqpa. In order to obtain these two values, a specified amount of nanoparticle was spiked into a closed container containing release medium (phosphate buffer solution (PBS) containing polysorbate20 to ensure sink conditions) and incubated in a 37° C. water bath. At each set time point, two samples were taken. The first, used to give the total AZD1152 hqpa value, was taken from the the container and prepared for HPLC. The second sample, used to give the released AZD1152 hqpa at the time point, was taken and pelleted in an ultracentrifuge leaving only released AZD1152 hqpa in the suspension (or supernatant) which was then sampled and prepared for HPLC. A suitable HPLC method is given in Example 10.

Nine batches of each formulations G1 and G2 were tested, with quantitative compositions similar to those shown in Example 7-7b, and in particular with G1 formulations having a pamoic acid: AZD1152 hqpa molar ratio in the range of about 0.65-0.75:1, and G2 formulations having a molar ratio of about 0.85-0.95:1. The data below show the mean release values over 72 hours.

37° C. In Vitro Release Profiles

|  | 0 | 4 | 24 | 48 | 72 | Time (hr) |
|---|---|---|---|---|---|---|
| Formulation G1 | | | | | | |
| G1 Mean release | 0.808 | 3.182 | 7.708 | 13.808 | 23.075 | % |
| One Standard Deviation | 0.327 | 0.696 | 1.259 | 2.436 | 3.390 | % |
| Formulation G2 | | | | | | |
| G2 Mean release | 1.558 | 13.713 | 32.107 | 50.637 | 67.257 | % |
| One Standard Deviation | 0.816 | 9.481 | 12.896 | 9.916 | 7.720 | % |

In one aspect, a contemplated therapeutic nanoparticle comprising 16-5 PLA-PEG co-polymer, pamoic acid and AZD1152 hqpa releases less than 20% of AZD1152 hqpa after 30 hours in PBS and polysorbate20 at 37° C. In another aspect a contemplated therapeutic nanoparticle comprising 16-5 PLA-PEG co-polymer, pamoic acid and AZD1152 hqpa releases less than 20% of AZD1152 hqpa after 40 hours in PBS and polysorbate20 at 37° C. In another aspect, a contemplated therapeutic nanoparticle comprising 16-5 PLA-PEG co-polymer, pamoic acid and AZD1152 hqpa releases less than 20% of AZD1152 hqpa after 50 hours in PBS and polysorbate20 at 37° C. In another aspect, a contemplated therapeutic nanoparticle comprising 16-5 PLA-PEG co-polymer, pamoic acid and AZD1152 hqpa releases about 10% of AZD1152 hqpa after 24 hours in PBS and polysorbate20 at 37° C. In these aspects, conveniently the release is measured by the above method.

In one aspect (for example when the therapeutic nanoparticles comprise deoxycholic acid, cholic acid (including a mixture of deoxycholic acid and cholic acid), dioctyl sulfosuccinic acid or pamoic acid), the therapeutic nanoparticles release the AZD1152 hqpa in vivo at a rate such that less than 40% has been released 24 hours after dosing. In another aspect (for example when the therapeutic nanoparticles comprise deoxycholic acid, cholic acid (including a mixture of deoxycholic acid and cholic acid), dioctyl sulfosuccinic acid or pamoic acid), the therapeutic nanoparticles release the AZD1152 hqpa in vivo at a rate such that less than 30% has been released 24 hours after dosing. In one aspect (for example when the therapeutic nanoparticles comprise deoxycholic acid, cholic acid (including a mixture of deoxycholic acid and cholic acid, dioctyl sulfosuccinic acid or pamoic acid), the therapeutic nanoparticles release the AZD1152 hqpa in vivo at a rate of such that 25-35% has been released 24 hours after dosing. In another aspect (for example when the therapeutic nanoparticles comprise pamoic acid), the therapeutic nanoparticles release the AZD1152 hqpa in vivo at a rate such that less than 15% has been released 24 hours after dosing.

In general, a "nanoparticle" refers to any particle having a diameter of less than 1000 nm, e.g., about 10 nm to about 200 nm. Disclosed therapeutic nanoparticles may include nanoparticles having a diameter of about 60 to about 120 nm, or about 70 to about 120 nm, or about 80 to about 120 nm, or about 90 to about 120 nm, or about 100 to about 120 nm, or about 60 to about 130 nm, or about 70 to about 130 nm, or about 80 to about 130 nm, or about 90 to about 130 nm, or about 100 to about 130 nm, or about 110 to about 130 nm, or about 60 to about 140 nm, or about 70 to about 140 nm, or about 80 to about 140 nm, or about 90 to about 140 nm, or about 100 to about 140 nm, or about 110 to about 140 nm, or about 60 to about 150 nm, or about 70 to about 150 nm, or about 80 to about 150 nm, or about 90 to about 150 nm, or about 100 to about 150 nm, or about 110 to about 150 nm, or about 120 to about 150 nm.

In some embodiments, the hydrodynamic diameter of a contemplated therapeutic nanoparticle is about 60 to about 150 nm, or about 90 to about 140 nm, or about 90 to about 120 nm. In a further aspect, the hydrodynamic diameter of a contemplated therapeutic nanoparticle is about 90 to about 110 nm, for example when the therapeutic nanoparticles comprise a substantially hydrophobic acid selected from deoxycholic acid, cholic acid, dioctyl sulfosuccinic acid, pamoic acid, or mixtures thereof.

In one embodiment, the disclosed nanoparticles are formed with AZD1152 hqpa and pamoic acid, and have a hydrodynamic diameter of <500 nm, such as <200 nm, for example 70-140 nm.

In particular, the disclosed nanoparticles are formed with AZD1152 hqpa and a hydrophobic acid selected from cholic acid, deoxycholic acid and dioctyl sulfosuccinic acid. In another embodiment, the disclosed nanoparticles are formed with AZD1152 hqpa and a hydrophobic acid selected from deoxycholic acid and dioctyl sulfosuccinic acid. In one aspect the disclosed nanoparticles are formed with AZD1152 hqpa and deoxycholic acid. In another aspect the disclosed nanoparticles are formed with AZD1152 hqpa and dioctyl sulfosuccinic acid. In another aspect the disclosed nanoparticles are formed with AZD1152 and cholic acid. In one aspect the disclosed nanoparticles are formed with AZD1152 hqpa and a mixture of cholic acid and deoxycholic acid; in this aspect, suitably the hydrophobic acids are in a ratio of about 3:2 deoxycholic acid:cholic acid and the ratio of total hydrophobic acid: AZD1152 hqpa is about 2:1 (wherein ratios are expressed by weight percent). In another aspect, the disclosed nanoparticles are formed with AZD1152 hqpa and pamoic acid.

Polymers

In some embodiments, the nanoparticles may comprise a matrix of polymers and the therapeutic agent. In some embodiments, the therapeutic agent can be associated with at least part of the polymeric matrix. The therapeutic agent can be associated with the surface of, encapsulated within, surrounded by, and/or dispersed throughout the polymeric matrix.

Any suitable polymer can be used in the disclosed nanoparticles. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers are organic polymers.

The term "polymer," as used herein, is given its ordinary meaning as used in the art, that is, a molecular structure comprising one or more repeat units (monomers), connected by covalent bonds. The repeat units may all be identical, or in some cases, there may be more than one type of repeat unit present within the polymer. In some cases, the polymer can be biologically derived (a biopolymer). Non-limiting examples include peptides or proteins. In some cases, additional moieties may also be present in the polymer, for example biological moieties such as those described below.

If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (for example a copolymer or a block copolymer) can be amphiphilic, that is, having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, a hydrophilic polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (such as a copolymer or a block copolymer) contemplated herein includes a biocompatible polymer, which is a polymer that does not typically induce an adverse response when inserted or injected into a living subject, for example, without significant inflammation and/or acute rejection of the polymer by the immune system, for instance through a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system—a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments include polydioxanone (PDO), polyhydroxyalkanoate, polyhydroxybutyrate, poly(glycerol sebacate), polyglycolide (poly(glycolic) acid) (PGA), polylactide (poly(lactic) acid) (PLA), poly(lactic) acid-co-poly(glycolic) acid (PLGA), polycaprolactone, or copolymers or derivatives including these and/or other polymers.

In certain embodiments, contemplated biocompatible polymers may be biodegradable, so that the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R bonds). In some embodiments, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

For instance, a contemplated polymer may be one that hydrolyzes spontaneously upon exposure to water (e.g., within a subject), or the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof). In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester).

It is contemplated that PEG may be terminated and include an end group. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In one embodiment, the molecular weight (or e.g., the ratio of molecular weights of, e.g., different blocks of a copolymer) of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer (or e.g., the ratio of molecular weights of, e.g., different blocks of a copolymer) can be adjusted such that the particle biodegrades in the subject being treated within a reasonable period of time (ranging from a few hours to 1-2 weeks, 3-4 weeks, 5-6 weeks, 7-8 weeks, etc.).

A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

For example, disclosed here is an exemplary therapeutic nanoparticle that includes about 10 to about 99 weight percent poly(lactic) acid-poly(ethylene)glycol copolymer or poly(lactic)-co-poly (glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly (glycolic) acid-poly(ethylene)glycol copolymer. Exemplary poly(lactic) acid-poly(ethylene)glycol copolymers can include a number average molecular weight of about 15 to about 20 kDa, or about 10 to about 25 kDa of poly(lactic) acid and a number average molecular weight of about 4 kDa to about 6 kDa, or about 2 kDa to about 10 kDa of poly(ethylene)glycol.

In some embodiments, the poly(lactic) acid-poly(ethylene)glycol copolymer may have a poly(lactic) acid number average molecular weight fraction of about 0.6 to about 0.95, in some embodiments between about 0.7 to about 0.9, in some embodiments between about 0.6 to about 0.8, in some embodiments between about 0.7 to about 0.8, in some embodiments between about 0.75 to about 0.85, in some embodiments between about 0.8 to about 0.9, and in some embodiments between about 0.85 to about 0.95. It should be understood that the poly(lactic) acid number average molecular weight fraction may be calculated by dividing the number average molecular weight of the poly(lactic) acid component of the copolymer by the sum of the number average molecular weight of the poly(lactic) acid component and the number average molecular weight of the poly (ethylene)glycol component.

Disclosed nanoparticles may optionally include about 1 to about 50 weight percent poly(lactic) acid or poly(lactic)

acid-co-poly (glycolic) acid (which does not include PEG), or may optionally include about 1 to about 50 weight percent, or about 10 to about 50 weight percent or about 30 to about 50 weight percent poly(lactic) acid or poly(lactic) acid-co-poly (glycolic) acid. For example, poly(lactic) or poly(lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

A therapeutic nanoparticle may, in some embodiments, contain about 10 to about 30 weight percent, in some embodiments about 10 to about 25 weight percent, in some embodiments about 10 to about 20 weight percent, in some embodiments about 10 to about 15 weight percent, in some embodiments about 15 to about 20 weight percent, in some embodiments about 15 to about 25 weight percent, in some embodiments about 20 to about 25 weight percent, in some embodiments about 20 to about 30 weight percent, or in some embodiments about 25 to about 30 weight percent of poly(ethylene)glycol, where the poly(ethylene)glycol may be present as a poly(lactic) acid-poly(ethylene)glycol copolymer, poly(lactic)-co-poly (glycolic) acid-poly(ethylene) glycol copolymer, or poly(ethylene)glycol homopolymer. In certain embodiments, the polymers of the nanoparticles can be conjugated to a lipid. The polymer can be, for example, a lipid-terminated PEG.

In one embodiment, the therapeutic nanoparticles contain about 50 to about 99.75 weight percent of a diblock poly (lactic) acid-poly(ethylene)glycol copolymer or a diblock poly(lactic acid-co-glycolic acid)-poly(ethylene)glycol copolymer, wherein the therapeutic nanoparticle comprises about 10 to about 30 weight percent poly(ethylene)glycol; and about 0.2 to about 30 weight percent of AZD1152 hqpa. In one aspect the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol; for example the poly(lactic) acid-poly (ethylene)glycol copolymer has a number average molecular weight of about 16 kDa poly(lactic acid) and a number average molecular weight of about 5 kDa poly(ethylene) glycol.

In another embodiment, the therapeutic nanoparticles contain about 50 to about 99.75 weight percent of a diblock poly(lactic) acid-poly(ethylene)glycol copolymer wherein the therapeutic nanoparticle comprises about 10 to about 30 weight percent poly(ethylene)glycol; and about 0.2 to about 30 weight percent of AZD1152 hqpa. In one aspect the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol; for example the poly(lactic) acid-poly(ethylene)glycol copolymer has a number average molecular weight of about 16 kDa poly(lactic acid) and a number average molecular weight of about 5 kDa poly(ethylene)glycol.

In another embodiment, the therapeutic nanoparticles contain about 50 to about 99 weight percent of a diblock poly(lactic) acid-poly(ethylene)glycol copolymer wherein the therapeutic nanoparticle comprises about 10 to about 30 weight percent poly(ethylene)glycol; and about 1 to about 30 weight percent of AZD1152 hqpa. In one aspect the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol; for example the poly(lactic) acid-poly(ethylene)glycol copolymer has a number average molecular weight of about 16 kDa poly(lactic acid) and a number average molecular weight of about 5 kDa poly(ethylene)glycol.

In one aspect, the poly(lactic) acid-poly(ethylene)glycol copolymer has a poly(lactic) acid number average molecular weight fraction of about 0.7 to about 0.9, such as about 0.75 to about 0.85.

In one aspect the therapeutic nanoparticle comprises about 10 to about 25 weight percent poly(ethylene)glycol. In a further aspect, the therapeutic nanoparticle comprises about 20 to about 30 weight percent poly(ethylene)glycol.

In a further aspect, the therapeutic nanoparticle comprises about 65 weight percent to about 85 weight percent of the copolymer, for example about 65 weight percent to about 80 weight percent copolymer.

In a further aspect, when the hydrophobic acid is pamoic acid, the therapeutic nanoparticle comprises about 60 to about 80 percent copolymer (particularly PLA-PEG co-polymer, particularly 16/5 PLA-PEG co-polymer), such as about 65 to about 75 percent copolymer, wherein the poly (ethylene)glycol content is about 15 to about 20 percent by weight of the nanoparticle. It will be understood by the skilled person however, that the weight percent of polymers present in the nanoparticle will vary to some extent between batches as the amount of hydrophobic acid (such as pamoic acid) and AZD1152 hqpa varies.

Preparation of Nanoparticles

Another aspect of this disclosure is directed to systems and methods of making disclosed nanoparticles. In some embodiments, using two or more different polymers (e.g., copolymers, e.g., block copolymers) in different ratios and producing particles from the polymers (e.g., copolymers, e.g., block copolymers), properties of the particles be controlled. For example, a polymer (e.g., copolymer, e.g., block copolymer) may be chosen for its biocompatibility and/or its ability to control immunogenicity of the resultant particle.

In some embodiments, a solvent used in a nanoparticle preparation process (e.g., a nanoprecipitation process or a nanoemulsion process as discussed below) may include a hydrophobic acid, which may confer advantageous properties to the nanoparticles prepared using the process. As discussed above, in some cases, the hydrophobic acid may improve drug loading of disclosed nanoparticles. Furthermore, in some instances, the controlled release properties of disclosed nanoparticles may be improved by the use of the hydrophobic acid. In some cases, the hydrophobic acid may be included in, for example, an organic solution or an aqueous solution used in the process. In one embodiment, the hydrophobic acid is incorporated in an aqueous solution in the form of a water-soluble salt (such as a sodium salt), for example as sodium cholate. In one embodiment, the drug is combined with an organic solution and the hydrophobic acid and optionally one or more polymers. The hydrophobic acid concentration in a solution used to dissolve the drug is discussed above and may be, for example, between about 1 weight percent and about 30 weight percent, etc.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethylsulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution is poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Properties such as surface functionality, surface charge, size, zeta (ζ) potential, hydrophobicity, ability to control immunogenicity, and the like, may be highly controlled using a disclosed process. For instance, a library of particles may be synthesized, and screened to identify the particles having a particular ratio of polymers that allows the particles to have a specific density of moieties present on the surface of the particle. This allows particles having one or more specific properties to be prepared, for example, a specific size and a specific surface density of moieties, without an undue degree of effort. Accordingly, certain embodiments are directed to screening techniques using such libraries, as well as any particles identified using such libraries. In addition, identification may occur by any suitable method. For instance, the identification may be direct or indirect, or proceed quantitatively or qualitatively.

Figure 2A:
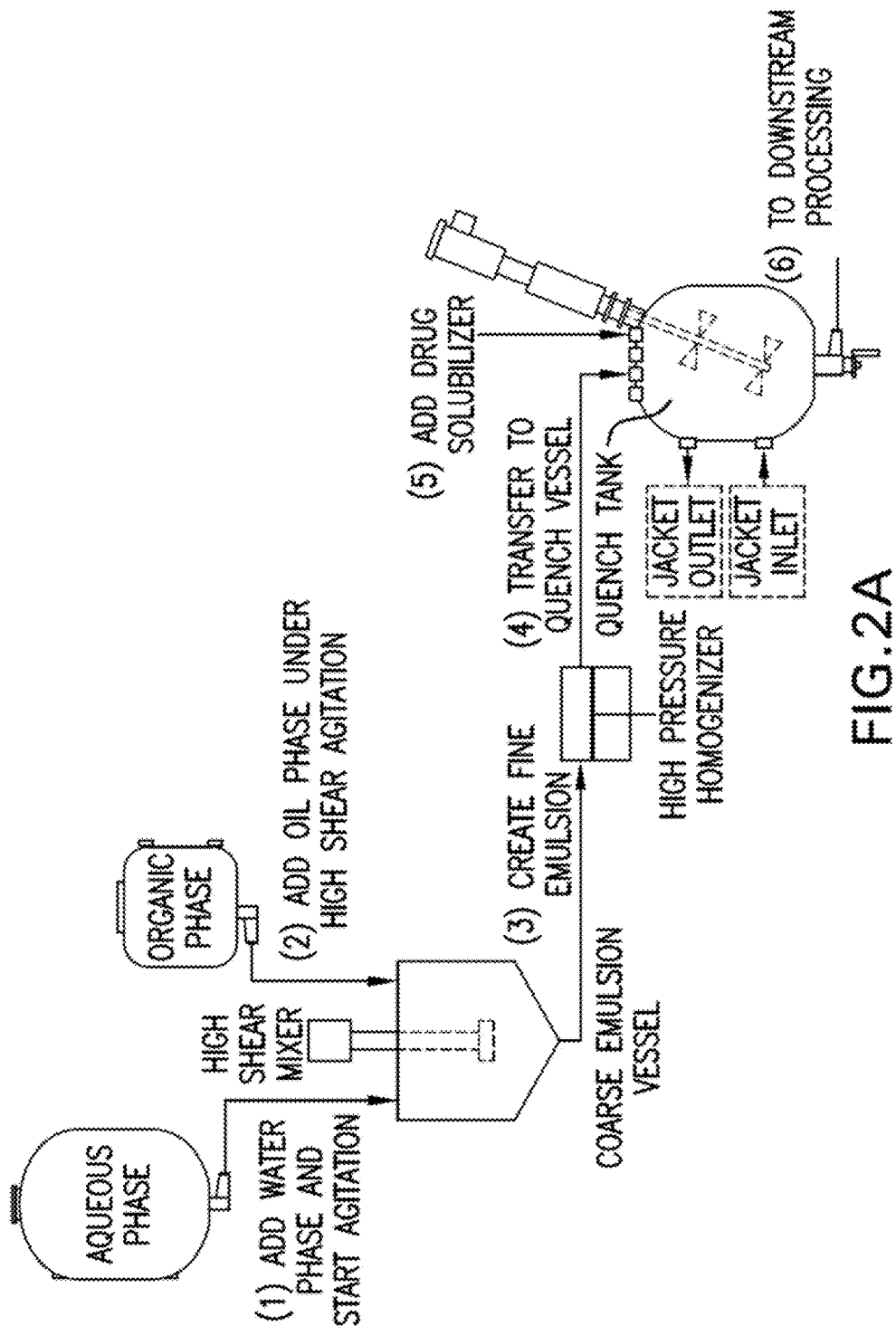
FIGS. 2A and 2B show flow diagrams for a disclosed emulsion process.
Figure 2B:
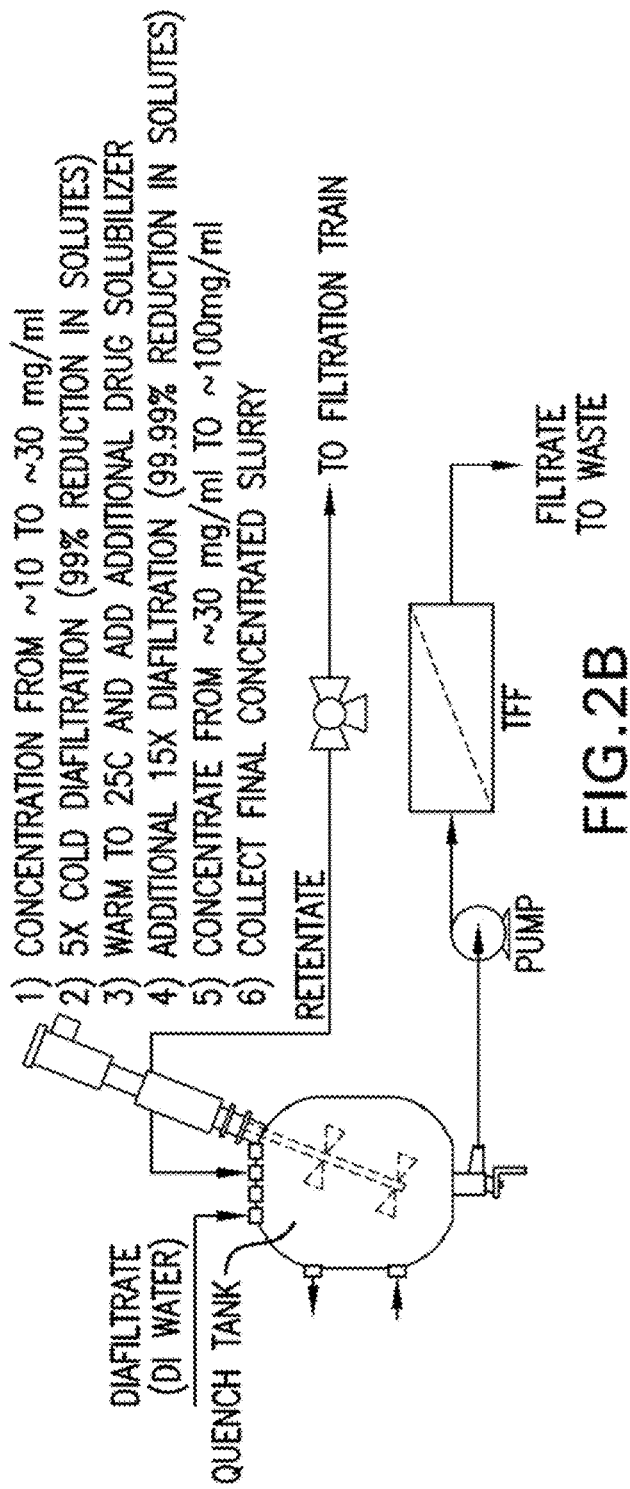

In another embodiment, a nanoemulsion process is provided, such as the process represented in FIGS. 1, 2A, and 2B. For example, the therapeutic agent, a hydrophobic acid, a first polymer (for example, a diblock co-polymer such as PLA-PEG or PLGA-PEG) and an optional second polymer (e.g., (PL(G)A-PEG or PLA), may be combined with an organic solution to form a first organic phase. Such first phase may include about 1 to about 50 weight % solids, about 5 to about 50 weight % solids, about 5 to about 40 weight % solids, about 1 to about 15 weight % solids, or about 10 to about 30 weight % solids. The first organic phase may be combined with a first aqueous solution to form a second phase. The organic solution can include, for example, toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, polysorbate 80 sold under the trademark Tween®80, sorbitane monooleate sold under the trademark Span® 80, polyoxethylene (100) stearyl ether sold under the trademark Brij® 100 or the like, and combinations thereof. The organic solution may also include dimethylsulfoxide (DMSO). In an embodiment, the organic phase may include benzyl alcohol, ethyl acetate, and combinations thereof. In another embodiment, the organic phase may include benzyl alcohol, ethyl acetate and DMSO. The second phase can be between about 0.1 and 50 weight %, between about 1 and 50 weight %, between about 5 and 40 weight %, or between about 1 and 15 weight % solids. The aqueous solution can be water, optionally in combination with one or more of sodium cholate, sodium docusate, ethyl acetate, polyvinyl acetate and benzyl alcohol. The aqueous solution may also contain DMSO and/or polyoxethylene (100) stearyl ether sold under the trademark Brij® 100 or similar. In some embodiments, the aqueous solution comprises polyoxethylene (100) stearyl ether sold under the trademark Brij® 100, benzyl alcohol and DMSO in water. In some embodiments, the pH of the aqueous phase may be selected based on the $pK_a$ of the protonated therapeutic agent and/or the $pK_a$ of the hydrophobic acid. For example, in certain embodiments, the therapeutic agent, when protonated, may have a first $pK_a$, the hydrophobic acid may have a second $pK_a$, and the aqueous phase may have a pH equal to a $pK_a$ unit between the first $pK_a$ and the second $pK_a$. In a particular embodiment, the pH of the aqueous phase may be equal to a $pK_a$ unit that is about equidistant between the the first $pK_a$ and the second $pK_a$.

For example, the oil or organic phase may use a solvent that is only partially miscible with the nonsolvent (water). Therefore, when mixed at a low enough ratio and/or when using water pre-saturated with the organic solvents, the organic (oil) phase remains liquid. The organic (oil) phase may be emulsified into an aqueous solution and, as liquid droplets, sheared into nanoparticles using, for example, high energy dispersion systems, such as homogenizers or sonicators. The aqueous portion of the emulsion, otherwise known as the "water phase", may be surfactant solution consisting of sodium cholate (or possibly sodium docusate) and pre-saturated with ethyl acetate and benzyl alcohol. In some instances, the organic phase (e.g., first organic phase) may include the therapeutic agent. Additionally, in certain embodiments, the aqueous solution (e.g., first aqueous solution) may include the substantially hydrophobic acid. In other embodiments, both the therapeutic agent and the substantially hydrophobic acid may be dissolved in the organic phase.

Emulsifying the second phase to form an emulsion phase may be performed, for example, in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g., probe sonicator or a high pressure homogenizer for example by using 1, 2, 3, or more passes through a homogenizer. For example, when a high pressure homogenizer is used, the pressure used may be about 30 to about 60 psi, about 40 to about 50 psi, about 1000 to about 8000 psi, about 2000 to about 4000 psi, about 4000 to about 8000 psi, or about 4000 to about 5000 psi, e.g., about 2000, 2500, 4000 or 5000 psi. The pressure used may be about 5,000 to 20,000 psi, such 5,000 to 15,000 psi, such as about 8,000 to 15,000 psi, for example 8,000 to about 12,000 psi. The processes exemplified herein use about 9,000 psi (see Examples 7, 7a and 7b) and about 11,000 psi (such as Example 1).

In some cases, fine emulsion conditions, which can be characterized by a very high surface to volume ratio of the droplets in the emulsion, can be chosen to maximize the solubility of the therapeutic agent and hydrophobic acid and form the desired HIP. In certain embodiments, under fine emulsion conditions, equilibration of dissolved components can occur very quickly, and faster than solidification of the nanoparticles. Thus, selecting a HIP based on, e.g., the $pK_a$ difference between the therapeutic agent and the hydrophobic acid, or adjusting other parameters such as the pH of the fine emulsion and/or the pH of the quench solution, can have a significant impact on the drug loading and release properties of the nanoparticles by dictating, for example, the formation of a HIP in the nanoparticle as opposed to diffusion of the therapeutic agent and/or hydrophobic acid out of the nanoparticle.

In some embodiments, the therapeutic agent and the substantially hydrophobic acid may be combined in the second phase prior to emulsifying the second phase. In some instances, the therapeutic agent and the substantially hydrophobic acid may form a hydrophobic ion pair prior to emulsifying the second phase. In other embodiments, the therapeutic agent and the substantially hydrophobic acid may form a hydrophobic ion pair during emulsification of the second phase. For example, the therapeutic agent and the substantially hydrophobic acid may be combined in the second phase substantially concurrently with emulsifying the second phase, e.g., the therapeutic agent and the substantially hydrophobic acid may be dissolved in separate solutions (e.g., two substantially immiscible solutions), which are then combined during emulsification. In another example, the therapeutic agent and the substantially hydrophobic acid may be dissolved in separate miscible solutions that are then fed into second phase during emulsification.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. In some embodiments, quenching may be performed at least partially at a temperature of about 5° C. or less. For example, water (or other quench solution) used in the quenching may be at a temperature that is less than room temperature (e.g., about 0 to about 10° C., or about 0 to about 5° C.). The solutions may also be cooled during quenching. In certain embodiments, the quench may be chosen having a pH that is advantageous for quenching the emulsion phase, e.g., by improving the properties of the nanoparticles, such as the release profile, or improving a nanoparticle parameter, such as the drug loading. The pH of the quench may be adjusted by acid or base titration, for example, or by appropriate selection of a buffer.

In some embodiments, the pH of the quench may be selected based on the $pK_a$ of the protonoated therapeutic agent and/or the $pK_a$ of the hydrophobic acid. For example, in certain embodiments, the therapeutic agent, when protonated, may have a first $pK_a$, the hydrophobic acid may have a second $pK_a$, and the emulsion phase may be quenched with an aqueous solution having a pH equal to a $pK_a$ unit between the first $pK_a$ and the second $pK_a$. In some embodiments, the resultant quenched phase may also have a pH equal to a $pK_a$ unit between the first $pK_a$ and the second $pK_a$. In a particular embodiment, the pH may be equal to a $pK_a$ unit that is about equidistant between the the first $pK_a$ and the second $pK_a$.

In some embodiments, the quench may have a pH between about 2 and about 12, in some embodiments between about 3 and about 10, in some embodiments between about 3 and about 9, in some embodiments between about 3 and about 8, in some embodiments between about 3 and about 7, in some embodiments between about 4 and about 8, in some embodiments between about 4 and about 7, in some embodiments between about 4 and about 6, in some embodiments between about 4 and about 5, in some embodiments between about 4.2 and about 4.8, in some embodiments between about 6 and about 10, in some embodiments between about 6 and about 9, in some embodiments between about 6 and about 8, in some embodiments between about 6 and about 7. In certain embodiments, the quench may have a pH of about 4.5. In further embodiments, the quench may have a pH of about 6.5. It should be understood that the pH of a buffer solution may vary as a function of temperature. Unless otherwise specified, the pH of a buffer solution referred to herein is the pH at 23° C.

In some embodiments, the quench may be an aqueous solution comprising a buffering agent (a buffer solution). Any suitable buffering agent may be used. Non-limiting examples of buffering agents include phosphate, citrate, acetate, borate, imidazole, MES (4-morpholineethanesulfonic acid), bis-tris (Bis(2-hydroxyethyl)amino-tris(hydroxymethyl)methane), ADA (N-(2-Acetamido)iminodiacetic acid), ACES (N-(2-Acetamido)-2-aminoethanesulfonic acid), PIPES (1,4-Piperazinediethanesulfonic acid), MOPSO (3-Morpholino-2-hydroxypropanesulfonic acid), bis-tris propane (1,3-Bis[tris(hydroxymethyl)methylamino]propane), BES (N,N-Bis(2-hydroxyethyl)-2-aminoethanesulfonic acid), MOPS (3-(N-Morpholino)propanesulfonic acid), TES (2-[(2-Hydroxy-1,1-bis(hydroxymethyl)ethyl)amino]ethanesulfonic acid), HEPES (4-(2-Hydroxyethyl)piperazine-1-ethanesulfonic acid), DIPSO (3-(N,N-Bis[2-hydroxyethyl]amino)-2-hydroxypropanesulfonic acid), MOBS (4-(N-Morpholino)butanesulfonic acid), TAPSO (2-Hydroxy-3-[tris(hydroxymethyl)methylamino]-1-propanesulfonic acid), Trizma (2-Amino-2-(hydroxymethyl)-1,3-propanediol), HEPPSO (4-(2-Hydroxyethyl)piperazine-1-(2-hydroxypropanesulfonic acid)), POPSO (Piperazine-N,N'-bis(2-hydroxypropanesulfonic acid)), TEA (triethylamine), EPPS (4-(2-Hydroxyethyl)-1-piperazinepropanesulfonic acid), tricine (N-[Tris(hydroxymethyl)methyl]glycine), Gly-Gly (Diglycine), bicine (N,N-Bis(2-hydroxyethyl)glycine), HEPBS (N-(2-Hydroxyethyl)piperazine-N'-(4-butanesulfonic acid)), TAPS (N-[Tris(hydroxymethyl)methyl]-3-aminopropanesulfonic acid), AMPD (2-Amino-2-methyl-1,3-propanediol), TABS (N-tris(Hydroxymethyl)methyl-4-aminobutanesulfonic acid), AMPSO (N-(1,1-Dimethyl-2-hydroxyethyl)-3-amino-2-hydroxypropanesulfonic acid), CHES (2-(Cyclohexylamino)ethanesulfonic acid), CAPSO (3-(Cyclohexylamino)-2-hydroxy-1-propanesulfonic acid), AMP (β-Aminoisobutyl alcohol), CAPS (3-(Cyclohexylamino)-1-propanesulfonic acid), CABS (4-(Cyclohexylamino)-1-butanesulfonic acid), and combinations thereof. It should be understood that a buffer comprises an acid and a base in equilibrium (e.g., an acid and a conjugate base and/or a base and a conjugate acid). Thus, it should further be understood that, for brevity, a buffer solution or buffering agent may be referred to herein by the name of a free acid (e.g., phosphoric acid) or its conjugate base (e.g., phosphate), or the name of a free base (e.g., imidazole) or its conjugate acid (e.g., imidazolium), but that one of ordinary skill in the art would understand that an equilibrium exists between two or more different protonation species of the buffering agent (e.g., $H_3PO_4$, $H_2PO_4^-$, $HPO_4^{2-}$, and $PO_4^{3-}$). In some embodiments, the quench may comprise two or more buffering agents. For example, the quench may comprise two, three, four, or five buffering agents. In some embodiments, the quench may comprise a mixture of phosphate and citrate. In other embodiments, the quench may comprise a mixture of borate, phosphate, and acetate (e.g., Britton-Robbinson buffer, which comprises 0.04 M $H_3BO_3$, 0.04 M $H_3PO_4$, and 0.04 M $CH_3COOH$ titrated to a desired pH).

In some embodiments, a buffer solution (a quench) may have a suitable buffering capacity within a particular pH range. Non-limiting pH ranges for exemplary buffer solutions are provided in Table A below. In certain embodiments, a buffer solution may have a buffering agent concentration between about 0.001M and about 1M, in some embodiments between about 0.001M and about 0.5M, in some embodiments between about 0.01M and about 0.5M, in some embodiments between about 0.05M and about 0.5M, in some embodiments between about 0.1M and about 0.5M, in some embodiments between about 0.01M and about 0.2M, in some embodiments between about 0.05M and about 0.15M, and in some embodiments between about 0.075M and about 0.125M.

TABLE A

Non-limiting pH ranges for exemplary buffers.

| Buffering agent | pH range |
| --- | --- |
| Phosphate | 5.7-8.0 |
| Citrate | 3.0-6.2 |
| Phosphate-Citrate | 2.6-7.6 |
| Acetate | 3.7-5.6 |
| Imidazole | 6.2-7.8 |
| Britton-Robbinson | 2-12 |
| ADA | 6.0-7.2 |
| ACES | 6.1-7.5 |
| PIPES | 6.1-7.5 |
| MOPSO | 6.2-7.6 |
| Bis-tris Propane | 6.3-9.5 |
| BES | 6.4-7.8 |
| MOPS | 6.5-7.9 |
| TES | 6.8-8.2 |
| HEPES | 6.8-8.2 |
| DIPSO | 7.0-8.2 |
| MOBS | 6.9-8.3 |

In some embodiments, a quench may have a buffering agent concentration sufficient to resist a substantial pH change. For example, a quenched phase may have a pH that differs from the pH of the emulsion phase by less than 1 pH unit, in some embodiments less than 0.5 pH units, in some embodiments, less than 0.2 pH units, in some embodiments less than 0.1 pH units, and in some embodiments less than 0.05 pH units. In some embodiments, the pH of the quenched phase may be substantially the same as the pH of the emulsion phase (prior to quenching).

In some embodiments, the quenched phase may have a pH between about 2 and about 12, in some embodiments between about 3 and about 10, in some embodiments between about 3 and about 9, in some embodiments between about 3 and about 8, in some embodiments between about 3 and about 7, in some embodiments between about 4 and about 8, in some embodiments between about 4 and about 7, in some embodiments between about 4 and about 6, in some embodiments between about 4 and about 5, in some embodiments between about 4.2 and about 4.8, in some embodiments between about 6 and about 10, in some embodiments between about 6 and about 9, in some embodiments between about 6 and about 8, in some embodiments between about 6 and about 7. In certain embodiments, the quenched phase may have a pH of about 4.6.

A buffering solution (e.g., a quench) at a desired pH can be readily prepared by one of ordinary skill in the art. For example, a buffering solution at a desired pH can prepared by titrating a solution containing a buffering agent with a strong acid (e.g., HCl) or strong base (e.g., NaOH). Alternatively, a buffering solution at a desired pH can prepared by combining a weak acid (e.g., citric acid) with its conjugate base (e.g., sodium citrate) or by combining a weak base (e.g., imidazole) with its conjugate acid (e.g., imidazolium chloride). One of ordinary skill in the art could determine the amounts of the weak acid or weak base and corresponding conjugate to use in preparing a buffering solution by using the Henderson-Hasselbalch equation.

In one aspect, the quench solution is a buffer solution at pH 6.5 (such as 0.17M sodium phosphate buffer). Conveniently, the quench solution is cooled to <5° C. before the emulsion is added to it. Conveniently, the mixture of quench and emulsion solutions are cooled while they are mixed together. In one embodiment, the ratio of quench solution to emulsion is 10:1 (by weight). In another embodiment, the ratio of quench solution to emulsion is 3:1. In this aspect and embodiments, conveniently the hydrophobic acid is pamoic acid.

In certain embodiments, HIP formation can occur during or after emulsification, e.g., as a result of equilibrium conditions in the fine emulsion. Without wishing to be bound by any theory, it is believed that organic-soluble counter ions (the hydrophobic acid) can facilitate diffusion of the therapeutic agent into a nanoparticle of an emulsion as a result of HIP formation. Without wishing to be bound by any theory, the HIP may remain in the nanoparticle before solidification of the nanoparticle since the solubility of the HIP in the nanoparticle is higher than the solubility of the HIP in the aqueous phase of the emulsion and/or in the quench. For example, by selecting a pH for the quench that is between the $pK_a$ of the therapeutic agent and the $pK_a$ of the hydrophobic acid, formation of ionized therapeutic agent and hydrophobic acid can be optimized. However, selecting a pH that is too high may tend to cause the hydrophobic acid to diffuse out of the nanoparticle, whereas selecting a pH that is too low may tend to cause the therapeutic agent to diffuse out of the nanoparticle.

In some embodiments, the pH of an aqueous solution used in a nanoparticle formulation process (e.g., including, but not limited to, the aqueous phase, the emulsion phase, the quench, and the quenched phase) may be independently selected and may be between about 1 and about 3, in some embodiments between about 2 and about 4, in some embodiments between about 3 and about 5, in some embodiments between about 4 and about 6, in some embodiments between about 5 and about 7, in some embodiments between about 6 and about 8, in some embodiments between about 7 and about 9, and in some embodiments between about 8 and about 10. In certain embodiments, the pH of an aqueous solution used in a nanoparticle formulation process may be between about 3 and about 4, in some embodiments between about 4 and about 5, in some embodiments between about 5 and about 6, in some embodiments between about 6 and about 7, in some embodiments between about 7 and about 8, and in some embodiments between about 8 and about 9.

The achieved encapsulation efficiency (the percentage of active ingredient in the nanoparticle compared to the total active ingredient in the process) will vary with the exact components of the formulation used and the detailed process parameters. A high encapsulation efficiency is more economical. In some embodiments, not all of the therapeutic agent is encapsulated in the particles at this stage, and a drug solubilizer is added to the quenched phase to form a solubilized phase. The drug solubilizer may be for example, polysorbate 80 sold under the trademark Tween®80, polysorbate 20 sold under the trademark Tween® 20, polyvinyl pyrrolidone, cyclodextran, sodium dodecyl sulfate, sodium cholate, diethylnitrosamine, sodium acetate, urea, glycerin, propylene glycol, glycofurol, poly(ethylene)glycol, bris (polyoxyethyleneglycol)dodecyl ether, sodium benzoate, sodium salicylate, or combinations thereof. For example, polysorbate 80 sold under the trademark Tween®80 may be added to the quenched nanoparticle suspension to solubilize the free drug and prevent the formation of drug crystals. In some embodiments, a ratio of drug solubilizer to the therapeutic agent is about 200:1 to about 10:1, or in some embodiments about 100:1 to about 10:1 (by weight).

The solubilized phase may be filtered to recover the nanoparticles.

For example, ultrafiltration membranes may be used to concentrate the nanoparticle suspension and substantially eliminate extraneous material such as organic solvent, free drug (that is, unencapsulated therapeutic agent), drug solubilizer, and other processing aids (surfactants).

Exemplary filtration may be performed using a cross flow or tangential flow filtration system, in which the feed is passed across the filter membrane (tangentially) at positive pressure relative to the permeate side. A proportion of the extraneous material passes through the membrane as permeate or filtrate; everything else is retained on the feed side of the membrane as retentate. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

In some embodiments, the concentration of the extraneous material in the retentate can be reduced by "washing out" with water, a process called diafiltration. The amount of the extraneous material removed is related to the filtrate volume generated, relative to the retentate volume. The filtrate volume generated is usually referred to in terms of "diafiltration volumes" or diavolumes. A single diavolume is the volume of retentate when diafiltration is started.

Diafiltration may be performed using a constant volume approach, meaning the diafiltrate (cold deionized water, e.g., about 0 to about 5° C., or 0 to about 10° C.) may added to the feed suspension at the same rate as the filtrate is removed from the suspension. When the volume of filtrate collected equals the starting retentate volume, 1 diavolume has been processed.

In some embodiments, filtering may include a first filtering using a first temperature of about 0 to about 5° C., or 0 to about 10° C., and a second temperature of about 20 to about 30° C., or 15 to about 35° C. In some embodiments, filtering may include processing about 1 to about 30, in some cases about 1 to about 15, or in some cases 1 to about 6 diavolumes. For example, filtering may include processing about 1 to about 30, or in some cases about 1 to about 6 diavolumes, at about 0 to about 5° C., and processing at least one diavolume (e.g., about 1 to about 15, about 1 to about 3, or about 1 to about 2 diavolumes) at about 20 to about 30° C. In some embodiments, filtering comprises processing different diavolumes at different distinct temperatures.

In one embodiment, about 20 diavolumes is used of cold deionised water. In another embodiment, about 20 diavolumes of deionised water at ambient temperature is used.

After purifying and concentrating the nanoparticle suspension, the particles may be passed through one, two or more sterilizing and/or depth filters, for example, using ~0.2 µm depth pre-filter. For example, a sterile filtration step may involve filtering the therapeutic nanoparticles using a filtration train at a controlled rate. In some embodiments, the filtration train may include a depth filter and a sterile filter.

In another embodiment of preparing nanoparticles, an organic phase is formed composed of a mixture of the therapeutic agent (AZD1152 hqpa) and polymer (homopolymer and co-polymer). The organic phase is mixed with an aqueous phase at approximately a 1:5 ratio (organic phase: aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. In some embodiments, the quench: emulsion ratio may be about 2:1 to about 40:1, or in some embodiments about 5:1 to about 15:1. In some embodiments, the quench:emulsion ratio is approximately 8.5:1. Then a solution of polysorbate sold under the trademark Tween® (e.g., polysorbate 80 sold under the trademark Tween®80) is added to the quench to achieve approximately 2% polysorbate sold under the trademark Tween® overall. This serves to dissolve free, unencapsulated therapeutic agent (ie AZD1152 hqpa). The nanoparticles are then isolated through either centrifugation or ultrafiltration/diafiltration.

It will be appreciated that the amounts of polymer, therapeutic agent (ie AZD1152 hqpa), and hydrophobic acid that are used in the preparation of the formulation may differ from a final formulation. For example, some of the AZD1152 hqpa may not become completely incorporated in a nanoparticle and such free AZD1152 hqpa may be e.g., filtered away. For example, in an embodiment, a first organic solution containing about 11 weight percent theoretical loading of AZD1152 hqpa in a first organic solution containing about 9% of a first hydrophobic acid (e.g., a fatty acid), a second organic solution containing about 89 weight percent polymer (e.g., the polymer may include PLA-PEG), and an aqueous solution containing about 0.12% of a second hydrophobic acid (e.g., a bile acid) may be used in the preparation of a formulation that results in, e.g., a final nanoparticle comprising about 2 weight percent AZD1152 hqpa, about 97.5 weight percent polymer, and about 0.5% total hydrophobic acid. Such processes may provide final nanoparticles suitable for administration to a patient that includes about 1 to about 20 percent by weight AZD1152 hqpa, e.g., about 1, about 2, about 3, about 4, about 5, about 8, about 10, or about 15 percent AZD1152 hqpa by weight.

Furthermore, it will be appreciated that the product formed from processes using hydrophobic acids such as trifluoroacetic acid (see for example Example 3) may undergo ion exchange with hydrophobic acids from salts such as sodium cholate used initially as surfactants in the water phase. For example cholic acid may be retained as a hydrophobic acid in the nanoparticles after the use of trifluoroacetic acid and sodium cholate in processing, as shown in Example 3.

In some embodiments, quenching of the emulsion phase comprises mixing the emulsion phase with a second aqueous solution having a pH between about 2 and about 8, such as between about 4 and about 7.

In another aspect, a process for preparing a therapeutic nanoparticle is provided. The process comprises combining a first organic phase with a first aqueous solution to form a second phase; emulsifying the second phase to form an emulsion phase, wherein the emulsion phase comprises a first polymer, a basic therapeutic agent which is AZD1152 hqpa, and a substantially hydrophobic acid; quenching of the emulsion phase thereby forming a quenched phase, wherein quenching of the emulsion phase comprises mixing the emulsion phase with a second aqueous solution having a pH between about 4 and about 7.

In some embodiments, the process further comprises filtering the quenched phase to recover the therapeutic nanoparticles.

In some embodiments, the process further comprises combining AZD1152 hqpa and the acid in the second phase prior to emulsifying the second phase. For example, in some embodiments, AZD1152 hqpa and the acid form a hydrophobic ion pair prior to emulsifying the second phase. In other embodiments, AZD1152 hqpa and the acid form a hydrophobic ion pair during emulsification of the second phase.

In some embodiments, the process further comprises combining AZD1152 hqpa and the acid in the second phase substantially concurrently with emulsifying the second phase. For example, in some embodiments, the first organic phase comprises AZD1152 hqpa and the first aqueous solution comprises the acid.

In other embodiments, the first organic phase comprises the polymer, AZD1152 hqpa and the substantially hydrophobic acid.

In one aspect, there is provided a process for preparing a therapeutic nanoparticle comprising combining a first organic phase with a first aqueous solution to form a second phase; emulsifying the second phase to form an emulsion phase, wherein the emulsion phase comprises a first polymer, a basic therapeutic agent which is AZD1152 hqpa, and pamoic acid; quenching of the emulsion phase thereby forming a quenched phase. In this aspect, preferably, quenching of the emulsion phase comprises mixing the emulsion phase with a second aqueous solution having a pH between about 4 and about 7.

In a further aspect, there is provided a process for preparing a therapeutic nanoparticle comprising combining a first organic phase with a first aqueous solution to form a second phase; emulsifying the second phase to form an emulsion phase, wherein the emulsion phase comprises a first polymer, a basic therapeutic agent which is AZD1152 hqpa and a substantially hydrophobic acid selected from deoxycholic acid and dioctylsulfosuccinic acid; quenching of the emulsion phase thereby forming a quenched phase, wherein quenching of the emulsion phase comprises mixing the emulsion phase with an aqueous solution having a pH between about 4 and about 7.

Conveniently, the emulsion phase is held, for example by storage in ice, for a period (such as 5 to 15 minutes) before quenching. In some aspects, as referred to above, the emulsion is carried out in a two stage process, with formation of a coarse emulsion preceding formation of a fine emulsion. In some embodiments, a coarse emulsion is formed and this may conveniently be held, for example by storage in ice, for a period (such as 5 to 15 minutes) before the fine emulsion is formed. The fine emulsion itself, may also be stored, for example at a temperature of 0-5° C., in some embodiments at about 2° C., for a period of 1-15 minutes (in some embodiments about 1 minute, in other embodiments about 2 minutes, in other embodiments, not more than 1 minutes, in still further embodiments for at least 5 minutes) before quenching.

Conveniently the quench is carried out at reduced temperature such as at <5° C.

Suitably, in the above aspects and embodiment, the first aqueous phase comprises a surfactant, such as sodium cholate or polyoxyethylene (100) stearyl ether sold under the trademark Brij®, in water and benzyl alcohol.

In a further aspect, there is provided a process for preparing a therapeutic nanoparticle comprising combining a first organic phase with a first aqueous solution to form a second phase; emulsifying the second phase to form an emulsion phase, wherein the emulsion phase comprises a first polymer, a basic therapeutic agent which is AZD1152 hqpa and a substantially hydrophobic acid selected from deoxycholic acid, pamoic acid and dioctylsulfosuccinic acid; optionally holding the emulsion phase for a hold time (such as 5 to 15 minutes, conveniently at about 0° C.); quenching of the emulsion phase thereby forming a quenched phase, wherein quenching of the emulsion phase comprises mixing the emulsion phase with an aqueous solution having a pH between about 4 and about 7 (such as about pH 6.5), preferably at <5° C. Suitably the first aqueous phase comprises a surfactant, such as sodium cholate or polyoxyethylene (100) stearyl ether sold under the trademark Brij®, in water and benzyl alcohol.

In a further aspect, there is provided a process for preparing a therapeutic nanoparticle comprising:
1) combining a first organic phase (which comprises a polymer, AZD1152 hqpa and a substantially hydrophobic acid phase selected from deoxycholic acid, pamoic acid and dioctylsulfosuccinic acid in one or more solvents) with a first aqueous solution (comprising a surfactant in water) to form a second phase;
2) emulsifying the second phase to form an emulsion;
3) optionally holding the emulsion phase for a hold time (such as 5 to 15 minutes, conveniently at about 0° C.);
4) quenching of the emulsion phase <5° C. thereby forming a quenched phase, wherein quenching of the emulsion phase comprises mixing the emulsion phase with a second aqueous solution having a pH between about 4 and about 7 (such as about pH 6.5);
5) concentrating and isolating the resulting nanoparticles by filtration.

Suitably the first aqueous phase comprises a surfactant, such as sodium cholate or polyoxyethylene (100) stearyl ether sold under the trademark Brij®, in water and benzyl alcohol.

In a further aspect, there is provided a process for preparing a therapeutic nanoparticle comprising:
1) combining a first organic phase (which comprises a polymer, AZD1152 hqpa and a substantially hydrophobic acid phase selected from deoxycholic acid, pamoic acid and dioctylsulfosuccinic acid in one or more solvents) with a first aqueous solution (comprising a surfactant in water) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase <5° C. thereby forming a quenched phase, wherein quenching of the emulsion phase comprises mixing the emulsion phase with a second aqueous solution having a pH between about 4 and about 7 (such as about pH 6.5);
7) concentrating and isolating the resulting nanoparticles by filtration.

Suitably the first aqueous phase comprises a surfactant, such as sodium cholate or polyoxyethylene (100) stearyl ether sold under the trademark Brij®, in water and benzyl alcohol.

In a further aspect, there is provided a process for preparing a therapeutic nanoparticle comprising:
1) combining a first organic phase (which comprises a polymer in ethyl acetate, AZD1152 hqpa in a TFA/water/benzyl alcohol solvent system and a substantially hydrophobic acid phase selected from deoxycholic acid, pamoic acid and dioctylsulfosuccinic acid in DMSO) with a first aqueous solution (comprising a surfactant such as sodium cholate or polyoxyethylene (100) stearyl ether sold under the trademark Brij®, in water and benzyl alcohol) to form a second phase;
2) emulsifying the second phase to form an emulsion;
3) optionally holding the emulsion phase for a hold time (such as 5 to 15 minutes, conveniently at about 0° C.);
4) quenching of the emulsion phase at <5° C. thereby forming a quenched phase, wherein quenching of the emulsion phase comprises mixing the emulsion phase with a second aqueous solution having a pH between about 4 and about 7 (such as about pH 6.5);
5) concentrating and isolating the resulting nanoparticles by filtration.

Further surfactant such as polysorbate 80 sold under the trademark Tween® 80 in water may be added to the quenched solution prior to concentration and filtration.

In a further aspect, there is provided a process for preparing a therapeutic nanoparticle comprising:
1) combining a first organic phase (which comprises a polymer in ethyl acetate, AZD1152 hqpa in a TFA/water/benzyl alcohol solvent system and a substantially hydrophobic acid phase selected from deoxycholic acid, pamoic acid and dioctylsulfosuccinic acid in DMSO) with a first aqueous solution (comprising a surfactant such as sodium cholate or polyoxyethylene (100) stearyl ether sold under the trademark Brij®, in water and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution having a pH between about 4 and about 7 (such as about pH 6.5);
7) concentrating and isolating the resulting nanoparticles by filtration.

Further surfactant such as polysorbate 80 sold under the trademark Tween® 80 in water may be added to the quenched solution prior to concentration and filtration.

In a further aspect, there is provided a process for preparing a therapeutic nanoparticle comprising:
1) combining a first organic phase (which comprises a polymer in ethyl acetate, AZD1152 hqpa in a TFA/water/benzyl alcohol solvent system and pamoic acid in DMSO) with a first aqueous solution (comprising a surfactant such as sodium cholate or polyoxyethylene (100) stearyl ether sold under the trademark Brij®, in water, DMSO and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising a buffer having a pH between about 4 and about 7 (such as about pH 6.5);
7) concentrating and isolating the resulting nanoparticles by filtration.

Further surfactant such as polysorbate 80 sold under the trademark Tween® 80 in water may be added to the quenched solution prior to concentration and filtration.

In a further aspect, there is provided a process for preparing a therapeutic nanoparticle comprising:
1) combining a first organic phase (which comprises a polymer, AZD1152 hqpa and pamoic acid in a solvent mixture comprising TFA, benzyl alcohol, DMSO and ethyl acetate such that the benzyl alcohol:ethyl acetate are present in a molar ratio of between 1:3 and 1:4) with a first aqueous solution (comprising a surfactant such polyoxyethylene (100) stearyl ether sold under the trademark Brij® S100, in water, DMSO and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising a buffer having a pH between about 4 and about 7 (such as about pH 6.5);
7) concentrating and isolating the resulting nanoparticles by filtration.

Further surfactant such as polysorbate 80 sold under the trademark Tween® 80 in water may be added to the quenched solution prior to concentration and filtration.

In a further aspect, there is provided a process for preparing a therapeutic nanoparticle comprising:
1) combining a first organic phase (which comprises a polymer in ethyl acetate, AZD1152 hqpa in a TFA/water/benzyl alcohol solvent system and pamoic acid in DMSO) with a first aqueous solution (comprising a surfactant such as polyoxyethylene (100) stearyl ether sold under the trademark Brij®, in water, DMSO and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising a buffer having a pH 6.5;
7) adding an aqueous surfactant solution (such as polysorbate 80 sold under the trademark Tween®80, for example a 35 weight percent polysorbate 80 sold under the trademark Tween®80 solution in water) to the quench at a ratio of about 20:1 to 100:1 polysorbate 80 sold under the trademark Tween®80 to drug by weight;
8) concentrating and isolating the resulting nanoparticles by filtration.

In a further aspect, there is provided a process for preparing a therapeutic nanoparticle comprising:
1) combining a first organic phase (which comprises a polymer, AZD1152 hqpa and pamoic acid in in a solvent mixture comprising TFA, benzyl alcohol, DMSO and ethyl acetate such that the benzyl alcohol:ethyl acetate are present in a molar ratio of between 1:3 and 1:4) with a first aqueous solution (comprising a surfactant such polyoxyethylene (100) stearyl ether sold under the trademark Brij® S100, in water, DMSO and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising a buffer at pH 6.5;
7) adding an aqueous surfactant solution as a solubilizer to the quenched solution;
8) concentrating and isolating the resulting nanoparticles by filtration.

In a further aspect, there is provided a process for preparing a therapeutic nanoparticle comprising:
1) combining a first organic phase (which comprises a 16/5 PLA-PEG copolymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6) with a first aqueous solution (comprising a surfactant such polyoxyethylene (100) stearyl ether sold under the trademark Brij® S100, in water, DMSO and benzyl alcohol) to form a second phase;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising buffer at pH 6.5;
7) adding an aqueous surfactant solution as a solubilizer;
8) concentrating and isolating the resulting nanoparticles by filtration.
Conveniently, the pamoic acid and AZD1152 hqpa are added at an initial ratio of 0.8 moles pamoic acid: 1 mole AZD1152 hqpa.

In a further aspect, there is provided a process for preparing a therapeutic nanoparticle comprising:
1) combining a first organic phase (which comprises a 16/5 PLA-PEG copolymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6) with a first aqueous solution (comprising a surfactant such polyoxyethylene (100) stearyl ether Brij® S100, in water, DMSO and benzyl alcohol) to form a second phase;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising buffer at pH 6.5;
7) adding an aqueous surfactant solution as a solubilizer;
8) concentrating and isolating the resulting nanoparticles by filtration.
Conveniently, the pamoic acid and AZD1152 hqpa are added at an initial ratio of 0.8 moles pamoic acid: 1 mole AZD1152 hqpa.

In a further aspect, there is provided a process for preparing a therapeutic nanoparticle comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) waiting for a delay time of at least 5 minutes, for example 10 minutes;
6) quenching of the emulsion phase at 0-5° C. thereby forming a quenched phase, wherein quenching of the emulsion phase comprises mixing the emulsion phase with a second aqueous solution comprising a buffer at pH 6.5 wherein the ratio of second aqueous solution to emulsion is between about 2:1 and about 10:1, such as about 3:1;
7) adding an aqueous surfactant solution to the quench;
8) concentrating and isolating the resulting nanoparticles by filtration.
Conveniently, the pamoic acid and AZD1152 hqpa are added at an initial ratio of 0.8 moles pamoic acid: 1 mole AZD1152 hqpa.

In a further aspect, there is provided a process for preparing a therapeutic nanoparticle comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6 and the pamoic acid and AZD1152 hqpa are added at an initial ratio of 0.8 moles pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) waiting for a delay time of at least 5 minutes, for example 10 minutes;

6) quenching of the emulsion phase at 0-5° C. thereby forming a quenched phase, wherein quenching of the emulsion phase comprises mixing the emulsion phase with a second aqueous solution comprising a buffer at pH 6.5 (such as a 0.17M phosphate buffer) wherein the ratio of second aqueous solution to emulsion is between about 2:1 and about 10:1, such as about 3:1;
7) adding an aqueous surfactant solution (such as polysorbate 80 sold under the trademark Tween®80, for example a 35 weight % polysorbate 80 sold under the trademark Tween®80 solution in water) to the quench solution (for example at a ratio of about 20:1 polysorbate 80 sold under the trademark Tween®80 to drug by weight);
8) concentrating and isolating the resulting nanoparticles by filtration.

In a further aspect, there is provided a process for preparing a therapeutic nanoparticle comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3) with a first aqueous solution (comprising a polyoxyethylene (100) stearyl ether sold under the trademark Brij® S100, in water, DMSO and benzyl alcohol) to form a second phase;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) after about 1 minute, quenching of the emulsion phase at about 2° C. thereby forming a quenched phase, wherein quenching of the emulsion phase comprises mixing the emulsion phase with a second aqueous solution comprising a buffer at pH 6.5;
6) adding an aqueous surfactant solution (such as polysorbate 80 sold under the trademark Tween®80, for example a 35 weight % polysorbate 80 sold under the trademark Tween®80 solution in water) to the quench solution;
7) concentrating and isolating the resulting nanoparticles by filtration.
Conveniently, the pamoic acid and AZD1152 hqpa are added at an initial ratio of about 1 mole pamoic acid: 1 mole AZD1152 hqpa.

In a further aspect, there is provided a process for preparing a therapeutic nanoparticle comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5:1;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) after about 1 minute, quenching of the emulsion phase at about 2° C., wherein quenching of the emulsion phase comprises mixing the emulsion phase with a second aqueous solution comprising a buffer at pH 6.5 (such as a 0.17M phosphate buffer) and wherein the ratio of second aqueous solution to emulsion is about 10:1;
6) adding an aqueous surfactant solution (such as polysorbate 80 sold under the trademark Tween®80, for example a 35 weight % polysorbate 80 sold under the trademark Tween®80 solution in water) to the quench at a ratio of about 100:1 polysorbate 80 sold under the trademark Tween®80 to drug by weight;
7) concentrating and isolating the resulting nanoparticles by filtration.
Conveniently, the pamoic acid and AZD1152 hqpa are added at an initial ratio of about 1 mole pamoic acid: 1 mole AZD1152 hqpa.

In a further aspect, there is provided a process for preparing a therapeutic nanoparticle comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3 and the pamoic acid and AZD1152 hqpa are added at an initial ratio of 1 mole pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5:1;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) after about 1 minute, quenching of the emulsion phase at about 2° C. thereby forming a quenched phase, wherein quenching of the emulsion phase comprises mixing the emulsion phase with a second aqueous solution comprising a buffer at pH 6.5 and wherein the ratio of second aqueous solution to emulsion is about 10:1;
6) adding an aqueous surfactant solution (such as polysorbate 80 sold under the trademark Tween®80, for example a 35 weight % polysorbate 80 sold under the trademark Tween®80 solution in water) to the quench at a ratio of about 100:1 polysorbate 80 sold under the trademark Tween®80 to drug by weight;
7) concentrating and isolating the resulting nanoparticles by filtration.

In further aspects, there is provided a process for preparing a therapeutic nanoparticle comprising any of the specific methods set out in the Examples herein.

In some embodiments, AZD1152 hqpa, when protonated, has a first $pK_a$, the acid has a second $pK_a$, and the emulsion phase is quenched with an aqueous solution having a pH equal to a $pK_a$ unit between the first $pK_a$ and the second $pK_a$. For example, in some instances, the quenched phase has a pH equal to a $pK_a$ unit between the first $pK_a$ and the second $pK_a$. In some embodiments, AZD1152 hqpa, when protonated, has a first $pK_a$, the acid has a second $pK_a$, and the first aqueous solution has a pH equal to a $pK_a$ unit between the first $pK_a$ and the second $pK_a$. In some embodiments, the pH (e.g., of the quenched phase or first aqueous solution) is equal to a $pK_a$ unit that is about equidistant between the first $pK_a$ and the second $pK_a$.

In another aspect, a therapeutic nanoparticle is provided. The therapeutic nanoparticle is prepared by emulsification of a mixture comprising a first polymer, AZD1152 hqpa, and a substantially hydrophobic acid, thereby forming an emulsion phase; and quenching of the emulsion phase thereby forming a quenched phase which comprises a plurality of the therapeutic nanoparticles.

In another aspect, a therapeutic nanoparticle is provided, wherein the therapeutic nanoparticle is prepared by emulsification of a mixture comprising a first polymer, AZD1152 hqpa, and a substantially hydrophobic acid selected from deoxycholic acid, cholic acid, dioctyl sulfosuccinic acid and pamoic acid, thereby forming an emulsion phase; and quenching of the emulsion phase thereby forming a quenched phase which comprises a plurality of the therapeutic nanoparticles.

In yet another aspect, a therapeutic nanoparticle is provided, wherein the therapeutic nanoparticle is prepared by emulsification of a mixture comprising a first polymer, AZD1152 hqpa, and pamoic acid, thereby forming an emulsion phase; and quenching of the emulsion phase thereby forming a quenched phase which comprises a plurality of the therapeutic nanoparticles.

In some embodiments, quenching of the emulsion phase comprises mixing the emulsion phase with an aqueous solution having a pH between about 2 and about 8, such as between about pH 4 and 7. Quenching at a reduced temperature, such as <5° C. is preferred.

In still another aspect, a therapeutic nanoparticle is provided, wherein the therapeutic nanoparticle is prepared by emulsification of a mixture comprising a first polymer, AZD1152 hqpa, and a substantially hydrophobic acid, thereby forming an emulsion phase; and quenching of the emulsion phase thereby forming a quenched phase which comprises a plurality of the therapeutic nanoparticles, wherein quenching of the emulsion phase comprises mixing the emulsion phase with an aqueous solution having a pH between about 4 and about 7.

In still another aspect, a therapeutic nanoparticle is provided, wherein the therapeutic nanoparticle is prepared by emulsification of a mixture comprising a first polymer, AZD1152 hqpa, and a substantially hydrophobic acid selected from deoxycholic acid, cholic acid, dioctyl sulfosuccinic acid and pamoic acid, thereby forming an emulsion phase; and quenching of the emulsion phase thereby forming a quenched phase which comprises a plurality of the therapeutic nanoparticles, wherein quenching of the emulsion phase comprises mixing the emulsion phase with an aqueous solution having a pH between about 4 and about 7.

In still another aspect, a therapeutic nanoparticle is provided, wherein the therapeutic nanoparticle is prepared by emulsification of a mixture comprising a first polymer, AZD1152 hqpa and pamoic acid, thereby forming an emulsion phase; and quenching of the emulsion phase thereby forming a quenched phase which comprises a plurality of the therapeutic nanoparticles, wherein quenching of the emulsion phase comprises mixing the emulsion phase with an aqueous solution having a pH between about 4 and about 7.

In some embodiments, the pH of a contemplated aqueous solution (e.g., first or second aqueous solution is between about 4 and about 7, e.g., between about 4 and about 5 or between about 6 and about 7.

In some embodiments, a contemplated aqueous solution comprises phosphate, citrate, or a mixture of phosphate and citrate. In some embodiments, the second aqueous solution comprises a mixture of borate, phosphate, and acetate.

In some embodiments, a contemplated process for preparing a therapeutic nanoparticle further comprises filtration of the quenched phase to recover the therapeutic nanoparticles.

In some embodiments, the quenched phase has a pH substantially the same as the emulsion phase. In some embodiments, the quenched phase has a pH between about 4 and about 7, e.g., between about 4 and about 5 or between about 6 and about 7.

In another aspect, a therapeutic nanoparticle is provided, wherein the therapeutic nanoparticle is prepared by a process of preparation comprising:
1) combining a first organic phase (which comprises a polymer, AZD1152 hqpa and a substantially hydrophobic acid phase selected from deoxycholic acid, pamoic acid and dioctylsulfosuccinic acid in one or more solvents) with a first aqueous solution (comprising a surfactant in water) to form a second phase;
2) emulsifying the second phase to form an emulsion;
3) optionally holding the emulsion phase for a hold time (such as 5 to 15 minutes, conveniently at about 0° C.);
4) quenching of the emulsion phase at <5° C. thereby forming a quenched phase, wherein quenching of the emulsion phase comprises mixing the emulsion phase with a second aqueous solution having a pH between about 4 and about 7 (such as about pH 6.5);
5) concentrating and isolating the resulting nanoparticles by filtration.

Suitably the first aqueous phase comprises a surfactant, such as sodium cholate or polyoxyethylene (100) stearyl ether sold under the trademark Brij®, in water and benzyl alcohol.

In a further aspect, a therapeutic nanoparticle is provided, wherein the therapeutic nanoparticle is prepared by a process of preparation comprising:
1) combining a first organic phase (which comprises a polymer, AZD1152 hqpa and a substantially hydrophobic acid phase selected from deoxycholic acid, pamoic acid and dioctylsulfosuccinic acid in one or more solvents) with a first aqueous solution (comprising a surfactant in water) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution having a pH between about 4 and about 7 (such as about pH 6.5);
7) concentrating and isolating the resulting nanoparticles by filtration.

Suitably the first aqueous phase comprises a surfactant, such as sodium cholate or polyoxyethylene (100) stearyl ether sold under the trademark Brij®, in water and benzyl alcohol.

In another aspect, a therapeutic nanoparticle is provided, wherein the therapeutic nanoparticle is prepared by a process of preparation comprising:
1) combining a first organic phase (which comprises a polymer in ethyl acetate, AZD1152 hqpa in a TFA/water/benzyl alcohol solvent system and a substantially hydrophobic acid phase selected from deoxycholic acid, pamoic acid and dioctylsulfosuccinic acid in DMSO) with a first aqueous solution (comprising a surfactant such as sodium cholate or polyoxyethylene (100) stearyl ether (for example as sold under the tradename Brij®), in water and benzyl alcohol) to form a second phase;

2) emulsifying the second phase to form an emulsion;
3) optionally holding the emulsion phase for a hold time (such as 5 to 15 minutes, conveniently at about 0° C.);
4) quenching of the emulsion phase at <5° C. thereby forming a quenched phase, wherein quenching of the emulsion phase comprises mixing the emulsion phase with a second aqueous solution having a pH between about 4 and about 7 (such as about pH 6.5);
5) concentrating and isolating the resulting nanoparticles by filtration.

Further surfactant such as polysorbate 80 sold under the trademark Tween® 80 in water may be added to the quenched solution prior to concentration and filtration.

In a further aspect, a therapeutic nanoparticle is provided, wherein the therapeutic nanoparticle is prepared by a process of preparation comprising:
1) combining a first organic phase (which comprises a polymer in ethyl acetate, AZD1152 hqpa in a TFA/water/benzyl alcohol solvent system and a substantially hydrophobic acid phase selected from deoxycholic acid, pamoic acid and dioctylsulfosuccinic acid in DMSO) with a first aqueous solution (comprising a surfactant such as sodium cholate or polyoxyethylene (100) stearyl ether sold under the trademark Brij®, in water and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution having a pH between about 4 and about 7 (such as about pH 6.5);
7) concentrating and isolating the resulting nanoparticles by filtration.

Further surfactant such as polysorbate 80 sold under the trademark Tween® 80 in water may be added to the quenched solution prior to concentration and filtration.

In a further aspect, a therapeutic nanoparticle is provided, wherein the therapeutic nanoparticle is prepared by a process of preparation comprising:
1) combining a first organic phase (which comprises a polymer in ethyl acetate, AZD1152 hqpa in a TFA/water/benzyl alcohol solvent system and pamoic acid in DMSO) with a first aqueous solution (comprising a surfactant such as sodium cholate or polyoxyethylene (100) stearyl ether sold under the trademark Brij®, in water, DMSO and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising a buffer having a pH between about 4 and about 7 (such as about pH 6.5);
7) concentrating and isolating the resulting nanoparticles by filtration.

Further surfactant such as polysorbate 80 sold under the trademark Tween® 80 in water may be added to the quenched solution prior to concentration and filtration.

In a further aspect, a therapeutic nanoparticle is provided, wherein the therapeutic nanoparticle is prepared by a process of preparation comprising:
1) combining a first organic phase (which comprises a polymer, AZD1152 hqpa and pamoic acid in a solvent mixture comprising TFA, benzyl alcohol, DMSO and ethyl acetate such that the benzyl alcohol:ethylacetate are present in a molar ratio of between 1:3 and 1:4) with a first aqueous solution (comprising a surfactant such polyoxyethylene (100) stearyl ether sold under the trademark Brij® S100, in water, DMSO and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising a buffer having a pH between about 4 and about 7 (such as about pH 6.5);
7) concentrating and isolating the resulting nanoparticles by filtration.

Further surfactant such as polysorbate 80 sold under the trademark Tween® 80 in water may be added to the quenched solution prior to concentration and filtration.

In a further aspect, a therapeutic nanoparticle is provided, wherein the therapeutic nanoparticle is prepared by a process of preparation comprising:
1) combining a first organic phase (which comprises a polymer in ethyl acetate, AZD1152 hqpa in a TFA/water/benzyl alcohol solvent system and pamoic acid in DMSO) with a first aqueous solution (comprising a surfactant such as polyoxyethylene (100) stearyl ether sold under the trademark Brij®, in water, DMSO and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising a buffer having a pH 6.5;
7) adding an aqueous surfactant solution (such as polysorbate 80 sold under the trademark Tween®80, for example a 35% w/w polysorbate 80 sold under the trademark Tween®80 solution in water) to the quench at a ratio of about 20:1 to 100:1 polysorbate 80 sold under the trademark Tween®80 to drug by weight;
8) concentrating and isolating the resulting nanoparticles by filtration.

In a further aspect, a therapeutic nanoparticle is provided, wherein the therapeutic nanoparticle is prepared by a process of preparation comprising:
1) combining a first organic phase (which comprises a polymer, AZD1152 hqpa and pamoic acid in in a solvent mixture comprising TFA, benzyl alcohol, DMSO and ethyl acetate such that the benzyl alcohol:ethyl acetate are present in a molar ratio of between 1:3 and 1:4) with a first aqueous solution (comprising a surfactant such polyoxyethylene (100) stearyl ether sold under the trademark Brij® S100, in water, DMSO and benzyl alcohol) to form a second phase;
2) emulsifying the second phase to form a coarse emulsion;
3) holding the coarse emulsion for a hold time (such as 5 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising a buffer at pH 6.5;
7) adding an aqueous surfactant solution as a solubilizer to the quenched solution;
8) concentrating and isolating the resulting nanoparticles by filtration.

In a further aspect, a therapeutic nanoparticle is provided which is described herein as formulation G1, wherein the therapeutic nanoparticle is prepared by a process of preparation comprising:
1) combining a first organic phase (which comprises a 16/5 PLA-PEG copolymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6) with a first aqueous solution (comprising a surfactant such polyoxyethylene (100) stearyl ether sold under the trademark Brij® S100, in water, DMSO and benzyl alcohol) to form a second phase;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) optionally waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising buffer at pH 6.5;
7) adding an aqueous surfactant solution as a solubilizer;
8) concentrating and isolating the resulting nanoparticles by filtration.
Conveniently, the pamoic acid and AZD1152 hqpa are added at an initial ratio of 0.8 moles pamoic acid: 1 mole AZD1152 hqpa.

In a further aspect, a therapeutic nanoparticle is provided which is described herein as formulation G1, wherein the therapeutic nanoparticle is prepared by a process of preparation comprising:
1) combining a first organic phase (which comprises a 16/5 PLA-PEG copolymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6) with a first aqueous solution (comprising a surfactant such polyoxyethylene (100) stearyl ether sold under the trademark Brij® S100, in water, DMSO and benzyl alcohol) to form a second phase;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) waiting for a delay time of at least 5 minutes;
6) quenching of the emulsion phase at 0-5° C. thereby forming a quenched phase, wherein quenching of the emulsion phase comprises mixing the emulsion phase with a second aqueous solution comprising buffer at pH 6.5;
7) adding an aqueous surfactant solution as a solubilizer;
8) concentrating and isolating the resulting nanoparticles by filtration.
Conveniently, the pamoic acid and AZD1152 hqpa are added at an initial ratio of 0.8 moles pamoic acid: 1 mole AZD1152 hqpa.

In a further aspect, a therapeutic nanoparticle is provided which is described herein as formulation G1, wherein the therapeutic nanoparticle is prepared by a process of preparation comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) waiting for a delay time of at least 5 minutes, for example 10 minutes;
6) quenching of the emulsion phase at 0-5° C. thereby forming a quenched phase, wherein quenching of the emulsion phase comprises mixing the emulsion phase with a second aqueous solution comprising a buffer at pH 6.5 wherein the ratio of second aqueous solution to emulsion is between about 2:1 and about 10:1, such as about 3:1;
7) adding an aqueous surfactant solution to the quench;
8) concentrating and isolating the resulting nanoparticles by filtration.
Conveniently, the pamoic acid and AZD1152 hqpa are added at an initial ratio of 0.8 moles pamoic acid: 1 mole AZD1152 hqpa.

In a further aspect, a therapeutic nanoparticle is provided which is described herein as formulation G1, wherein the therapeutic nanoparticle is prepared by a process of preparation comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6 and the pamoic acid and AZD1152 hqpa are added at an initial ratio of 0.8 moles pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;
2) emulsifying the second phase to form a coarse emulsion;
3) holding the coarse emulsion for a hold time (such as 10 to 15 minutes, conveniently at about 0° C. for example by immersing in an ice-bath);

4) forming a nano-emulsion using a high pressure homogenizer;
5) waiting for a delay time of at least 5 minutes, for example 10 minutes;
6) quenching of the emulsion phase at 0-5° C. thereby forming a quenched phase, wherein quenching of the emulsion phase comprises mixing the emulsion phase with a second aqueous solution comprising a buffer at pH 6.5 (such as a 0.17M phosphate buffer) wherein the ratio of second aqueous solution to emulsion is between about 2:1 and about 10:1, such as about 3:1;
7) adding an aqueous surfactant solution (such as polysorbate 80 sold under the trademark Tween®80, for example a 35% w/w polysorbate 80 sold under the trademark Tween®80 solution in water) to the quench solution (for example at a ratio of about 20:1 polysorbate 80 sold under the trademark Tween®80 to drug by weight);
8) concentrating and isolating the resulting nanoparticles by filtration.

In a further aspect, a therapeutic nanoparticle is provided which is described herein as formulation G2, wherein the therapeutic nanoparticle is prepared by a process of preparation comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3) with a first aqueous solution (comprising a polyoxyethylene (100) stearyl ether sold under the trademark Brij® S100, in water, DMSO and benzyl alcohol) to form a second phase;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) after about 1 minute, quenching of the emulsion phase at about 2° C. thereby forming a quenched phase, wherein quenching of the emulsion phase comprises mixing the emulsion phase with a second aqueous solution comprising a buffer at pH 6.5;
6) adding an aqueous surfactant solution (such as polysorbate 80 sold under the trademark Tween®80, for example a 35% w/w polysorbate 80 sold under the trademark Tween®80 solution in water) to the quench solution;
7) concentrating and isolating the resulting nanoparticles by filtration.
Conveniently, the pamoic acid and AZD1152 hqpa are added at an initial ratio of about 1 mole pamoic acid: 1 mole AZD1152 hqpa.

In a further aspect, a therapeutic nanoparticle is provided which is described herein as formulation G2, wherein the therapeutic nanoparticle is prepared by a process of preparation comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5:1;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) after about 1 minute, quenching of the emulsion phase at about 2° C., wherein quenching of the emulsion phase comprises mixing the emulsion phase with a second aqueous solution comprising a buffer at pH 6.5 (such as a 0.17M phosphate buffer) and wherein the ratio of second aqueous solution to emulsion is about 10:1;
6) adding an aqueous surfactant solution (such as polysorbate 80 sold under the trademark Tween®80, for example a 35% w/w polysorbate 80 sold under the trademark Tween®80 solution in water) to the quench at a ratio of about 100:1 polysorbate 80 sold under the trademark Tween®80 to drug by weight;
7) concentrating and isolating the resulting nanoparticles by filtration.
Conveniently, the pamoic acid and AZD1152 hqpa are added at an initial ratio of about 1 mole pamoic acid: 1 mole AZD1152 hqpa.

In a further aspect, a therapeutic nanoparticle is provided which is described herein as formulation G2, wherein the therapeutic nanoparticle is prepared by a process of preparation comprising:
1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3 and the pamoic acid and AZD1152 hqpa are added at an initial ratio of 1 mole pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5:1;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) after about 1 minute, quenching of the emulsion phase at about 2° C. thereby forming a quenched phase, wherein quenching of the emulsion phase comprises mixing the emulsion phase with a second aqueous solution comprising a buffer at pH 6.5 and wherein the ratio of second aqueous solution to emulsion is about 10:1;
6) adding an aqueous surfactant solution (such as polysorbate 80 sold under the trademark Tween®80, for example a 35% w/w polysorbate 80 sold under the trademark Tween®80 solution in water) to the quench at a ratio of about 100:1 polysorbate 80 sold under the trademark Tween®80 to drug by weight;
7) concentrating and isolating the resulting nanoparticles by filtration.

In one aspect, the final nanoparticles include about 5 to about 20% by weight of AZD1152 hqpa, such as about 8 to about 20% by weight such as about 10 to about 20% by weight, such as about 10 to about 15% by weight, such as about 10 to about 16% by weight, such as about 12 to about 16% by weight, such as about 15 to about 20% by weight, such as about 15 to about 18% by weight. In one aspect, the final nanoparticles include about 10 to about 20% by weight of AZD1152 hqpa. In a further aspect, the final nanoparticles include about 15 to about 20% by weight of AZD1152 hqpa.

In a further aspect, the final nanoparticles include about 15 to about 22% by weight of AZD1152 hqpa.

A further feature of the invention provides final nanoparticles comprising about 10-16% by weight of AZD1152 hqpa, about 50 to about 90 weight percent of a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and a hydrophobic acid selected from cholic acid, deoxycholic acid and dioctyl sulfosuccinic acid. In one embodiment of this feature, the hydrophobic acid is selected from deoxycholic acid and dioctyl sulfosuccinic acid. In another embodiment of this feature the hydrophobic acid is deoxycholic acid. In another embodiment of this feature the hydrophobic acid is dioctyl sulfosuccinic acid. In another embodiment of this feature the hydrophobic acid is cholic acid. In another embodiment of this feature the hydrophobic acid is a mixture of cholic acid and deoxycholic acid; in this embodiment, suitably the hydrophobic acids are in a molar ratio of about 3:2 deoxycholic acid:cholic acid and the molar ratio of total hydrophobic acid:AZD1152 hqpa is about 2:1.

A further feature of the invention provides nanoparticles comprising about 10-20% by weight of AZD1152 hqpa, about 50 to about 90 weight percent of a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and a hydrophobic acid selected from cholic acid, deoxycholic acid, pamoic acid and dioctyl sulfosuccinic acid.

In another aspect, the therapeutic nanoparticle comprises about 35 to about 94.75 weight percent of a diblock poly(lactic) acid-poly(ethylene)glycol copolymer having a number average molecular weight of about 16 kDa poly(lactic acid) and a number average molecular weight of about 5 kDa poly(ethylene)glycol, wherein the therapeutic nanoparticle comprises about 10 to about 30 weight percent poly(ethylene)glycol, about 0.05 to about 35 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 30 weight percent of AZD1152 hqpa or a pharmaceutically acceptable salt thereof.

In another aspect, the therapeutic nanoparticle comprises about 35 to about 94 weight percent of a diblock poly(lactic) acid-poly(ethylene)glycol copolymer having a number average molecular weight of about 16 kDa poly(lactic acid) and a number average molecular weight of about 5 kDa poly(ethylene)glycol, wherein the therapeutic nanoparticle comprises about 10 to about 30 weight percent poly(ethylene)glycol, about 1 to about 35 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 30 weight percent of AZD1152 hqpa or a pharmaceutically acceptable salt thereof.

In another aspect, the therapeutic nanoparticle comprises about 65 to about 90 weight percent of a diblock poly(lactic) acid-poly(ethylene)glycol copolymer having a number average molecular weight of about 16 kDa poly(lactic acid) and a number average molecular weight of about 5 kDa poly(ethylene)glycol, wherein the therapeutic nanoparticle comprises about 10 to about 30 weight percent poly(ethylene)glycol, about 5 to about 15 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 20 weight percent of AZD1152 hqpa or a pharmaceutically acceptable salt thereof.

In another aspect, the therapeutic nanoparticle comprises about 35 to about 94 weight percent of a diblock poly(lactic) acid-poly(ethylene)glycol copolymer having a number average molecular weight of about 16 kDa poly(lactic acid) and a number average molecular weight of about 5 kDa poly(ethylene)glycol, wherein the therapeutic nanoparticle comprises about 10 to about 30 weight percent poly(ethylene)glycol, about 1 to about 35 weight percent of pamoic acid and about 5 to about 30 weight percent of AZD1152 hqpa or a pharmaceutically acceptable salt thereof.

In another aspect, the therapeutic nanoparticle comprises about 55 to about 80 weight percent of a diblock poly(lactic) acid-poly(ethylene)glycol copolymer having a number average molecular weight of about 16 kDa poly(lactic acid) and a number average molecular weight of about 5 kDa poly(ethylene)glycol, wherein the therapeutic nanoparticle comprises about 10 to about 30 weight percent poly(ethylene)glycol, about 10 to about 20 weight percent of pamoic acid and about 10 to about 25 weight percent of AZD1152 hqpa or a pharmaceutically acceptable salt thereof.

In another aspect, the therapeutic nanoparticle comprises about 65 to about 76 weight percent of a diblock poly(lactic) acid-poly(ethylene)glycol copolymer having a number average molecular weight of about 16 kDa poly(lactic acid) and a number average molecular weight of about 5 kDa poly(ethylene)glycol, wherein the therapeutic nanoparticle comprises about 10 to about 20 weight percent poly(ethylene)glycol, about 9 to about 15 weight percent of pamoic acid and about 15 to about 20 weight percent of AZD1152 hqpa or a pharmaceutically acceptable salt thereof.

A further feature of the invention provides nanoparticles comprising about 10-20 weight percent of AZD1152 hqpa, about 50 to about 90 weight percent of a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and pamoic acid.

Further features of the invention comprise each of the formulations of the Examples referred to as formulations E, F1, F2, G1 and G2 herein. Still further features of the invention comprise each of the formulations of the Examples referred to as formulations E, F1, F2, G1 and G2 herein, wherein the % by weight of AZD1152 hqpa and/or the % by weight of hydrophobic acid varies by +/−about 1% by weight (and so the amount of polymer varies accordingly). Still further features of the invention comprise each of the formulations of the Examples referred to as formulations E, F1, F2, G1 and G2 herein, wherein the % by weight of AZD1152 hqpa and/or the % by weight of hydrophobic acid varies by +/−about 1.5% by weight (and so the amount of polymer varies accordingly). Still further features of the invention comprise each of the formulations of the Examples referred to as formulations E, F1, F2, G1 and G2 herein, wherein the % by weight of AZD1152 hqpa and/or the % by weight of hydrophobic acid varies by +/−about 2% by weight (and so the amount of polymer varies accordingly).

In one aspect, contemplated nanoparticles have a hydrodynamic diameter of <200 nm, such as 70-140 nm.

In a further aspect of the invention there is provided nanoparticles comprising about 15-25 weight percent of AZD1152 hqpa, about 7 to 15 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol).

In a further aspect of the invention there is provided nanoparticles comprising about 15-22 weight percent of AZD1152 hqpa, about 7 to 15 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol).

In a further aspect of the invention there is provided nanoparticles comprising about 15-22 weight percent of AZD1152 hqpa, about 7 to 10 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol); wherein less than 20% of the AZD1152 hqpa is released from the nanoparticle after 30 hours in PBS and polysorbate20 at 37° C. In another embodiment of this aspect, less than 20% of the AZD1152 hqpa is released from the nanoparticle after 40 hours in PBS and polysorbate20 at 37° C. In another embodiment of this aspect, less than 20% of the AZD1152 hqpa is released from the nanoparticle after 50 hours in PBS and polysorbate20 at 37° C. Conveniently, the release of AZD1152 hqpa from the nanoparticle may be measured using the method described hereinbefore.

In a further aspect of the invention there is provided nanoparticles comprising about 15-22 weight percent of AZD1152 hqpa, about 7 to 10 weight percent of pamoic acid, wherein the AZD1152 hqpa and the pamoic acid form a hydrophobic ion pair, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol); wherein less than 20% of the AZD1152 hqpa is released from the nanoparticle after 30 hours in PBS and polysorbate20 at 37° C. In another embodiment of this aspect, less than 20% of the AZD1152 hqpa is released from the nanoparticle after 40 hours in PBS and polysorbate20 at 37° C. In another embodiment of this aspect, less than 20% of the AZD1152 hqpa is released from the nanoparticle after 50 hours in PBS and polysorbate20 at 37° C. Conveniently, the release of AZD1152 hqpa from the nanoparticle may be measured using the method described hereinbefore.

In a further aspect of the invention there is provided nanoparticles comprising about 15-22 weight percent of AZD1152 hqpa, about 7 to 10 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol); wherein less than 20% of the AZD1152 hqpa is released from the nanoparticle after 30 hours in PBS and polysorbate20 at 37° C., and wherein the nanoparticles are made by a process comprising the following steps:

1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6 and the pamoic acid and AZD1152 hqpa are added at an initial ratio of 0.8 moles pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;

2) emulsifying the second phase to form a coarse emulsion;

3) holding the coarse emulsion for a hold time (such as 10 to 15 minutes, conveniently at about 0° C. for example by immersing in an ice-bath);

4) forming a nano-emulsion using a high pressure homogenizer;

5) optionally waiting for a delay time of at least 5 minutes, for example 10 minutes;

6) quenching of the emulsion phase at 0-5° C. thereby forming a quenched phase, wherein quenching of the emulsion phase comprises mixing the emulsion phase with a second aqueous solution comprising a buffer at pH 6.5 (such as a 0.17M phosphate buffer) wherein the ratio of second aqueous solution to emulsion is between about 2:1 and about 10:1, such as about 3:1;

7) adding an aqueous surfactant solution (such as polysorbate 80 sold under the trademark Tween®80, for example a 35 weight percent polysorbate 80 sold under the trademark Tween®80 solution in water) to the quench solution (for example at a ratio of about 20:1 polysorbate 80 sold under the trademark Tween®80 to drug by weight);

8) concentrating and isolating the resulting nanoparticles by filtration.

In a further aspect of the invention there is provided nanoparticles comprising about 15-22 weight percent of AZD1152 hqpa, about 7 to 10 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol); wherein the nanoparticles are made by a process comprising the following steps:

1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6 and the pamoic acid and AZD1152 hqpa are added at an initial ratio of 0.8 moles pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;

2) emulsifying the second phase to form a coarse emulsion;

3) holding the coarse emulsion for a hold time (such as 10 to 15 minutes, conveniently at about 0° C. for example by immersing in an ice-bath);

4) forming a nano-emulsion using a high pressure homogenizer;

5) optionally waiting for a delay time of at least 5 minutes, for example 10 minutes;

6) quenching of the emulsion phase at 0-5° C. thereby forming a quenched phase, wherein quenching of the emulsion phase comprises mixing the emulsion phase with a second aqueous solution comprising a buffer at pH 6.5 (such as a 0.17M phosphate buffer) wherein the ratio of second aqueous solution to emulsion is between about 2:1 and about 10:1, such as about 3:1;

7) adding an aqueous surfactant solution (such as polysorbate 80 sold under the trademark Tween®80, for example a 35 weight percent polysorbate 80 sold under the trademark Tween®80 solution in water) to the quench solution (for example at a ratio of about 20:1 polysorbate 80 sold under the trademark Tween®80 to drug by weight);

8) concentrating and isolating the resulting nanoparticles by filtration.

In one aspect, there is provided therapeutic nanoparticles described as formulation G1 herein, comprising about 15-22 weight percent of AZD1152 hqpa, about 7 to 10 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene) glycol).

In another aspect there is provided therapeutic nanoparticles described as formulation G2 herein, comprising about 15-22 weight percent of AZD1152 hqpa, about 9 to 13 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene) glycol).

Pharmaceutical Formulations

Nanoparticles disclosed herein may be combined with pharmaceutically acceptable carriers to form a pharmaceutical composition, according to another aspect. As would be appreciated by one of skill in this art, the carriers may be chosen based on the route of administration as described below, the location of the target issue, the drug being delivered, the time course of delivery of the drug, etc.

In another aspect, a pharmaceutically acceptable composition is provided. The pharmaceutically acceptable composition comprises a plurality of contemplated therapeutic nanoparticles and a pharmaceutically acceptable carrier. The pharmaceutically acceptable composition may also comprise one or more excipients and/or diluents. In one embodiment of this aspect, the pharmaceutical composition comprises a plurality of therapeutic nanoparticles, wherein the nanoparticles comprise about 10-20% by weight of AZD1152 hqpa, about 50 to about 90 weight percent of a diblock poly(lactic) acid-poly(ethylene)glycol copolymer (wherein the therapeutic nanoparticle comprises about 10 to about 30 weight percent poly(ethylene)glycol and the poly (lactic) acid-poly(ethylene)glycol copolymer has a number average molecular weight of about 16 kDa poly(lactic acid) and a number average molecular weight of about 5 kDa poly(ethylene)glycol) and a hydrophobic acid selected from cholic acid, deoxycholic acid, pamoic acid and dioctyl sulfosuccinic acid.

In a further aspect of the invention there is provided a pharmaceutical composition comprising a plurality of therapeutic nanoparticles and one or more pharmaceutically-acceptable excipients, diluents and/or carriers, wherein each therapeutic nanoparticle comprises AZD1152 hqpa and optionally further comprises a hydrophobic acid.

In a further aspect of the invention there is provided a pharmaceutical composition comprising a plurality of therapeutic nanoparticles and one or more pharmaceutically-acceptable excipients, diluents and/or carriers, wherein each therapeutic nanoparticle comprises AZD1152 hqpa, a suitable polymer and optionally further comprises a hydrophobic acid.

In another aspect, there is provided a pharmaceutical composition comprising a plurality of therapeutic nanoparticles and one or more pharmaceutically-acceptable excipients, diluents and/or carriers, wherein the nanoparticles comprise AZD1152 hqpa, a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene) glycol) and a hydrophobic acid selected from cholic acid, deoxycholic acid, pamoic acid and dioctyl sulfosuccinic acid.

In a further aspect of the invention there is provided a pharmaceutical composition comprising a plurality of therapeutic nanoparticles and one or more pharmaceutically-acceptable excipients, diluents and/or carriers, wherein each therapeutic nanoparticle comprises AZD1152 hqpa and further comprises a hydrophobic acid. In these aspects, conveniently the hydrophobic acid is selected from deoxycholic acid, cholic acid, dioctyl sulfosuccinic acid and pamoic acid; conveniently the hydrophobic acid may be a mixture of deoxycholic acid and cholic acid.

In a further aspect of the invention there is provided a pharmaceutical composition comprising a plurality of therapeutic nanoparticles and one or more pharmaceutically-acceptable excipients, diluents and/or carriers, wherein each therapeutic nanoparticle comprises about 35 to about 94.75 weight percent of a diblock poly(lactic) acid-poly(ethylene) glycol copolymer, wherein the therapeutic nanoparticle comprises about 10 to about 30 weight percent poly(ethylene)glycol, about 0.05 to about 35 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 30 weight percent of AZD1152 hqpa or a pharmaceutically acceptable salt thereof.

In a further aspect of the invention there is provided a pharmaceutical composition comprising a plurality of therapeutic nanoparticles and one or more pharmaceutically-acceptable excipients, diluents and/or carriers, wherein each therapeutic nanoparticle comprises about 65 to about 90 weight percent of a diblock poly(lactic) acid-poly(ethylene) glycol copolymer, wherein the therapeutic nanoparticle comprises about 10 to about 30 weight percent poly(ethylene)glycol, about 5 to about 15 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 20 weight percent of AZD1152 hqpa or a pharmaceutically acceptable salt thereof.

In a further aspect of the invention there is provided a pharmaceutical composition comprising a plurality of therapeutic nanoparticles and one or more pharmaceutically-acceptable excipients, diluents and/or carriers, wherein each therapeutic nanoparticle comprises about 35 to about 94.75 weight percent of a diblock poly(lactic) acid-poly(ethylene) glycol copolymer, wherein the therapeutic nanoparticle comprises about 10 to about 30 weight percent poly(ethylene)glycol, about 0.05 to about 35 weight percent of pamoic acid and about 5 to about 30 weight percent of AZD1152 hqpa or a pharmaceutically acceptable salt thereof.

In a further aspect of the invention there is provided a pharmaceutical composition comprising a plurality of therapeutic nanoparticles and one or more pharmaceutically-acceptable excipients, diluents and/or carriers, wherein each therapeutic nanoparticle comprises about 55 to about 80 weight percent of a diblock poly(lactic) acid-poly(ethylene) glycol copolymer, wherein the therapeutic nanoparticle comprises about 10 to about 30 weight percent poly(ethylene)glycol, about 10 to about 20 weight percent of pamoic acid and about 10 to about 25 weight percent of AZD1152 hqpa or a pharmaceutically acceptable salt thereof.

In a further aspect of the invention there is provided a pharmaceutical composition comprising a plurality of therapeutic nanoparticles and one or more pharmaceutically-acceptable excipients, diluents and/or carriers, wherein each therapeutic nanoparticle comprises about 65 to about 76 weight percent of a diblock poly(lactic) acid-poly(ethylene) glycol copolymer, wherein the therapeutic nanoparticle comprises about 10 to about 20 weight percent poly(ethylene)glycol, about 9 to about 15 weight percent of pamoic acid and about 15 to about 20 weight percent of AZD1152 hqpa or a pharmaceutically acceptable salt thereof.

In the pharmaceutical compositions described in the above features, conveniently the co-polymer has a number average molecular weight of about 16 kDa poly(lactic acid) and a number average molecular weight of about 5 kDa poly(ethylene)glycol.

Further features of the invention comprise a pharmaceutical composition comprising a plurality of therapeutic nanoparticles and one or more pharmaceutically-acceptable excipients, diluents and/or carriers, wherein each therapeutic nanoparticle corresponds to one of the formulations of the Examples referred to as formulations E, F1, F2, G1 and G2 herein. Still further features of the invention comprise a pharmaceutical composition comprising a plurality of therapeutic nanoparticles and one or more pharmaceutically-acceptable excipients, diluents and/or carriers, wherein each therapeutic nanoparticle corresponds to one of the formulations of the Examples referred to as formulations E, F1, F2, G1 and G2 herein, wherein the % by weight of AZD1152 hqpa and/or the % by weight of hydrophobic acid varies by +/−about 1% by weight (and so the amount of polymer varies accordingly). Still further features of the invention comprise a pharmaceutical composition comprising a plurality of therapeutic nanoparticles and one or more pharmaceutically-acceptable excipients, diluents and/or carriers, wherein each therapeutic nanoparticle corresponds to one of the formulations of the Examples referred to as formulations E, F1, F2, G1 and G2 herein, but wherein the % by weight of AZD1152 hqpa and/or the % by weight of hydrophobic acid varies by +/−about 1.5% by weight (and so the amount of polymer varies accordingly) from that described in the Examples. Still further features of the invention comprise a pharmaceutical composition comprising a plurality of therapeutic nanoparticles and one or more pharmaceutically-acceptable excipients, diluents and/or carriers, wherein each therapeutic nanoparticle corresponds to one of the of the Examples referred to as formulations E, F1, F2, G1 and G2 herein, but wherein the % by weight of AZD1152 hqpa and/or the % by weight of hydrophobic acid varies by +/−about 2% by weight (and so the amount of polymer varies accordingly) from that described in the Examples. Still further features of the invention comprise a pharmaceutical composition comprising a plurality of therapeutic nanoparticles and one or more pharmaceutically-acceptable excipients, diluents and/or carriers, wherein each therapeutic nanoparticle corresponds to one of the of the Examples referred to as formulations E, F1, F2, G1 and G2 herein, but wherein the % by weight of AZD1152 hqpa varies by up to about +/−3% by weight, the amount of hydrophobic acid varies in proportion to the amount of AZD1152 hqpa corresponding to the proportions in the Exemplified formulations herein and so the amount of polymer varies accordingly.

In a further aspect there is provided a pharmaceutical composition comprising a plurality of therapeutic nanoparticles and one or more pharmaceutically-acceptable excipients, diluents and/or carriers, wherein each therapeutic nanoparticle comprises about 15 to about 25% by weight of AZD1152 hqpa, about 7 to about 15% by weight of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol).

In a further aspect there is provided a pharmaceutical composition comprising a plurality of therapeutic nanoparticles and one or more pharmaceutically-acceptable excipients, diluents and/or carriers, wherein each therapeutic nanoparticle comprises about 15 to about 22% by weight of AZD1152 hqpa, about 7 to about 15% by weight of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol).

In a further aspect there is provided a pharmaceutical composition comprising a plurality of therapeutic nanoparticles and one or more pharmaceutically-acceptable excipients, diluents and/or carriers, wherein each therapeutic nanoparticle comprises about 15 to about 22% by weight of AZD1152 hqpa, about 7 to about 15% by weight of pamoic acid, and about 63 to about 78 weight percent of a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol).

In a further aspect there is provided a pharmaceutical composition comprising a plurality of therapeutic nanoparticles and one or more pharmaceutically-acceptable excipients, diluents and/or carriers, wherein each therapeutic nanoparticle comprises a diblock poly(lactic) acid-poly(ethylene) glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and a mixture of about 15 to about 22% by weight of AZD1152 hqpa and about 7 to about 15% by weight of pamoic acid.

In a further aspect there is provided a pharmaceutical composition comprising a plurality of therapeutic nanoparticles and one or more pharmaceutically-acceptable excipients, diluents and/or carriers, wherein each therapeutic nanoparticle comprises a diblock poly(lactic) acid-poly(ethylene) glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and the product obtained by interaction of about 15 to about 22% by weight of AZD1152 hqpa and about 7 to about 15% by weight of pamoic acid.

In a further aspect there is provided a pharmaceutical composition comprising a plurality of therapeutic nanoparticles and one or more pharmaceutically-acceptable excipients, diluents and/or carriers, wherein each therapeutic nanoparticle comprises a diblock poly(lactic) acid-poly(ethylene) glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and a hydrophobic ion pair formed between about 15 to about 22% by weight (of the nanoparticle) of AZD1152 hqpa and about 7 to about 15% by weight (of the nanoparticle) of pamoic acid.

In a further aspect there is provided a pharmaceutical composition comprising a plurality of therapeutic nanoparticles and one or more pharmaceutically-acceptable excipients, diluents and/or carriers, wherein each therapeutic nanoparticle comprises about 15 to about 22% by weight of AZD1152 hqpa, about 7 to about 15% by weight of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol); wherein less than 20% of the AZD1152 hqpa is released from the nanoparticle after 30 hours in PBS and polysorbate20 at 37° C. In another embodiment of this aspect, less than 20% of the AZD1152 hqpa is released from the nanoparticle after 40 hours in PBS and polysorbate20 at 37° C. In another embodiment of this aspect, less than 20% of the AZD1152 hqpa is released from the nanoparticle after 50 hours in PBS and polysorbate20 at 37° C. Conveniently, the release of AZD1152 hqpa from the nanoparticle is measured using the method described hereinbefore.

In a further aspect there is provided a pharmaceutical composition comprising a plurality of therapeutic nanoparticles and one or more pharmaceutically-acceptable excipients, diluents and/or carriers, wherein each therapeutic nanoparticle comprises about 15 to about 22% by weight of AZD1152 hqpa, about 7 to about 15% by weight of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol); wherein less than 20% of the AZD1152 hqpa is released from the nanoparticle after 30 hours in PBS and polysorbate20 at 37° C., and wherein the nanoparticles are made by a process comprising the following steps:

1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6 and the pamoic acid and AZD1152 hqpa are added at an initial ratio of 0.8 moles pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;
2) emulsifying the second phase to form a coarse emulsion;
3) holding the coarse emulsion for a hold time (such as 10 to 15 minutes, conveniently at about 0° C. for example by immersing in an ice-bath);
4) forming a nano-emulsion using a high pressure homogenizer;
5) optionally waiting for a delay time of at least 5 minutes, for example 10 minutes;
6) quenching of the emulsion phase at 0-5° C. thereby forming a quenched phase, wherein quenching of the emulsion phase comprises mixing the emulsion phase with a second aqueous solution comprising a buffer at pH 6.5 (such as a 0.17M phosphate buffer) wherein the ratio of second aqueous solution to emulsion is between about 2:1 and about 10:1, such as about 3:1;
7) adding an aqueous surfactant solution (such as polysorbate 80 sold under the trademark Tween®80, for example a 35 weight percent polysorbate 80 sold under the trademark Tween®80 solution in water) to the quench solution (for example at a ratio of about 20:1 polysorbate 80 sold under the trademark Tween®80 to drug by weight);
8) concentrating and isolating the resulting nanoparticles by filtration.

Suitably, nanoparticles in the above pharmaceutical compositions have a hydrodynamic diameter of <200 nm, such as 70-140 nm.

The pharmaceutical compositions can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles are administered to a subject in need thereof systemically, e.g., by IV (IntraVenous) infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) polysorbate 80 sold under the trademark TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of a nanoparticle containing the therapeutic agent is chosen by the individual physician in view of the patient to be treated, in general, dosage and administration are adjusted to provide an effective amount of the therapeutic nanoparticle to the patient being treated. As used herein, the "effective amount" of a nanoparticle containing the therapeutic agent refers to the amount necessary to elicit the desired biological response. As will be appreciated by those of ordinary skill in this art, the effective amount of a nanoparticle containing the therapeutic agent may vary depending on such factors as the desired biological endpoint, the drug to be delivered, the target tissue, the route of administration, etc. For example, the effective amount of a nanoparticle containing the therapeutic agent might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In one aspect, the pharmaceutical formulation comprising the AZD1152 hqpa containing nanoparticles is designed such that it releases the AZD1152 hqpa slowly over several days. For example, the pharmaceutical formulation may be such that a dose is administered to the patient on (for example) days 1 and 3, days 1 and 5 or days 1 and 7 of a seven day treatment cycle. The cycle may be repeated every week, two weeks or three weeks in a monthly or bi-monthly treatment cycle. The amount of drug to be administered at each visit is thus calculated in order to achieve a particular total drug exposure over the treatment schedule. Advantageously, the nanoparticle containing formulations may reduce the time required for administration of the drug to the patient at each dose and may reduce the number of hospital visits for treatments that a patient needs to make, compared to previously known methods of administering AZD1152.

Suitably when administering to man the dose of AZD1152 hqpa delivered by the nanoparticulate formulation of the invention may be in the range from 100 mg to 2000 mg. The exact total dose to be administered will be determined by optimal PK and safety profile for the patient and the tumour type being treated, to be delivered, for example, in the schedules described above.

In an embodiment, compositions disclosed herein may include less than about 10 ppm of palladium, or less than about 8 ppm, or less than about 6 ppm of palladium. For example, provided here is a composition that includes nanoparticles wherein the composition has less than about 10 ppm of palladium.

In some embodiments, a composition suitable for freezing is contemplated, including nanoparticles disclosed herein and a solution suitable for freezing, e.g., a sugar such as a mono, di, or poly saccharide, e.g., sucrose and/or a trehalose, and/or a salt and/or a cyclodextrin solution is added to the nanoparticle suspension. The sugar (e.g., sucrose or trehalose) may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water/ionic halide is about 3-40%/10-40%/20-95%/0.1-10% (w/w/w/w) or about 5-10%/10-15%/80-90%/1-10% (w/w/w/w). For example, such solution may include nanoparticles as disclosed herein, about 5% to about 20% by weight sucrose and an ionic halide such as sodium chloride, in a concentration of about 10 to about 100 mM. In another example, provided herein is a nanoparticle formulation comprising a plurality of disclosed nanoparticles, trehalose, cyclodextrin, and water; wherein the nanoparticles/trehalose/water/cyclodextrin is about 3-40%/1-25%/20-95%/1-25% (w/w/w/w) or about 5-10%/1-25%/80-90%/10-15% (w/w/w/w).

For example, a contemplated solution may include nanoparticles as disclosed herein, about 1% to about 25% by weight of a disaccharide such as trehalose or sucrose (e.g., about 5% to about 25% trehalose or sucrose, e.g. about 10% trehalose or sucrose, or about 15% trehalose or sucrose, e.g. about 5% sucrose) by weight) and a cyclodextrin such as β-cyclodextrin, in a concentration of about 1% to about 25% by weight (e.g. about 5% to about 20%, e.g. 10% or about 20% by weight, or about 15% to about 20% by weight cyclodextrin). Contemplated formulations may include a plurality of disclosed nanoparticles (e.g. nanoparticles having PLA-PEG and an active agent), and about 2% to about 15 wt % (or about 4 wt % to about 6 wt %), e.g. about 5 wt %) sucrose and about 5 wt % to about 20 wt % (e.g. about 7 wt % to about 12 wt %, e.g. about 10 wt %) of a cyclodextrin, e.g., HPbCD).

The present disclosure relates in part to lyophilized pharmaceutical compositions that, when reconstituted, have a minimal amount of large aggregates. Such large aggregates may have a size greater than about 0.5 µm, greater than about 1 µm, or greater than about 10 µm, and can be undesirable in a reconstituted solution. Aggregate sizes can be measured using a variety of techniques including those indicated in the U.S. Pharmacopeia at 32 <788>, hereby incorporated by reference. The tests outlined in USP 32 <788> include a light obscuration particle count test, microscopic particle count test, laser diffraction, and single particle optical sensing. In one embodiment, the particle size in a given sample is measured using laser diffraction and/or single particle optical sensing.

The USP 32 <788> by light obscuration particle count test sets forth guidelines for sampling particle sizes in a suspension. For solutions with less than or equal to 100 mL, the preparation complies with the test if the average number of particles present does not exceed 6000 per container that are >10 µm and 600 per container that are >25 µm.

As outlined in USP 32 <788>, the microscopic particle count test sets forth guidelines for determining particle amounts using a binocular microscope adjusted to 100±10× magnification having an ocular micrometer. An ocular micrometer is a circular diameter graticule that consists of a circle divided into quadrants with black reference circles denoting 10 µm and 25 µm when viewed at 100× magnification. A linear scale is provided below the graticule. The number of particles with reference to 10 µm and 25 µm are visually tallied. For solutions with less than or equal to 100 mL, the preparation complies with the test if the average number of particles present does not exceed 3000 per container that are ≥10 µm and 300 per container that are ≥25 µm.

In some embodiments, a 10 mL aqueous sample of a disclosed composition upon reconstitution comprises less than 600 particles per ml having a size greater than or equal to 10 microns; and/or less than 60 particles per ml having a size greater than or equal to 25 microns.

Dynamic light scattering (DLS) may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 weight %) amounts of larger particles can be determined in nanoparticle suspensions. Single particle optical sensing (SPOS) uses light obscuration of dilute suspensions to count individual particles of about 0.5 µm. By knowing the particle concentration of the measured sample, the weight percentage of aggregates or the aggregate concentration (particles/mL) can be calculated.

Formation of aggregates can occur during lyophilization due to the dehydration of the surface of the particles. This dehydration can be avoided by using lyoprotectants, such as disaccharides, in the suspension before lyophilization. Suitable disaccharides include sucrose, lactulose, lactose, maltose, trehalose, or cellobiose, and/or mixtures thereof. Other contemplated disaccharides include kojibiose, nigerose, isomaltose, β,β-trehalose, α,β-trehalose, sophorose, laminaribiose, gentiobiose, turanose, maltulose, palatinose, gentiobiulose, mannobiose, melibiose, melibiulose, rutinose, rutinulose, and xylobiose. Reconstitution shows equivalent DLS size distributions when compared to the starting suspension. However, laser diffraction can detect particles of >10 µm in size in some reconstituted solutions. Further, SPOS also may detect >10 µm sized particles at a concentration above that of the FDA guidelines ($10^4$-$10^5$ particles/mL for >10 µm particles).

In some embodiments, one or more ionic halide salts may be used as an additional lyoprotectant to a sugar, such as sucrose, trehalose or mixtures thereof. Sugars may include disaccharides, monosaccharides, trisaccharides, and/or polysaccharides, and may include other excipients, e.g. glycerol and/or surfactants. Optionally, a cyclodextrin may be included as an additional lyoprotectant. The cyclodextrin may be added in place of the ionic halide salt. Alternatively, the cyclodextrin may be added in addition to the ionic halide salt.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one embodiment, about 1 to about 15 weight percent sucrose may be used with an ionic halide salt. In one embodiment, the lyophilized pharmaceutical composition may comprise about 10 to about 100 mM sodium chloride. In another embodiment, the lyophilized pharmaceutical composition may comprise about 100 to about 500 mM of divalent ionic chloride salt, such as calcium chloride or zinc chloride. In yet another embodiment, the suspension to be lyophilized may further comprise a cyclodextrin, for example, about 1 to about 25 weight percent of cyclodextrin may be used.

A suitable cyclodextrin may include α-cyclodextrin, β-cyclodextrin, γ-cyclodextrin, or mixtures thereof. Exemplary cyclodextrins contemplated for use in the compositions disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glocosyl-β-cyclodextrin, and maltosyl-β-cyclodextrin. In one embodiment, about 1 to about 25 weight percent trehalose (e.g. about 10% to about 15%, e.g. 5 to about 20% by weight) may be used with cyclodextrin. In one embodiment, the lyophilized pharmaceutical composition may comprise about 1 to about 25 weight percent β-cyclodextrin. An exemplary composition may comprise nanoparticles comprising PLA-PEG, an active/therapeutic agent, about 4 wt % to about 6 wt % (e.g. about 5 wt %) sucrose, and about 8 to about 12 weight percent (e.g. about 10 wt %) HPbCD.

In one aspect, a lyophilized pharmaceutical composition is provided comprising disclosed nanoparticles, wherein upon reconstitution of the lyophilized pharmaceutical composition at a nanoparticle concentration of about 50 mg/mL, in less than or about 100 mL of an aqueous medium, the reconstituted composition suitable for parenteral administration comprises less than 6000, such as less than 3000, microparticles of greater than or equal to 10 microns; and/or less than 600, such as less than 300, microparticles of greater than or equal to 25 microns.

The number of microparticles can be determined by means such as the USP 32 <788> by light obscuration particle count test, the USP 32 <788> by microscopic particle count test, laser diffraction, and single particle optical sensing.

In an aspect, a pharmaceutical composition suitable for parenteral use upon reconstitution is provided comprising a plurality of therapeutic particles each comprising a copolymer having a hydrophobic polymer segment and a hydrophilic polymer segment; an active agent; a sugar; and a cyclodextrin.

For example, the copolymer may be poly(lactic) acid-block-poly(ethylene)glycol copolymer. Upon reconstitution, a 100 mL aqueous sample may comprise less than 6000 particles having a size greater than or equal to 10 microns; and less than 600 particles having a size greater than or equal to 25 microns.

The step of adding a disaccharide and an ionic halide salt may comprise adding about 5 to about 15 weight percent sucrose or about 5 to about 20 weight percent trehalose (e.g., about 10 to about 20 weight percent trehalose), and about 10 to about 500 mM ionic halide salt. The ionic halide salt may be selected from sodium chloride, calcium chloride, and zinc chloride, or mixtures thereof. In an embodiment, about 1 to about 25 weight percent cyclodextrin is also added.

In another embodiment, the step of adding a disaccharide and a cyclodextrin may comprise adding about 5 to about 15 weight percent sucrose or about 5 to about 20 weight percent trehalose (e.g., about 10 to about 20 weight percent trehalose), and about 1 to about 25 weight percent cyclodextrin. In an embodiment, about 10 to about 15 weight percent cyclodextrin is added. The cyclodextrin may be selected from α-cyclodextrin, β-cyclodextrin, γ-cyclodextrin, or mixtures thereof.

In another aspect, a method of preventing substantial aggregation of particles in a pharmaceutical nanoparticle composition is provided comprising adding a sugar and a salt to the lyophilized formulation to prevent aggregation of the nanoparticles upon reconstitution. In an embodiment, a cyclodextrin is also added to the lyophilized formulation. In yet another aspect, a method of preventing substantial aggregation of particles in a pharmaceutical nanoparticle composition is provided comprising adding a sugar and a cyclodextrin to the lyophilized formulation to prevent aggregation of the nanoparticles upon reconstitution.

A contemplated lyophilized composition may have a therapeutic particle concentration of greater than about 40 mg/mL. The formulation suitable for parenteral administration may have less than about 600 particles having a size greater than 10 microns in a 10 mL dose. Lyophilizing may comprise freezing the composition at a temperature of greater than about −40° C., or e.g. less than about −30° C., forming a frozen composition; and drying the frozen composition to form the lyophilized composition. The step of drying may occur at about 50 mTorr at a temperature of about −25 to about −34° C., or about −30 to about −34° C.

Further features of the invention comprise a lyophilized pharmaceutical composition comprising a plurality of therapeutic nanoparticles and one or more pharmaceutically-acceptable excipients, wherein each therapeutic nanoparticle corresponds to one of the formulations of the Examples referred to as formulations E, F1, F2, G1 and G2 herein. Still further features of the invention comprise a lyophilized pharmaceutical composition comprising a plurality of therapeutic nanoparticles and one or more pharmaceutically-acceptable excipients, wherein each therapeutic nanoparticle corresponds to one of the formulations of the Examples referred to as formulations E, F1, F2, G1 and G2 herein, wherein the % by weight of AZD1152 hqpa and/or the % by weight of hydrophobic acid varies by +/−about 1% by weight (and so the amount of polymer varies accordingly). Still further features of the invention comprise a lyophilized pharmaceutical composition comprising a plurality of therapeutic nanoparticles and one or more pharmaceutically-acceptable excipients, wherein each therapeutic nanoparticle corresponds to one of the formulations of the Examples referred to as formulations E, F1, F2, G1 and G2 herein, but wherein the % by weight of AZD1152 hqpa and/or the % by weight of hydrophobic acid varies by +/−about 1.5% by weight (and so the amount of polymer varies accordingly) from that described in the Examples. Still further features of the invention comprise a lyophilized pharmaceutical composition comprising a plurality of therapeutic nanoparticles and one or more pharmaceutically-acceptable excipients, wherein each therapeutic nanoparticle corresponds to one of the of the Examples referred to as formulations E, F1, F2, G1 and G2 herein, but wherein the % by weight of AZD1152 hqpa and/or the % by weight of hydrophobic acid varies by +/−about 2% by weight (and so the amount of polymer varies accordingly) from that described in the Examples. Still further features of the invention comprise a lyophilized pharmaceutical composition comprising a plurality of therapeutic nanoparticles and one or more pharmaceutically-acceptable excipients, wherein each therapeutic nanoparticle corresponds to one of the of the Examples referred to as formulations E, F1, F2, G1 and G2 herein, but wherein the % by weight of AZD1152 hqpa varies by up to about +/−3% by weight, the amount of hydrophobic acid varies in proportion to the amount of AZD1152 hqpa corresponding to the proportions in the Exemplified formulations herein and so the amount of polymer varies accordingly.

In a further aspect there is provided a lyophilized pharmaceutical composition comprising a plurality of therapeutic nanoparticles and one or more pharmaceutically-acceptable excipients, wherein each therapeutic nanoparticle comprises about 15 to about 25% by weight of AZD1152 hqpa, about 7 to about 15% by weight of pamoic acid, and a diblock poly(lactic) acid-poly(ethylene)glycol copolymer (wherein the therapeutic nanoparticle comprises about 10 to about 30 weight percent poly(ethylene)glycol and the poly (lactic) acid-poly(ethylene)glycol copolymer has a number average molecular weight of about 16 kDa poly(lactic acid) and a number average molecular weight of about 5 kDa poly(ethylene)glycol).

In a further aspect there is provided a lyophilized pharmaceutical composition comprising a plurality of therapeutic nanoparticles and one or more pharmaceutically-acceptable excipients, wherein each therapeutic nanoparticle comprises about 15 to about 22% by weight of AZD1152 hqpa, about 7 to about 15% by weight of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol).

In a further aspect there is provided a lyophilized pharmaceutical composition comprising a plurality of therapeutic nanoparticles and one or more pharmaceutically-acceptable excipients, wherein each therapeutic nanoparticle comprises about 15 to about 22% by weight of AZD1152 hqpa, about 7 to about 15% by weight of pamoic acid, and about 63 to about 78 weight percent of a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol).

In a further aspect there is provided a lyophilized pharmaceutical composition comprising a plurality of therapeutic nanoparticles and one or more pharmaceutically-acceptable excipients, wherein each therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and a mixture of about 15 to about 22% by weight of AZD1152 hqpa and about 7 to about 15% by weight of pamoic acid.

In a further aspect there is provided a lyophilized pharmaceutical composition comprising a plurality of therapeutic nanoparticles and one or more pharmaceutically-acceptable excipients, wherein each therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and the product obtained by interaction of about 15 to about 22% by weight of AZD1152 hqpa and about 7 to about 15% by weight of pamoic acid.

In a further aspect there is provided a lyophilized pharmaceutical composition comprising a plurality of therapeutic nanoparticles and one or more pharmaceutically-acceptable excipients, wherein each therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol) and a hydrophobic ion pair formed between about 15 to about 22% by weight (of the nanoparticle) of AZD1152 hqpa and about 7 to about 15% by weight (of the nanoparticle) of pamoic acid.

In a further aspect there is provided a lyophilized pharmaceutical composition comprising a plurality of therapeutic nanoparticles and one or more pharmaceutically-acceptable excipients, wherein each therapeutic nanoparticle comprises about 15 to about 22% by weight of AZD1152 hqpa, about 7 to about 15% by weight of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol); wherein less than 20% of the AZD1152 hqpa is released from the nanoparticle after 30 hours in PBS and polysorbate20 at 37° C. In another embodiment of this aspect, less than 20% of the AZD1152 hqpa is released from the nanoparticle after 40 hours in PBS and polysorbate20 at 37° C. In another embodiment of this aspect, less than 20% of the AZD1152 hqpa is released from the nanoparticle after 50 hours in PBS and polysorbate20 at 37° C. Conveniently, the release of AZD1152 hqpa from the nanoparticle is measured using the method described hereinbefore.

In a further aspect there is provided a lyophilized pharmaceutical composition comprising a plurality of therapeutic nanoparticles and one or more pharmaceutically-acceptable excipients, wherein each therapeutic nanoparticle comprises about 15 to about 22% by weight of AZD1152 hqpa, about 7 to about 15% by weight of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene)glycol); wherein less than 20% of the AZD1152 hqpa is released from the nanoparticle after 30 hours in PBS and polysorbate20 at 37° C., and wherein the nanoparticles are made by a process comprising the following steps:

1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6 and the pamoic acid and AZD1152 hqpa are added at an initial ratio of 0.8 moles pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;

2) emulsifying the second phase to form a coarse emulsion;

3) holding the coarse emulsion for a hold time (such as 10 to 15 minutes, conveniently at about 0° C. for example by immersing in an ice-bath);

4) forming a nano-emulsion using a high pressure homogenizer;

5) optionally waiting for a delay time of at least 5 minutes, for example 10 minutes;

6) quenching of the emulsion phase at 0-5° C. thereby forming a quenched phase, wherein quenching of the emulsion phase comprises mixing the emulsion phase with a second aqueous solution comprising a buffer at pH 6.5 (such as a 0.17M phosphate buffer) wherein the ratio of second aqueous solution to emulsion is between about 2:1 and about 10:1, such as about 3:1;

7) adding an aqueous surfactant solution (such as polysorbate 80 sold under the trademark Tween®80, for example a 35 weight percent polysorbate 80 sold under the trademark Tween®80 solution in water) to the quench solution (for example at a ratio of about 20:1 polysorbate 80 sold under the trademark Tween®80 to drug by weight);

8) concentrating and isolating the resulting nanoparticles by filtration.

Suitably, nanoparticles in the above pharmaceutical compositions have a hydrodynamic diameter of <200 nm, such as 70-140 nm.

In a further aspect, a kit of parts is provided, which kit comprises:
1) a lyophilized pharmaceutical composition comprising disclosed nanoparticles as described hereinbefore; and
2) instructions for use.

In a further aspect, a kit of parts is provided, which kit comprises:
1) a freeze-dried pharmaceutical composition comprising disclosed nanoparticles as described hereinbefore; and
2) instructions for use.

Methods of Treatment

In some embodiments, contemplated nanoparticles may be used to treat, alleviate, ameliorate, relieve, delay onset of, inhibit progression of, reduce severity of, and/or reduce incidence of one or more symptoms or features of a disease, disorder, and/or condition. In some embodiments, contemplated nanoparticles may be used to treat solid tumors, e.g., cancer and/or cancer cells.

The term "cancer" includes pre-malignant as well as malignant cancers Cancers include, but are not limited to, haematological (blood) (e.g., chronic myelogenous leukemia, chronic myelomonocytic leukemia, Philadelphia chromosome positive acute lymphoblastic leukemia, mantle cell lymphoma, acute myeloid leukemia, diffuse large B cell lymphoma, myeloma, peripheral T-cell lymphoma, myelodysplastic syndrome), prostate, gastric cancer, colorectal cancer, skin cancer, e.g., melanomas or basal cell carcinomas, lung cancer (e.g., non-small cell lung cancer (NSCLC), small cell lung cancer (SCLC)), breast cancer, ovarian cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer (e.g., hepatocellular carcinoma), kidney cancer (e.g., renal cell carcinoma), testicular cancer, biliary tract cancer, small bowel or appendix cancer, gastrointestinal stromal tumor, salivary gland cancer, thyroid gland cancer, adrenal gland cancer, osteosarcoma, chondrosarcoma, cancer of hematological tissues, and the like. "Cancer cells" can be in the form of a tumor (a solid tumor), exist alone within a subject (e.g., leukemia cells), or be cell lines derived from a cancer.

In one aspect, the cancer to be treated is a leukemia. In another aspect the cancer to be treated is a haematological cancer. In another aspect the cancer to be treated is a haematological cancer such as AML. In another aspect the cancer to be treated is a haematological cancer such as DLBCL. In another aspect the cancer to be treated is a haematological cancer such as myelodysplastic syndrome.

In another aspect the cancer to be treated is a solid tumour. In another aspect, the cancer to be treated is NSCLC. In another aspect, the cancer to be treated is SCLC. In another aspect, the cancer to be treated is ovarian. In another aspect, the cancer to be treated is colorectal.

In one aspect the nanoparticles of the invention are used to treat highly proliferative cancer types.

Patients may be selected using biomarkers which may indicate a higher likelihood of benefiting from this treatment. For example, because their tumour has cells with a high rate of proliferation (for example due to high c-myc expression or amplification) or dysregulated apoptotic function (for example due to Bcl-2 gene translocation).

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect, a method for the treatment of cancer is provided. In some embodiments, the treatment of cancer comprises administering a therapeutically effective amount of inventive particles to a subject in need thereof, in such amounts and for such time as is necessary to achieve the desired result. In certain embodiments, a "therapeutically effective amount" of an inventive particle is that amount effective for treating, alleviating, ameliorating, relieving, delaying onset of, inhibiting progression of, reducing severity of, and/or reducing incidence of one or more symptoms or features of cancer.

Therefore, according to one aspect of the invention, there is provided a method for the prevention or treatment of cancer in a warm blooded animal, such as man in need thereof, comprising administering to the patient a therapeutically effective amount of a composition comprising a therapeutic nanoparticle comprising AZD1152 hqpa.

In one aspect, a method for administering inventive compositions to a subject suffering from cancer is provided. In some embodiments, nanoparticles may be administered to a subject in such amounts and for such time as is necessary to achieve the desired result (treatment of cancer). In certain embodiments, a "therapeutically effective amount" of a contemplated nanoparticle is that amount effective for treating, alleviating, ameliorating, relieving, delaying onset of, inhibiting progression of, reducing severity of, and/or reducing incidence of one or more symptoms or features of cancer.

In a further feature of the invention, there is provided a therapeutic nanoparticle comprising AZD1152 hqpa for use as a medicament in a warm-blooded animal such as man.

In a further feature of the invention, there is provided a therapeutic nanoparticle comprising AZD1152 hqpa for use in the production of an anti-proliferative effect in a warm-blooded animal such as man.

According to a further feature of this aspect of the invention there is provided a therapeutic nanoparticle comprising AZD1152 hqpa for use in a warm-blooded animal such as man as an anti-invasive agent in the containment and/or treatment of solid tumour disease.

In a further feature of the invention, there is provided the use of a therapeutic nanoparticle comprising AZD1152 hqpa in the prevention or treatment of cancer in a warm blooded animal such as man.

In a further feature of the invention, there is provided a therapeutic nanoparticle comprising AZD1152 hqpa for use in the prevention or treatment of cancer in a warm blooded animal such as man.

In a further feature of the invention, there is provided the use of a therapeutic nanoparticle comprising AZD1152 hqpa in the manufacture of a medicament for the prevention or treatment of cancer in a warm blooded animal such as man.

In one aspect of the above features, the cancer is a solid tumour. In another aspect of these features, the cancer is a leukemia.

According to a further aspect of the invention, there is provided the use of a therapeutic nanoparticle comprising AZD1152 hqpa for the production of an anti-proliferative effect in a warm-blooded animal such as man.

According to a further feature of this aspect of the invention there is provided the use of a therapeutic nanoparticle comprising AZD1152 hqpa in the manufacture of a medicament for use in the production of an anti-proliferative effect in a warm-blooded animal such as man.

According to a further feature of this aspect of the invention there is provided the use of a therapeutic nanoparticle comprising AZD1152 hqpa in the manufacture of a medicament for use in a warm-blooded animal such as man as an anti-invasive agent in the containment and/or treatment of solid tumour disease.

According to a further feature of this aspect of the invention there is provided a method for producing an anti-proliferative effect in a warm blooded animal, such as man, in need of such treatment which comprises administering to said animal an effective amount of a therapeutic nanoparticle comprising AZD1152 hqpa.

According to a further feature of this aspect of the invention there is provided a method for producing an anti-invasive effect by the containment and/or treatment of solid tumour disease in a warm blooded animal, such as man, in need of such treatment which comprises administering to said animal an effective amount of a therapeutic nanoparticle comprising AZD1152 hqpa.

According to a further aspect of the invention, there is provided a therapeutic nanoparticle comprising AZD1152 hqpa for use in the prevention or treatment of solid tumour disease in a warm blooded animal such as man.

According to a further aspect of the invention there is provided the use of a therapeutic nanoparticle comprising AZD1152 hqpa in the manufacture of a medicament for use in the prevention or treatment of solid tumour disease in a warm blooded animal such as man.

According to a further feature of this aspect of the invention there is provided a method for the prevention or treatment of solid tumour disease in a warm blooded animal, such as man, in need of such treatment which comprises administering to said animal an effective amount of a therapeutic nanoparticle comprising AZD1152 hqpa.

In the above uses and methods, conveniently 100 mg to 2000 mg of AZD1152 hqpa is administered on (for example) days 1 and 3, days 1 and 5 or days 1 and 7 of a seven day treatment cycle. The cycle may be repeated every week, two weeks or three weeks in a monthly or bi-monthly treatment cycle.

In the above uses and methods, suitably the therapeutic nanoparticle comprising AZD1152 hqpa is administered in the form of a pharmaceutical composition, such as those listed in 1) to 16):

1) a pharmaceutical composition comprising a plurality of therapeutic nanoparticles and one or more pharmaceutically-acceptable excipients, diluents and/or carriers, wherein each therapeutic nanoparticle comprises AZD1152 hqpa and optionally further comprises a hydrophobic acid;

2) a pharmaceutical composition comprising a plurality of therapeutic nanoparticles and one or more pharmaceutically-acceptable excipients, diluents and/or carriers, wherein each therapeutic nanoparticle comprises AZD1152 hqpa, a suitable polymer and optionally further comprises a hydrophobic acid;

3) a pharmaceutical composition comprising a plurality of therapeutic nanoparticles and one or more pharmaceutically-acceptable excipients, diluents and/or carriers, wherein each therapeutic nanoparticle comprises AZD1152 hqpa, a suitable polymer and further comprises a hydrophobic acid; in these aspects, conveniently the hydrophobic acid is selected from deoxycholic acid, cholic acid, dioctyl sulfosuccinic acid and pamoic acid; conveniently the hydrophobic acid may be a mixture of deoxycholic acid and cholic acid;

4) a pharmaceutical composition comprising a plurality of therapeutic nanoparticles and one or more pharmaceutically-acceptable excipients, diluents and/or carriers, wherein each therapeutic nanoparticle comprises AZD1152 hqpa, a diblock poly(lactic) acid-poly(ethylene)glycol copolymer and further comprises a hydrophobic acid. In these aspects, conveniently the hydrophobic acid is selected from deoxycholic acid, cholic acid, dioctyl sulfosuccinic acid and pamoic acid; conveniently the hydrophobic acid may be a mixture of deoxycholic acid and cholic acid;

5) a pharmaceutical composition comprising a plurality of therapeutic nanoparticles and one or more pharmaceutically-acceptable excipients, diluents and/or carriers, wherein each therapeutic nanoparticle comprises about 35 to about 94.75 weight percent of a diblock poly(lactic) acid-poly(ethylene) glycol copolymer, wherein the therapeutic nanoparticle comprises about 10 to about 30 weight percent poly(ethylene)glycol, about 0.05 to about 35 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 30 weight percent of AZD1152 hqpa or a pharmaceutically acceptable salt thereof;

6) a pharmaceutical composition comprising a plurality of therapeutic nanoparticles and one or more pharmaceutically-acceptable excipients, diluents and/or carriers, wherein each therapeutic nanoparticle comprises about 65 to about 90 weight percent of a diblock poly(lactic) acid-poly(ethylene) glycol copolymer, wherein the therapeutic nanoparticle comprises about 10 to about 30 weight percent poly(ethylene)glycol, about 5 to about 15 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 20 weight percent of AZD1152 hqpa or a pharmaceutically acceptable salt thereof;

7) a pharmaceutical composition comprising a plurality of therapeutic nanoparticles and one or more pharmaceutically-acceptable excipients, diluents and/or carriers, wherein each therapeutic nanoparticle comprises about 35 to about 94 weight percent of a diblock poly(lactic) acid-poly(ethylene) glycol copolymer, wherein the therapeutic nanoparticle comprises about 10 to about 30 weight percent poly(ethylene)glycol, about 1 to about 35 weight percent of pamoic acid and about 5 to about 30 weight percent of AZD1152 hqpa or a pharmaceutically acceptable salt thereof;

8) a pharmaceutical composition comprising a plurality of therapeutic nanoparticles and one or more pharmaceutically-acceptable excipients, diluents and/or carriers, wherein each therapeutic nanoparticle comprises about 55 to about 80 weight percent of a diblock poly(lactic) acid-poly(ethylene) glycol copolymer, wherein the therapeutic nanoparticle comprises about 10 to about 30 weight percent poly(ethylene)glycol, about 10 to about 20 weight percent of pamoic acid and about 10 to about 25 weight percent of AZD1152 hqpa or a pharmaceutically acceptable salt thereof;

9) a pharmaceutical composition comprising a plurality of therapeutic nanoparticles and one or more pharmaceutically-acceptable excipients, diluents and/or carriers, wherein each therapeutic nanoparticle comprises about 65 to about 76 weight percent of a diblock poly(lactic) acid-poly(ethylene) glycol copolymer, wherein the therapeutic nanoparticle comprises about 10 to about 20 weight percent poly(ethylene)glycol, about 9 to about 15 weight percent of pamoic acid and about 15 to about 20 weight percent of AZD1152 hqpa or a pharmaceutically acceptable salt thereof;

10) a pharmaceutical composition comprising a plurality of therapeutic nanoparticles and one or more pharmaceutically-acceptable excipients, diluents and/or carriers, wherein each therapeutic nanoparticle comprises about 15 to about 25 weight percent of AZD1152 hqpa, about 7 to about 15 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol);

11) a pharmaceutical composition comprising a plurality of therapeutic nanoparticles and one or more pharmaceutically-acceptable excipients, diluents and/or carriers, wherein each therapeutic nanoparticle comprises about 15 to about 22 weight percent of AZD1152 hqpa, about 7 to about 15 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol);

12) a pharmaceutical composition comprising a plurality of therapeutic nanoparticles and one or more pharmaceutically-acceptable excipients, diluents and/or carriers, wherein each therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol) and a mixture of about 15 to about 22 weight percent of AZD1152 hqpa and about 7 to about 15 weight percent of pamoic acid;

13) a pharmaceutical composition comprising a plurality of therapeutic nanoparticles and one or more pharmaceutically-acceptable excipients, diluents and/or carriers, wherein each therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol) and the product obtained by interaction of about 15 to about 22 weight percent of AZD1152 hqpa and about 7 to about 15 weight percent of pamoic acid;

14) a pharmaceutical composition comprising a plurality of therapeutic nanoparticles and one or more pharmaceutically-acceptable excipients, diluents and/or carriers, wherein each therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol) and a hydrophobic ion pair formed between about 15 to about 22 weight percent (of the nanoparticle) of AZD1152 hqpa and about 7 to about 15 weight percent (of the nanoparticle) of pamoic acid;

15) a pharmaceutical composition comprising a plurality of therapeutic nanoparticles and one or more pharmaceutically-acceptable excipients, diluents and/or carriers, wherein each therapeutic nanoparticle comprises about 15 to about 22 weight percent of AZD1152 hqpa, about 7 to about 15 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol); wherein less than 20% of the AZD1152 hqpa is released from the nanoparticle after 30 hours in PBS and polysorbate20 at 37° C. Conveniently, the release of AZD1152 hqpa from the nanoparticle is measured using the method described hereinbefore.

16) a pharmaceutical composition comprising a plurality of therapeutic nanoparticles and one or more pharmaceutically-acceptable excipients, diluents and/or carriers, wherein each therapeutic nanoparticle comprises about 15 to about 22 weight percent of AZD1152 hqpa, about 7 to about 15 weight percent of pamoic acid, and a diblock poly(lactic) acid-copolymer (wherein the therapeutic nanoparticle comprises about 10 to about 30 weight percent poly(ethylene) glycol and the poly(lactic) acid-poly(ethylene)glycol copolymer has a number average molecular weight of about 16 kDa poly(lactic acid) and a number average molecular weight of about 5 kDa poly(ethylene)glycol); wherein less than 20% of the AZD1152 hqpa is released from the nanoparticle after 30 hours in PBS and polysorbate20 at 37° C., and wherein the nanoparticles are made by a process comprising the following steps:

1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6 and the pamoic acid and AZD1152 hqpa are added at an initial ratio of 0.8 moles pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;

2) emulsifying the second phase to form a coarse emulsion;

3) holding the coarse emulsion for a hold time (such as 10 to 15 minutes, conveniently at about 0° C. for example by immersing in an ice-bath);

4) forming a nano-emulsion using a high pressure homogenizer;

5) optionally waiting for a delay time of at least 5 minutes, for example 10 minutes;

6) quenching of the emulsion phase at 0-5° C. thereby forming a quenched phase, wherein quenching of the emulsion phase comprises mixing the emulsion phase with a second aqueous solution comprising a buffer at pH 6.5 (such as a 0.17M phosphate buffer) wherein the ratio of second aqueous solution to emulsion is between about 2:1 and about 10:1, such as about 3:1;

7) adding an aqueous surfactant solution (such as polysorbate 80 sold under the trademark Tween®80, for example a 35 weight percent polysorbate 80 sold under the trademark Tween®80 solution in water) to the quench solution (for example at a ratio of about 20:1 polysorbate 80 sold under the trademark Tween®80 to drug by weight);

8) concentrating and isolating the resulting nanoparticles by filtration.

In the pharmaceutical compositions described above for use in the above uses and methods, conveniently the co-polymer has a number average molecular weight of about 16 kDa poly(lactic acid) and a number average molecular weight of about 5 kDa poly(ethylene)glycol.

In the above uses and methods suitably the therapeutic nanoparticle comprising AZD1152 hqpa is administered in the form of a pharmaceutical composition comprising one of the formulations of the Examples referred to as formulations E, F1, F2, G1 and G2 herein and one or more pharmaceutically-acceptable excipients, diluents and/or carriers. Also suitable for use in the above methods and uses are therapeutic nanoparticles comprising AZD1152 hqpa administered in the form of a pharmaceutical composition comprising a formulation described in the Examples as formulations E, F1, F2, G1 and G2 herein, but wherein the % by weight of AZD1152 hqpa and/or the % by weight of hydrophobic acid varies by +/−about 1% by weight (and so the amount of polymer varies accordingly) from that described in the Examples, and one or more pharmaceutically-acceptable excipients, diluents and/or carriers. Also suitable for use in the above methods and uses are therapeutic nanoparticles comprising AZD1152 hqpa administered in the form of a pharmaceutical composition comprising a formulation described in the Examples as formulations E, F1, F2, G1 and G2 herein, but wherein the % by weight of AZD1152 hqpa and/or the % by weight of hydrophobic acid varies by +/−about 1.5% by weight (and so the amount of polymer varies accordingly) from that described in the Examples and one or more pharmaceutically-acceptable excipients, diluents and/or carriers. Also suitable for use in the above methods and uses are therapeutic nanoparticles comprising AZD1152 hqpa administered in the form of a pharmaceutical composition comprising a formulation described in the Examples as formulations E, F1, F2, G1 and G2 herein, but wherein the % by weight of AZD1152 hqpa and/or the % by weight of hydrophobic acid varies by +/−about 2% by weight (and so the amount of polymer varies accordingly) from that described in the Examples and one or more pharmaceutically-acceptable excipients, diluents and/or carriers. Still further features of the invention comprise a pharmaceutical composition comprising a plurality of therapeutic nanoparticles and one or more pharmaceutically-acceptable excipients, diluents and/or carriers, wherein each therapeutic nanoparticle corresponds to one of the of the Examples referred to as formulations E, F1, F2, G1 and G2 herein, but wherein the % by weight of AZD1152 hqpa varies by up to about +/−3% by weight, the amount of hydrophobic acid varies in proportion to the amount of AZD1152 hqpa corresponding to the proportions in the Exemplified formulations herein and so the amount of polymer varies accordingly.

In some of the above aspects, the therapeutic nanoparticles may comprise about 50 to about 99.75 weight percent of a diblock poly(lactic) acid-poly(ethylene)glycol copolymer or a diblock poly(lactic acid-co-glycolic acid)-poly(ethylene)glycol copolymer, wherein the therapeutic nanoparticle comprises about 10 to about 30 weight percent poly(ethylene)glycol, and optionally further comprise a substantially hydrophobic acid as defined herein, such as cholic acid, deoxycholic acid or dioctyl sulfosuccinic acid (particularly deoxycholic acid, dioctyl sulfosuccinic acid or a mixture of deoxycholic acid and cholic acid).

Inventive therapeutic protocols involve administering a therapeutically effective amount of a contemplated nanoparticle to a healthy individual (i.e., a subject who does not display any symptoms of cancer and/or who has not been diagnosed with cancer). For example, healthy individuals may be "immunized" with a contemplated nanoparticle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course, individuals known to have cancer may receive inventive treatment at any time.

In other embodiments, disclosed nanoparticles can be used to inhibit the growth of cancer cells, e.g., lung cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Also provided herein are methods of administering to a patient a nanoparticle disclosed herein including an active agent, wherein, upon administration to a patient, such nanoparticles substantially reduces the volume of distribution and/or substantially reduces free $C_{max}$, as compared to administration of the agent alone (i.e., not as a disclosed nanoparticle).

The nanoparticles of the present invention may be administered to a patient as a sole therapy or may be administered in combination (simultaneous or sequential) with conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); topoisomerase inhibitors (for example epipodophyllotoxins like etoposide and teniposide, amsacrine, topotecan and camptothecin); and others such as therapeutic antibodies (for example rituximab);

(ii) antihormonal agents such as antioestrogens (for example tamoxifen, fulvestrant, toremifene, raloxifene, droloxifene and iodoxyfene), progestogens (for example megestrol acetate), aromatase inhibitors (for example as anastrozole, letrozole, vorazole and exemestane);

(iii) inhibitors of growth factor function and their downstream signalling pathways: included are Ab modulators of any growth factor or growth factor receptor targets, reviewed by Stern et al. (Critical Reviews in Oncology/Haematology, 2005, 54, pp 11-29); also included are small molecule inhibitors of such targets, for example kinase inhibitors—examples include the anti-erbB2 antibody trastuzumab [Herceptin™ ], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R;

also included are modulators which target signalling proteins in the PI3-kinase signaling pathway, for example, inhibitors of PI3-kinase isoforms such as PI3K-α/β/γ and ser/thr kinases such as AKT, mTOR, PDK, SGK, PI4K or PIP5K; also included are inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, Syk inhibitors such as fostamatinib, inhibitors of other ser/thr kinases such as JAKs, STATs and IRAK4, and cyclin dependent kinase inhibitors;

iv) modulators of DNA damage signalling pathways, for example PARP inhibitors (e.g. Olaparib), ATR inhibitors or ATM inhibitors and modulators of the cell cycle, for example CDK4 and CDK6 inhibitors (eg palbociclib);

v) modulators of apoptotic and cell death pathways such as Bcl family modulators (e.g. ABT-263/Navitoclax, ABT-199);

(vi) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as sorafenib, axitinib, pazopanib, sunitinib and vandetanib (and compounds that work by other mechanisms (for example linomide, inhibitors of integrin αvβ3 function and angiostatin)];

(vii) vascular damaging agents, such as Combretastatin A4;

(viii) anti-invasion agents, for example c-Src kinase family inhibitors like (dasatinib, J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558), PDL-1 (eg MEDI4736 see U.S. Pat. No. 8,779,108) or CTLA4 (e.g. ipilimumab and tremelimumab);

(x) Antisense or RNAi based therapies, for example those which are directed to the targets listed.

(xi) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

In one embodiment there is provided a combination suitable for use in the treatment of cancer comprising nanoparticles of the present invention as defined herein and another anti-tumour agent selected from i-a), iv-a) and ix-a) as defined below, wherein i-a) is a subset of i) above, iv-a) is a subset of iv) above and ix-a) is a subset of ix) above, and wherein:

i-a) comprises standard-of-care chemotherapy regimens, including but not limited to replacing or augmenting antimitotic chemotherapies in solid tumour and haematological cancers, such as taxanes and *vinca* alkaloids;

iv-a) comprises therapies that target the DNA damage response, including but not limited to agents that inhibit DNA damage repair and the cell cycle; and ix-a) comprises immune-mediated therapies, including but not limited to inhibitors of the immune checkpoint blockade such as CTLA4, PD-1 and PDL-1 targeted therapies.

According to this aspect of the invention there is provided a combination suitable for use in the treatment of cancer comprising nanoparticles of the present invention as defined herein and another anti-tumour agent, in particular any one of the anti tumour agents listed under (i)-(xi) above. In particular, the anti-tumour agent listed under (i)-(xi) above is the standard of care for the specific cancer to be treated; the person skilled in the art will understand the meaning of "standard of care".

Therefore in a further aspect of the invention there is provided nanoparticles of the present invention as disclosed herein in combination with another anti-tumour agent, in particular an anti-tumour agent selected from one listed under (i)-(xi), such as i-a), iv-a) or ix-a), herein above. For example, the nanoparticles of the invention for use in the combination with an anti-tumour agent selected from one listed under (i)-(xi) herein above, such as i-a), iv-a) or ix-a), may be provided as a pharmaceutical composition selected from 1) to 16) below:

1) a pharmaceutical composition comprising a plurality of therapeutic nanoparticles and one or more pharmaceutically-acceptable excipients, diluents and/or carriers, wherein each therapeutic nanoparticle comprises AZD1152 hqpa and optionally further comprises a hydrophobic acid;

2) a pharmaceutical composition comprising a plurality of therapeutic nanoparticles and one or more pharmaceutically-acceptable excipients, diluents and/or carriers, wherein each therapeutic nanoparticle comprises AZD1152 hqpa, a suitable polymer and optionally further comprises a hydrophobic acid;

3) a pharmaceutical composition comprising a plurality of therapeutic nanoparticles and one or more pharmaceutically-acceptable excipients, diluents and/or carriers, wherein each therapeutic nanoparticle comprises AZD1152 hqpa, a suitable polymer and further comprises a hydrophobic acid;

in these aspects, conveniently the hydrophobic acid is selected from deoxycholic acid, cholic acid, dioctyl sulfosuccinic acid and pamoic acid; conveniently the hydrophobic acid may be a mixture of deoxycholic acid and cholic acid;

4) a pharmaceutical composition comprising a plurality of therapeutic nanoparticles and one or more pharmaceutically-acceptable excipients, diluents and/or carriers, wherein each therapeutic nanoparticle comprises AZD1152 hqpa, a diblock poly(lactic) acid-poly(ethylene)glycol copolymer and further comprises a hydrophobic acid. In these aspects, conveniently the hydrophobic acid is selected from deoxycholic acid, cholic acid, dioctyl sulfosuccinic acid and pamoic acid; conveniently the hydrophobic acid may be a mixture of deoxycholic acid and cholic acid;

5) a pharmaceutical composition comprising a plurality of therapeutic nanoparticles and one or more pharmaceutically-acceptable excipients, diluents and/or carriers, wherein each therapeutic nanoparticle comprises about 35 to about 94.75 weight percent of a diblock poly(lactic) acid-poly(ethylene) glycol copolymer, wherein the therapeutic nanoparticle comprises about 10 to about 30 weight percent poly(ethylene)glycol, about 0.05 to about 35 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 30 weight percent of AZD1152 hqpa or a pharmaceutically acceptable salt thereof;

6) a pharmaceutical composition comprising a plurality of therapeutic nanoparticles and one or more pharmaceutically-acceptable excipients, diluents and/or carriers, wherein each therapeutic nanoparticle comprises about 65 to about 90 weight percent of a diblock poly(lactic) acid-poly(ethylene) glycol copolymer, wherein the therapeutic nanoparticle comprises about 10 to about 30 weight percent poly(ethylene)glycol, about 5 to about 15 weight percent of a substantially hydrophobic acid selected from the group consisting of deoxycholic acid, cholic acid, a mixture of cholic and deoxycholic acid, dioctyl sulfosuccinic acid and pamoic acid, and about 5 to about 20 weight percent of AZD1152 hqpa or a pharmaceutically acceptable salt thereof;

7) a pharmaceutical composition comprising a plurality of therapeutic nanoparticles and one or more pharmaceutically-acceptable excipients, diluents and/or carriers, wherein each therapeutic nanoparticle comprises about 35 to about 94 weight percent of a diblock poly(lactic) acid-poly(ethylene) glycol copolymer, wherein the therapeutic nanoparticle comprises about 10 to about 30 weight percent poly(ethylene)glycol, about 1 to about 35 weight percent of pamoic acid and about 5 to about 30 weight percent of AZD1152 hqpa or a pharmaceutically acceptable salt thereof;

8) a pharmaceutical composition comprising a plurality of therapeutic nanoparticles and one or more pharmaceutically-acceptable excipients, diluents and/or carriers, wherein each therapeutic nanoparticle comprises about 55 to about 80 weight percent of a diblock poly(lactic) acid-poly(ethylene) glycol copolymer, wherein the therapeutic nanoparticle comprises about 10 to about 30 weight percent poly(ethylene)glycol, about 10 to about 20 weight percent of pamoic acid and about 10 to about 25 weight percent of AZD1152 hqpa or a pharmaceutically acceptable salt thereof;

9) a pharmaceutical composition comprising a plurality of therapeutic nanoparticles and one or more pharmaceutically-acceptable excipients, diluents and/or carriers, wherein each therapeutic nanoparticle comprises about 65 to about 76 weight percent of a diblock poly(lactic) acid-poly(ethylene) glycol copolymer, wherein the therapeutic nanoparticle comprises about 10 to about 20 weight percent poly(ethylene)glycol, about 9 to about 15 weight percent of pamoic acid and about 15 to about 20 weight percent of AZD1152 hqpa or a pharmaceutically acceptable salt thereof;

10) a pharmaceutical composition comprising a plurality of therapeutic nanoparticles and one or more pharmaceutically-acceptable excipients, diluents and/or carriers, wherein each therapeutic nanoparticle comprises about 15 to about 25 weight percent of AZD1152 hqpa, about 7 to about 15 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol);

11) a pharmaceutical composition comprising a plurality of therapeutic nanoparticles and one or more pharmaceutically-acceptable excipients, diluents and/or carriers, wherein each therapeutic nanoparticle comprises about 15 to about 22 weight percent of AZD1152 hqpa, about 7 to about 15 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol);

12) a pharmaceutical composition comprising a plurality of therapeutic nanoparticles and one or more pharmaceutically-acceptable excipients, diluents and/or carriers, wherein each therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol) and a mixture of about 15 to about 22 weight percent of AZD1152 hqpa and about 7 to about 15 weight percent of pamoic acid;

13) a pharmaceutical composition comprising a plurality of therapeutic nanoparticles and one or more pharmaceutically-acceptable excipients, diluents and/or carriers, wherein each therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol) and the product obtained by interaction of about 15 to about 22 weight percent of AZD1152 hqpa and about 7 to about 15 weight percent of pamoic acid;

14) a pharmaceutical composition comprising a plurality of therapeutic nanoparticles and one or more pharmaceutically-acceptable excipients, diluents and/or carriers, wherein each therapeutic nanoparticle comprises a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol) and a hydrophobic ion pair formed between about 15 to about 22 weight percent (of the nanoparticle) of AZD1152 hqpa and about 7 to about 15 weight percent (of the nanoparticle) of pamoic acid;

15) a pharmaceutical composition comprising a plurality of therapeutic nanoparticles and one or more pharmaceutically-acceptable excipients, diluents and/or carriers, wherein each therapeutic nanoparticle comprises about 15 to about 22 weight percent of AZD1152 hqpa, about 7 to about 15% by weight of pamoic acid, and a diblock poly(lactic) acid-poly (ethylene)glycol copolymer (wherein the therapeutic nanoparticle comprises about 10 to about 30 weight percent poly(ethylene)glycol and the poly(lactic) acid-poly(ethylene)glycol copolymer has a number average molecular weight of about 16 kDa poly(lactic acid) and a number average molecular weight of about 5 kDa poly(ethylene) glycol); wherein less than 20% of the AZD1152 hqpa is released from the nanoparticle after 30 hours in PBS and polysorbate20 at 37° C. Conveniently, the release of AZD1152 hqpa from the nanoparticle is measured using the method described hereinbefore.

16) a pharmaceutical composition comprising a plurality of therapeutic nanoparticles and one or more pharmaceutically-acceptable excipients, diluents and/or carriers, wherein each therapeutic nanoparticle comprises about 15 to about 22 weight percent of AZD1152 hqpa, about 7 to about 15 weight percent of pamoic acid, and a diblock poly(lactic) acid-poly(ethylene)glycol copolymer (wherein the therapeutic nanoparticle comprises about 10 to about 30 weight percent poly(ethylene)glycol and the poly(lactic) acid-poly (ethylene)glycol copolymer has a number average molecular weight of about 16 kDa poly(lactic acid) and a number average molecular weight of about 5 kDa poly(ethylene) glycol); wherein less than 20% of the AZD1152 hqpa is released from the nanoparticle after 30 hours in PBS and polysorbate20 at 37° C., and wherein the nanoparticles are made by a process comprising the following steps:

1) combining a first organic phase (which comprises a 16:5 PLA-PEG co-polymer, AZD1152 hqpa and pamoic acid in a solvent mixture comprising TFA, benzyl alcohol, DMSO and ethyl acetate such that the benzyl alcohol:ethyl acetate are present in a molar ratio of about 1:3.6 and the pamoic acid and AZD1152 hqpa are added at an initial ratio of 0.8 moles pamoic acid: 1 mole AZD1152 hqpa) with a first aqueous solution (comprising a polyoxyethylene (100) stearyl ether sold under the trademark Brij® S100, in water, DMSO and benzyl alcohol) to form a second phase, wherein the ratio of the aqueous phase to the organic phase is about 5.5:1;

2) emulsifying the second phase to form a coarse emulsion;

3) holding the coarse emulsion for a hold time (such as 10 to 15 minutes, conveniently at about 0° C. for example by immersing in an ice-bath);

4) forming a nano-emulsion using a high pressure homogenizer;

5) optionally waiting for a delay time of at least 5 minutes, for example 10 minutes;

6) quenching of the emulsion phase at 0-5° C. thereby forming a quenched phase, wherein quenching of the emulsion phase comprises mixing the emulsion phase with a second aqueous solution comprising a buffer at pH 6.5 (such as a 0.17M phosphate buffer) wherein the ratio of second aqueous solution to emulsion is between about 2:1 and about 10:1, such as about 3:1;

7) adding an aqueous surfactant solution (such as polysorbate 80 sold under the trademark Tween®80, for example a 35% w/w polysorbate 80 sold under the trademark Tween®80 solution in water) to the quench solution (for example at a ratio of about 20:1 polysorbate 80 sold under the trademark Tween®80 to drug by weight);

8) concentrating and isolating the resulting nanoparticles by filtration.

Other suitable pharmaceutical compositions comprising AZD1152 hqpa in a nanoparticle described herein may also be used in the above combinations.

Further aspects of the invention are set out in the following features:

1. A therapeutic nanoparticle comprising:
   about 50 to about 99.75 weight percent of a diblock poly(lactic) acid-poly(ethylene)glycol copolymer or a diblock poly(lactic acid-co-glycolic acid)-poly(ethylene)glycol copolymer, wherein the therapeutic nanoparticle comprises about 10 to about 30 weight percent poly(ethylene)glycol; and
   about 0.2 to about 30 weight percent of AZD1152 hqpa or a pharmaceutically acceptable salt thereof.

2. The therapeutic nanoparticle of feature 1, wherein the poly(lactic) acid-poly(ethylene)glycol copolymer has a poly(lactic) acid number average molecular weight fraction of about 0.7 to about 0.9.

3. The therapeutic nanoparticle of feature 1, wherein the poly(lactic) acid-poly(ethylene)glycol copolymer has a poly(lactic) acid number average molecular weight fraction of about 0.75 to about 0.85.

4. The therapeutic nanoparticle of feature 1, 2 or 3, wherein the therapeutic nanoparticle comprises about 10 to about 25 weight percent poly(ethylene)glycol.
5. The therapeutic nanoparticle of feature 1, 2 or 3, wherein the therapeutic nanoparticle comprises about 20 to about 30 weight percent poly(ethylene)glycol.
6. The therapeutic nanoparticle of any preceding feature, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.
7. The therapeutic nanoparticle of feature 6, wherein the poly(lactic) acid-poly(ethylene)glycol copolymer has a number average molecular weight of about 16 kDa poly(lactic acid) and a number average molecular weight of about 5 kDa poly(ethylene)glycol.
8. The therapeutic nanoparticle of any one of features 1-6, comprising about 65 weight percent to about 85 weight percent of the copolymer.
9. The therapeutic nanoparticle of any one of features 1-8, further comprising a substantially hydrophobic acid.
10. The therapeutic nanoparticle of any one of features 1-8, further comprising about 0.05 to about 35 weight percent of a substantially hydrophobic acid.
11. The therapeutic nanoparticle of any one of features 1-8, further comprising about 5 to about 15 weight percent of a substantially hydrophobic acid.
12. The therapeutic nanoparticle of any one of features 1-8, further comprising about 10 to about 20 weight percent of a substantially hydrophobic acid.
13. The therapeutic nanoparticle of any one of features 9 to 12, wherein the hydrophobic acid is a bile acid.
14. The therapeutic nanoparticle of feature 13, wherein the bile acid is deoxycholic acid, cholic acid or a mixture thereof.
15. The therapeutic nanoparticle of any one of features 9 to 12, wherein the hydrophobic acid is dioctyl sulfosuccinic acid.
16. The therapeutic nanoparticle of any one of features 9 to 12, wherein the hydrophobic acid is pamoic acid.
17. The therapeutic nanoparticle of any one of features 9-12, wherein the molar ratio of the substantially hydrophobic acid to the therapeutic agent is about 0.5:1 to about 1.6:1, wherein the acid is deoxycholic acid, cholic acid or a mixture of cholic acid and deoxycholic acid.
18. The therapeutic nanoparticle of any one of features 9-12, wherein the molar ratio of the substantially hydrophobic acid to AZD1152 hqpa is about 1.3:1 to about 1.6:1, wherein the acid is a mixture of cholic acid and deoxycholic acid.
19. The therapeutic nanoparticle of any one of features 9-12, wherein the molar ratio of the substantially hydrophobic acid to AZD1152 hqpa is about 0.9:1 to about 1.1:1, wherein the acid is dioctyl sulfosuccinic acid.
20. The therapeutic nanoparticle of any one of features 9-15, wherein a $pK_a$ of AZD1152 hqpa is at least about 1.0 $pK_a$ units greater than a $pK_a$ of the hydrophobic acid.
21. The therapeutic nanoparticle of any one of features 9-19, wherein the substantially hydrophobic acid and AZD1152 hqpa form a hydrophobic ion pair in the therapeutic nanoparticle.
22. The therapeutic nanoparticle of any one of features 1-21, comprising about 5 to about 20 weight percent of AZD1152 hqpa.
23. The therapeutic nanoparticle of any one of features 1-21, comprising about 10 to about 20 weight percent of AZD1152 hqpa.
24. A therapeutic nanoparticle comprising: about 50 to about 99.75 weight percent of a diblock poly(lactic) acid-poly(ethylene)glycol copolymer, wherein the therapeutic nanoparticle comprises about 10 to about 30 weight percent poly(ethylene)glycol; about 5 to about 30 weight percent of a therapeutic agent which is AZD1152 hqpa or a pharmaceutically acceptable salt thereof; and either about 0.05 to about 35 weight percent of a substantially hydrophobic acid selected from the group consisting of deoxycholic acid, cholic acid and dioctyl sulfosuccinic acid; or about 0.05 to about 35 weight percent of a mixture of substantially hydrophobic acids which are deoxycholic acid and cholic acid.
25. A therapeutic nanoparticle comprising: about 50 to about 99.75 weight percent of a diblock poly(lactic) acid-poly(ethylene)glycol copolymer, wherein the therapeutic nanoparticle comprises about 10 to about 30 weight percent poly(ethylene)glycol; about 5 to about 30 weight percent of a therapeutic agent which is AZD1152 hqpa or a pharmaceutically acceptable salt thereof; and either about 0.05 to about 35 weight percent of a substantially hydrophobic acid selected from the group consisting of deoxycholic acid, cholic acid and dioctyl sulfosuccinic acid; or about 0.05 to about 35 weight percent of a mixture of substantially hydrophobic acids which are deoxycholic acid and cholic acid.
26. A therapeutic nanoparticle comprising: about 35 to about 94.75 weight percent of a diblock poly(lactic) acid-poly(ethylene)glycol copolymer, wherein the therapeutic nanoparticle comprises about 10 to about 30 weight percent poly(ethylene)glycol; about 0.05 to about 35 weight percent of a substantially hydrophobic acid selected from the group consisting of deoxycholic acid, cholic acid, (or a mixture of cholic and deoxycholic acid), dioctyl sulfosuccinic acid and pamoic acid; and about 5 to about 30 weight percent of AZD1152 hqpa or a pharmaceutically acceptable salt thereof.
27. A therapeutic nanoparticle comprising: about 65 to about 90 weight percent of a diblock poly(lactic) acid-poly(ethylene)glycol copolymer, wherein the therapeutic nanoparticle comprises about 10 to about 30 weight percent poly(ethylene)glycol; about 5 to about 15 weight percent of a substantially hydrophobic acid selected from the group consisting of deoxycholic acid, cholic acid, (or a mixture of cholic and deoxycholic acid), dioctyl sulfosuccinic acid and pamoic acid; and about 5 to about 20 weight percent of AZD1152 hqpa or a pharmaceutically acceptable salt thereof.
28. The therapeutic nanoparticle of feature 24, feature 25, feature 26 or feature 27 wherein the poly(lactic) acid-poly(ethylene)glycol copolymer has a poly(lactic) acid number average molecular weight fraction of about 0.7 to about 0.9.
29. The therapeutic nanoparticle of feature 24, feature 25, feature 26 or feature 27 wherein the poly(lactic) acid-poly(ethylene)glycol copolymer has a poly(lactic) acid number average molecular weight fraction of about 0.75 to about 0.85.
30. The therapeutic nanoparticle of feature 24, feature 25, feature 26 or feature 27 wherein the therapeutic nanoparticle comprises about 10 to about 25 weight percent poly(ethylene)glycol.

31. The therapeutic nanoparticle of feature 24, feature 25, feature 26 or feature 27 wherein the therapeutic nanoparticle comprises about 20 to about 30 weight percent poly(ethylene)glycol.
32. The therapeutic nanoparticle of any of features 24 to 31, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.
33. The therapeutic nanoparticle of any of features 24 to 31, wherein the poly(lactic) acid-poly(ethylene)glycol copolymer has a number average molecular weight of about 16 kDa poly(lactic acid) and a number average molecular weight of about 5 kDa poly(ethylene)glycol.
34. The therapeutic nanoparticle of any one of features 24-33, comprising about 65 weight percent to about 85 weight percent of the copolymer.
35. A pharmaceutically acceptable composition comprising a plurality of therapeutic nanoparticles of any one of features 1-34 and a pharmaceutically acceptable excipient.
36. A method of treating cancer in a patient in need thereof, comprising administering to the patient a therapeutically effective amount of a composition comprising the therapeutic nanoparticle of any one of features 1-34.
37. The method of feature 36, wherein the cancer is lung cancer.
38. The method of feature 36, wherein the cancer is a leukemia.
39. The method of feature 36, wherein the cancer is colorectal cancer.

Further aspects of the invention are set out in the following features:

1a. A therapeutic nanoparticle comprising: about 50 to about 99.75 weight percent of a diblock poly(lactic) acid-poly(ethylene)glycol copolymer or a diblock poly(lactic acid-co-glycolic acid)-poly(ethylene)glycol copolymer, wherein the therapeutic nanoparticle comprises about 10 to about 30 weight percent poly(ethylene)glycol; and about 0.2 to about 30 weight percent of AZD1152 hqpa or a pharmaceutically acceptable salt thereof.
2a. The therapeutic nanoparticle of feature 1a, wherein the poly(lactic) acid-poly(ethylene)glycol copolymer has a poly(lactic) acid number average molecular weight fraction of about 0.7 to about 0.9.
3a. The therapeutic nanoparticle of feature 1a, wherein the poly(lactic) acid-poly(ethylene)glycol copolymer has a poly(lactic) acid number average molecular weight fraction of about 0.75 to about 0.85.
4a. The therapeutic nanoparticle of feature 1a, wherein the therapeutic nanoparticle comprises about 10 to about 25 weight percent poly(ethylene)glycol.
5a. The therapeutic nanoparticle of feature 1a, wherein the therapeutic nanoparticle comprises about 20 to about 30 weight percent poly(ethylene)glycol.
6a. The therapeutic nanoparticle of feature 1a, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.
7a. The therapeutic nanoparticle of feature 6a, wherein the poly(lactic) acid-poly(ethylene)glycol copolymer has a number average molecular weight of about 16 kDa poly(lactic acid) and a number average molecular weight of about 5 kDa poly(ethylene)glycol.
8a. The therapeutic nanoparticle of any one of features 1a-6a, comprising about 65 weight percent to about 85 weight percent of the copolymer.
9a. The therapeutic nanoparticle of any one of features 1a-8a, further comprising a substantially hydrophobic acid.
10a. The therapeutic nanoparticle of any one of features 1a-8a, further comprising about 0.05 to about 35 weight percent of a substantially hydrophobic acid.
11a. The therapeutic nanoparticle of any one of features 1a-8a, further comprising about 5 to about 15 weight percent of a substantially hydrophobic acid.
12a. The therapeutic nanoparticle of any one of features 1a-8a, further comprising about 10 to about 20 weight percent of a substantially hydrophobic acid.
13a. The therapeutic nanoparticle of any one of features 9a-12a, wherein the molar ratio of the substantially hydrophobic acid to the therapeutic agent is about 0.5:1 to about 1.6:1, wherein the acid is deoxycholic acid, cholic acid or a mixture of cholic acid and deoxycholic acid.
14a. The therapeutic nanoparticle of any one of features 9a-12a, wherein the molar ratio of the substantially hydrophobic acid to the therapeutic agent is about 1.3:1 to about 1.6:1, wherein the acid is a mixture of cholic acid and deoxycholic acid.
15a. The therapeutic nanoparticle of any one of features 9a-12a, wherein the molar ratio of the substantially hydrophobic acid to the therapeutic agent is about 0.9:1 to about 1.1:1, wherein the acid is dioctyl sulfosuccinic acid.
16a. The therapeutic nanoparticle of any one of features 9a-15a, wherein a $pK_a$ of the therapeutic agent is at least about 1.0 $pK_a$ units greater than a $pK_a$ of the hydrophobic acid.
17a. The therapeutic nanoparticle of any one of features 9a-16a, wherein the substantially hydrophobic acid and the therapeutic agent form a hydrophobic ion pair in the therapeutic nanoparticle.
18a. The therapeutic nanoparticle of any one of features 9a-17a, wherein the hydrophobic acid is a bile acid.
19a. The therapeutic nanoparticle of feature 18a, wherein the bile acid is deoxycholic acid, cholic acid or a mixture thereof.
20a. The therapeutic nanoparticle of any one of features 9a-18a, wherein the hydrophobic acid is dioctyl sulfosuccinic acid.
21a. The therapeutic nanoparticle of any one of features 1a-20a, comprising about 5 to about 20 weight percent of the therapeutic agent.
22a. The therapeutic nanoparticle of any one of features 1a-20a, comprising about 10 to about 20 weight percent of the therapeutic agent.
23a. A therapeutic nanoparticle comprising: about 50 to about 99.75 weight percent of a diblock poly(lactic) acid-poly(ethylene)glycol copolymer, wherein the therapeutic nanoparticle comprises about 10 to about 30 weight percent poly(ethylene)glycol; about 5 to about 30 weight percent of a therapeutic agent which is AZD1152 hqpa or a pharmaceutically acceptable salt thereof; and either about 0.05 to about 35 weight percent of a substantially hydrophobic acid selected from the group consisting of deoxycholic acid, cholic acid and dioctyl sulfosuccinic acid; or about 0.05 to about 35 weight percent of a mixture of substantially hydrophobic acids which are deoxycholic acid and cholic acid.
24a. The therapeutic nanoparticle of feature 23a, wherein the poly(lactic) acid-poly(ethylene)glycol copolymer has a 25a. The therapeutic nanoparticle of feature 23a, wherein the poly(lactic) acid-poly(ethylene)glycol copolymer has a poly(lactic) acid number average molecular weight fraction of about 0.75 to about 0.85.

26a. The therapeutic nanoparticle of feature 23a, wherein the therapeutic nanoparticle comprises about 10 to about 25 weight percent poly(ethylene)glycol.

27a. The therapeutic nanoparticle of feature 23a, wherein the therapeutic nanoparticle comprises about 20 to about 30 weight percent poly(ethylene)glycol.

28a. The therapeutic nanoparticle of feature 23a, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.

29a. The therapeutic nanoparticle of feature 28a, wherein the poly(lactic) acid-poly(ethylene)glycol copolymer has a number average molecular weight of about 16 kDa poly(lactic acid) and a number average molecular weight of about 5 kDa poly(ethylene)glycol.

30a. The therapeutic nanoparticle of any one of features 23a-29a, comprising about 65 weight percent to about 85 weight percent of the copolymer.

31a. A pharmaceutically acceptable composition comprising a plurality of therapeutic nanoparticles of any one of features 1a-30a and a pharmaceutically acceptable excipient.

32a. A method of treating cancer in a patient in need thereof, comprising administering to the patient a therapeutically effective amount of a composition comprising the therapeutic nanoparticle of any one of features 1a-30a.

33a. The method of feature 32a, wherein the cancer is lung cancer.

34a. The method of feature 32a, wherein the cancer is a leukemia.

35a. The method of feature 32a, wherein the cancer is colorectal cancer.

EXAMPLES

The invention now being generally described, it will be more readily understood by reference to the following examples which are included merely for purposes of illustration of certain aspects and embodiments, and are not intended to limit the invention in any way.

Each of the following examples provides a separate independent aspect of the invention. In particular, the formulations disclosed in the following examples and the methods disclosed for making them comprise separate independent aspects of the invention.

AZD1152 hqpa may be made as described in WO2004/058781 or WO2007/132210.

ABBREVIATIONS

The following abbreviations may be used.
EA ethyl acetate
BA benzyl alcohol
DI de-ionised
TFF tangential flow filtration
TFA trifluoroacetic acid
Lyo/oven lyophilizing oven
DMSO dimethylsulfoxide
scid severe compromised immunodeficient
polyoxyethylene (100) stearyl ether sold under the tradename Brij® 100 is a surfactant commercially available polyoxyethylene (100) stearyl ether with an average molecular weight of about 4670, chemical abstracts (CAS) number 9005-00-9 polysorbate 80 sold under the trademark Tween®80 A commercially available polyoxyethylene sorbitan monooleate, also known as polysorbate 80, CAS number 9005-65-6
sorbitane monooleate sold under the trademark Span®80 A commercially available sorbitan monooleate, CAS number 1338-43-8

For the avoidance of doubt, where "polymer-PEG" is referred to in the following examples, it means PLA-PEG co-polymer where the co-polymer has a number average molecular weight of about 16 kDa poly(lactic acid) and a number average molecular weight of about 5 kDa poly(ethylene)glycol. Such polymers are commercially available or may be made by methods known in the art. Such polymers are used for example in WO2010/005721.

Example 1: Preparation of Therapeutic Nanoparticles Containing 2-(3-((7-(3-(ethyl(2-hydroxyethyl)amino)propoxy)quinazolin-4-yl)amino)-1H-pyrazol-5-yl)-N-(3-fluorophenyl)acetamide Using a Nanoemulsion Process This example demonstrates procedures for preparing nanoparticles containing AZD1152 hqpa.
Deoxycholic acid Nanoparticle Preparation Procedure
1. Preparation of polymer solution
   1.1 To 20 mL glass vial add polymer-PEG, 350 mg.
   1.2 Add 3.15 g of ethyl acetate to glass vial and vortex overnight to give a polymer-EA solution.
2. Preparation of drug solution 2.1 To make 9% deoxycholic acid/BA, add 1.8 g of deoxycholic acid into 18.2 g of BA in 20 ml scintillation vial based on the recipe table.
   2.2 Heat the solution at 80° C. for 30 mins.
   2.3 Weigh 150 mg of therapeutic agent in 20 ml scintillation vial.
   2.4 Add above 9% deoxycholic acid to the drug and leave at 80° C. for 15-30 mins to get clear drug solution.
   2.5 Right before formulation, combine drug and polymer solution.
3. Preparation of Aqueous Solution:
   0.475% Sodium Cholate, 4% Benzyl Alcohol in Water.
   3.1 To 1 L bottle add 4.75 g sodium cholate and 955.25 g of DI water and mix on stir plate until dissolved.
   3.2 Add 40 g of benzyl alcohol to sodium cholate/water and mix on stir plate until dissolved.
4. Formation of emulsion. Ratio of Aqueous phase to organic phase is 5:1
   4.1 Pour organic phase into aqueous solution and homogenize using hand-held rotor/stator homogenizer for 10 seconds at room temperature to form coarse emulsion.
   4.2 Feed solution through high pressure homogenizer (110S) with pressure set at ~11,000 psi on gauge for 1 discreet passes to form nanoemulsion.
5. Formation of nanoparticles
   Pour emulsion into Quench (D.I. water) at <5° C. while stirring on stir plate. Ratio of Quench to Emulsion is 10:1.
6. Add 35% (w/w) polysorbate 80 sold under the trademark Tween® 80 in water to quench at ratio of 100:1 polysorbate 80 sold under the trademark Tween® 80 to drug by weight.

7. Concentrate nanoparticles through TFF
7.1 Concentrate quench on TFF with 300 kDa Pall cassette (2×0.1 m² membranes) to ~200 mL.
7.2 Diafilter ~20 diavolumes (4 liter) using cold DI water.
7.3 Bring volume down to minimal volume.
7.4 Add 100 mL of cold water to vessel and pump through membrane to rinse.
7.5 Collect material in glass vial, ~100 mL.
8. Determination of solids concentration of unfiltered final slurry:
8.1 To tared 20 mL scintillation vial add a volume of final slurry and dry under vacuum on lyo/oven.
8.2 Determine weight of nanoparticles in the volume of slurry dried down.
9. Determination of solids concentration of 0.45 μm filtered final slurry:
9.1 Filter about a portion of the final slurry sample before addition of sucrose through 0.45 μm syringe filter.
9.2 To tared 20 mL scintillation vial add a volume of filtered sample and dry under vacuum on lyo/oven.
10. Add 1 part of sucrose to final 9 parts of slurry sample to attain 10% sucrose.
11. Freeze remaining sample of unfiltered final slurry with sucrose.

Docusate Nanoparticle Preparation Procedure
1. Preparation of polymer solution
1.1 To 20 mL glass vial add polymer-PEG, 750 mg.
1.2 Add 2.75 g of ethyl acetate to glass vial and vortex overnight to give a polymer-EA solution.
2. Preparation of drug solution
2.1 To make 30% docusate/benzyl alcohol ("30% docusate/BA"), use Table 1.
2.2 Weigh 250 mg of therapeutic agent in 20 ml scintillation vial.
2.3 Add above 690 mg of 30% docusate to the drug and vortex for more than 1 hr to get clear drug solution.
2.4 Right before formulation, add drug and polymer solution.

TABLE 1

Preparation of docusate/BA solution.

| Desired Conc (w/w) | Total Docusate + BA gram solution | Docusate-sodium Acid need (g) | BA to Add (g) | HCl (g) addition (5N) | Brine Needed (g) |
|---|---|---|---|---|---|
| 30% docusate/ in BA | 30.00% | 40.00 | 12.00 | 28.00 | 16.20 | 18.67 |

3. Preparation of Aqueous Solution:
0.475% Sodium Cholate, 4% Benzyl Alcohol in Water.
3.1 To 1 L bottle add 4.75 g sodium cholate and 955.25 g of DI water and mix on stir plate until dissolved.
3.2 Add 40 g of benzyl alcohol to sodium cholate/water and mix on stir plate until dissolved.
4. Formation of emulsion. Ratio of Aqueous phase to organic phase is 5:1
4.1 Pour organic phase into aqueous solution and homogenize using hand-held rotor/stator homogenizer for 10 seconds at room temperature to form coarse emulsion.
4.2 Feed solution through high pressure homogenizer (110S) with pressure set at ~11,000 psi on gauge for 1 discreet passes to form nanoemulsion.

5. Formation of nanoparticles
Pour emulsion into Quench (D.I. water) at <5° C. while stirring on stir plate. Ratio of Quench to Emulsion is 10:1.
6. Add 35% (w/w) polysorbate 80 sold under the trademark Tween® 80 in water to quench at ratio of 100:1 polysorbate 80 sold under the trademark Tween® 80 to drug by weight.
7. Concentrate nanoparticles through TFF
7.1 Concentrate quench on TFF with 300 kDa Pall cassette (2×0.1 m² membranes) to ~200 mL.
7.2 Diafilter ~20 diavolumes (4 liter) using cold DI water.
7.3 Bring volume down to minimal volume.
7.4 Add 100 mL of cold water to vessel and pump through membrane to rinse.
7.5 Collect material in glass vial, ~100 mL.
8. Determination of solids concentration of unfiltered final slurry:
8.1 To tared 20 mL scintillation vial add a volume of final slurry and dry under vacuum on lyo/oven.
8.2 Determine weight of nanoparticles in the volume of slurry dried down.
9. Determination of solids concentration of 0.45 μm filtered final slurry:
9.1 Filter about a portion of the final slurry sample before addition of sucrose through 0.45 μm syringe filter.
9.2 To tared 20 mL scintillation vial add a volume of filtered sample and dry under vacuum on lyo/oven.
10. Add 1 part of sucrose to final 9 parts of slurry sample to attain 10% sucrose.
11. Freeze remaining sample of unfiltered final slurry with sucrose.

In a variation on the above procedure, sodium docusate may be used in place of sodium cholate in step 3.1 above.

Example 2: Characterization of Therapeutic Nanoparticles Containing AZD1152 hqpa This example demonstrates that co-encapsulation with hydrophobic counter-ions such as deoxycholic acid and docusate greatly improved drug loading (from ~3% to up to ~15% drug loading). The release of therapeutic agent from nanoparticles was substantially slower when formulated as a hydrophobic ion pair compared to the control formulation.

Control Formulations

Control formulations were made as plain nanoparticles ("NPs") without any counter-ions. NPs were prepared using PLA-PEG polymer matrix (16 kDa PLA/5 kDa PEG) ("16/5 PLA-PEG") with no additional excipients.

Figure 3:
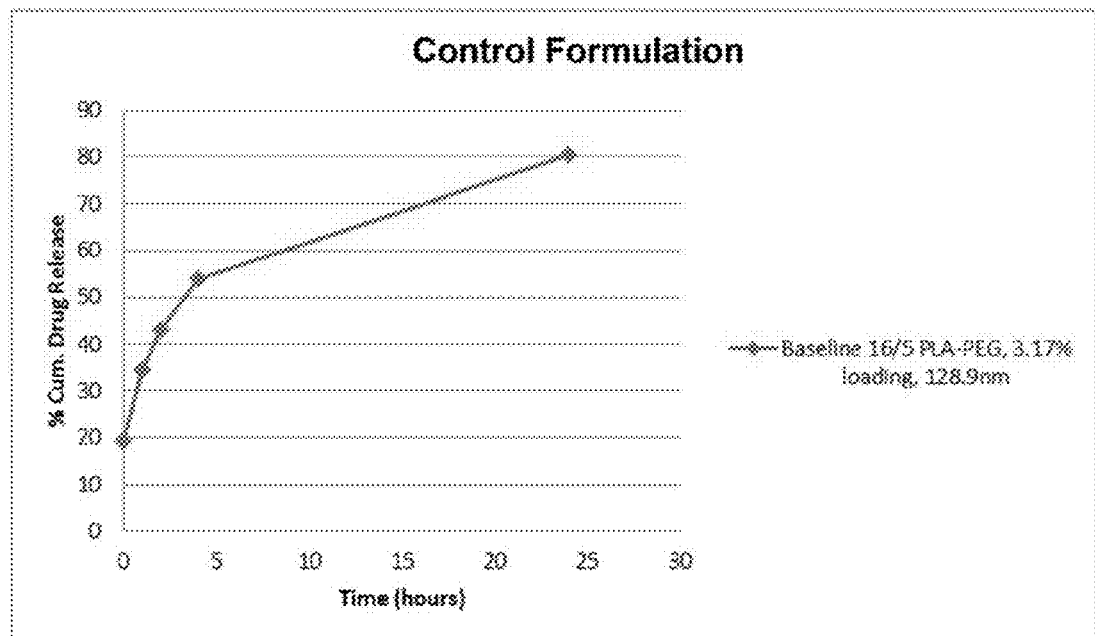
FIG. 3 depicts an in vitro release profile for control therapeutic nanoparticle formulations.

Therapeutic agent was dissolved in benzyl alcohol ("BA") or BA/water to form the drug solution, and polymer solution in ethyl acetate ("EA") was poured into the drug solution right before adding to aqueous for homogenization. This control formulation results in nanoparticles with relatively low drug loading (~3%), high burst (~20%), and fast release (>50% at 4 hrs). (See Table 1 and FIG. 3.) These results are not unusual for APIs with relatively low MW (<600 kDa) and/or lesser hydrophobicity (log P<3).

TABLE 2

Control nanoparticle formulation.

| Lot # | Drug theoretical loading | Organic phase solids concentration | Loading % | size (nm) |
|---|---|---|---|---|
| 16/5 PLA-PEG, 7.5% water in BA only | 20 | 7% | 3.17 | 128.9 (0.172) |

Deoxycholic Acid Formulations

Deoxycholic acid formulations were made according to the procedure in Example 1 using various amounts of deoxycholic acid in the organic phase as shown in Table 3. Nanoparticles were prepared using 16/5 PLA-PEG.

TABLE 3

Deoxycholic acid nanoparticle formulations.

| | Acid wt % | Total mass (g) | BA | Deoxycholic acid |
|---|---|---|---|---|
| 8% Deoxycholic Acid in BA | 8 | 20 | 18.4 g | 1.6 g |
| 9% Deoxycholic Acid in BA | 9 | 20 | 18.2 g | 1.8 g |
| 10% Deoxycholic Acid in BA | 10 | 20 | 18.0 g | 2.0 g |

Table 4 below provides characterization data for deoxycholic acid formulations. As evidenced by the data, the presence of the deoxycholic acid greatly enhances the API loading in the final nanoparticle formulations as compared to the control nanoparticles.

TABLE 4

Characterization data for formulations containing deoxycholic acid.

| Lot # | Theoretical drug loading (wt %) | Organic phase [solids]¹ (wt %) | Benzyl alcohol [deoxycholic acid] (wt %) | Acid:Drug addition ratio (mol:mol) | Ethyl acetate portion of organic solvents (wt %) | Actual drug loading (wt %) | Mean size by DLS (nm) |
|---|---|---|---|---|---|---|---|
| 254-14-1 | 20 | 15% | 9.0 | 0.99 | 70 | 10% | 99.6 |
| 254-20-1 | 20 | 15% | 9.0 | 0.99 | 70 | 9.90% | 105.6 |
| 254-14-2 | 20 | 15% | 8.0 | 1.02 | 65 | 7.30% | 84.5 |
| 254-20-2 | 20 | 15% | 8.0 | 1.02 | 65 | 8.20% | 127.7 |
| 254-20-3 | 30 | 15% | 13.5 | 0.99 | 70 | 10.00% | 104.7 |
| 254-20-4 | 20 | 15% | 8.0 | 0.99 | 70 | 9.40% | 102.3 |
| 254-20-5 | 25 | 10% | 7.0 | 0.98 | 70 | 10.50% | 135.4 |
| 254-20-6 | 25 | 10% | 7.0 | 0.98 | 70 | 10.00% | 105.4 |
| 254-20-7 | 30 | 10% | 9.0 | 1.05 | 70 | 11.70% | 110.3 |
| 254-20-8 | 30 | 10% | 9.0 | 1.05 | 70 | 11.20% | 112.6 |
| 254-20-9 | 30 | 10% | 10.0 | 0.97 | 75 | 11.40% | 107.6 |
| 254-20-10 | 30 | 10% | 10.0 | 0.97 | 75 | 11.20% | 107.4 |
| 254-32-1 | 30 | 10% | 9.0 | 1.05 | 70 | 9.60% | 111.4 |
| 254-34-1 | 35 | 10% | 8.0 | 1.06 | 60 | 6.40% | 136.8 |
| 254-34-2 | 35 | 10% | 8.0 | 1.06 | 60 | 7.90% | 119.4 |
| 254-34-3 | 35 | 12.5% | 8.0 | 1.03 | 50 | 7.40% | 111.1 |
| 254-38-1 | 35 | 10% | 8.0 | 1.06 | 60 | 7.40% | 117.6 |
| 254-38-2 | 35 | 10% | 8.0 | 1.06 | 60 | 7.80% | 117.3 |
| 254-38-3 | 35 | 10% | 8.0 | 1.06 | 60 | 7.70% | 124.0 |
| 254-38-4 | 35 | 10% | 8.0 | 1.06 | 60 | 8.70% | 120.9 |
| 254-38-5 | 30 | 15% | 10.0 | 0.98 | 60 | 7.60% | 141.1 |
| 254-38-6 | 30 | 15% | 10.0 | 0.98 | 60 | 9.10% | 121.1 |
| 254-38-7 | 30 | 15% | 10.0 | 0.98 | 60 | 8.30% | 150.3 |
| 254-38-8 | 30 | 15% | 10.0 | 0.98 | 60 | 10.40% | 127.0 |

¹This value = wt % concentration of drug + polymer divided by organic solids and does not include the deoxycholic acid for these batches.
DLS is dynamic light scattering.

Figure 4:
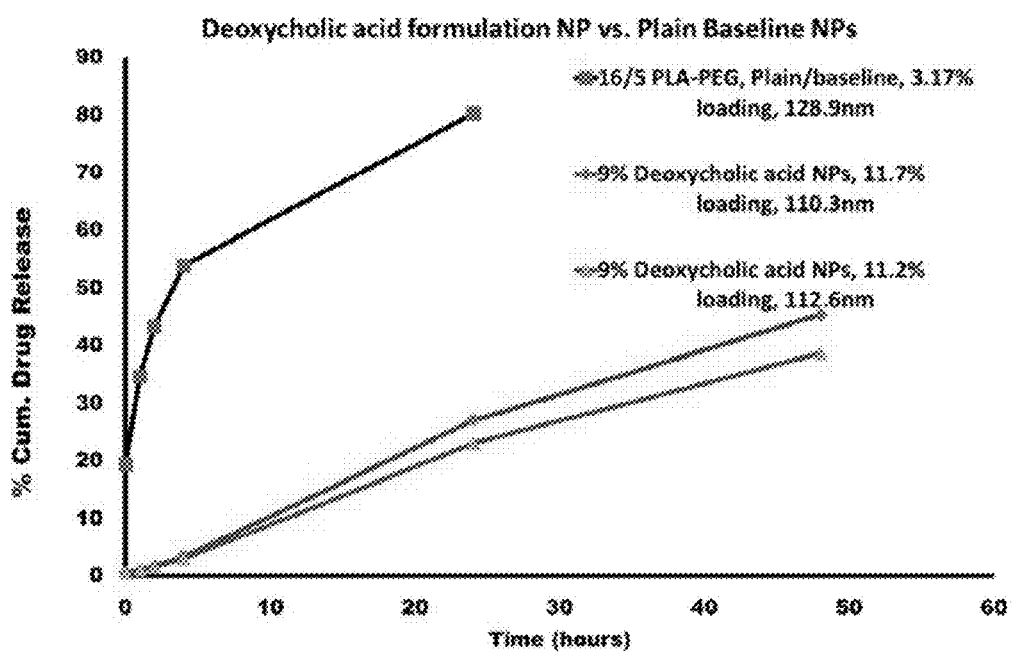
FIG. 4 depicts in vitro release profiles for deoxycholic acid nanoparticle formulations versus a control therapeutic nanoparticle formulation.

FIG. 4 shows in vitro therapeutic agent release showing controlled and slow/sustained release of drugs from deoxycholic acid NPs compared to that from control NPs without deoxycholic acid counter-ions.

The table below describes the composition (by percent weight) of each component in the particle of a particular nanoparticle formulation, which is referred to herein as "Formulation F1".

| Component | Weight Percent of the Nanoparticle |
|---|---|
| 16/5 PLA-PEG | 75% |
| Deoxycholic acid | 9% |
| Cholic acid | 6% |
| AZD1152 hqpa | 10% |

Docusate Formulations

Docusate sodium (eg available as "Aerosol OT" or "AOT") was converted into acid form (i.e., dioctyl sulfosuccinic acid) using an in-situ converting method before being mixed with drug. Docusate sodium was dissolved in BA, and concentrated HCl solution was added at controlled HCl/docusate ratios. The mixture was vortexed to facilitate proton exchange and conversion of the sodium salt to free acid form. Then, saturated sodium chloride solution was added and mixed by vortexing to extract water and sodium chloride salt formed in the BA mixture. After mixing, the sample was incubated at room temperature for phase separation. Over time, two layers gradually developed with BA on top and the aqueous layer on the bottom. The top layer was aspirated as drug solvent containing docusate counter ion. Concentrations of docusate acid in BA were reported as docusate sodium concentration in BA. Docusate nanoparticle formulations were prepared using the procedure in Example 1 with 16/5 PLA/PEG polymer as for the deoxycholic acid formulation. Typical docusate acid preparations are listed in Table 5.

TABLE 5

Typical preparations of protonated docusate sodium solution (DSS) in BA (as drug solvent).

| DSS % in BA | Material | Percent | Calculated amount Mass (g) | mMol | Molar ratio of HCl/docusate |
|---|---|---|---|---|---|
| 10% | BA | 90% | 60 | — | — |
| | Docusate | 10% | 6.7 | 15 | 3.33 |
| | 5N HCl | — | 10 | 50 | |
| | Saturated NaCl | — | 20 | — | — |
| 15% | BA | 85% | 60 | — | — |
| | docusate | 15% | 10.6 | 23.8 | 4.20 |
| | 5N HCl | — | 20 | 100 | |
| | Saturated NaCl | — | 40 | — | — |
| 20% | BA | 80% | 60 | — | — |
| | docusate | 20% | 15 | 33.7 | 5.93 |
| | 5N HCl | — | 40 | 200 | |
| | Saturated NaCl | — | 80 | — | — |

Table 6 below provides characterization data for representative docusate formulations. Without wishing to be bound by any theory, it is believed that the presence of the docusate counter ion serves to enhance drug encapsulation and loading by the hydrophobic ion pairing (HIP) process.

TABLE 6

Characterization data for formulations containing docusate acid.

| Lot # | Drug theoretical loading (wt %) | Organic phase [solids] (wt %) | [Docusate] % | Acid:Drug addition ratio (mol:mol) | EA % | Drug Loading wt % | Mean size (nm) |
|---|---|---|---|---|---|---|---|
| 250-80-5 | 20 | 18 | 20 | 1.09 | 80 | 8.89% | 100.2 |
| 250-80-6: | 20 | 18 | 20 | 1.09 | 80 | 10.95% | 96.6 |
| 250-80-7: | 30 | 18 | 20 | 1.09 | 70 | 13.75% | 113.2 |
| 250-80-8: | 30 | 18 | 20 | 1.09 | 70 | 16.25% | 132.1 |
| 250-110-1: | 25 | 22.5 | 30 | 0.99 | 80 | 13.80% | 116.8 |
| 250-110-2: | 25 | 22.5 | 30 | 0.99 | 80 | 15.22% | 135.6 |
| 250-110-3: | 20 | 18 | 20 | 1.09 | 80 | 9.92% | 117.4 |
| 250-110-4: | 20 | 18 | 20 | 1.09 | 80 | 11.45% | 139.2 |
| 250-110-5: | 20 | 18 | 20 | 1.09 | 80 | 10.52% | 114.8 |
| 250-110-6: | 25 | 25 | 25 | 0.90 | 75 | 7.17% | 104.8 |
| 250-110-7: | 25 | 25 | 25 | 0.90 | 75 | 6.01% | 92.7 |
| 250-110-1: | 25 | 22.5 | 30 | 0.99 | 80 | 13.80% | 116.8 |
| 250-130-1: | 25 | 22.5 | 30 | 0.99 | 80 | 8.49% | 104 |
| 250-130-2: | 25 | 22.5 | 30 | 1.06 | 80 | 10.10% | 125 |
| 250-130-3: | 35 | 22.5 | 30 | 1.06 | 70 | 13.39% | 120.8 |
| 250-130-4: | 35 | 22.5 | 30 | 1.06 | 70 | 14.41% | 124.7 |

TABLE 6-continued

Characterization data for formulations containing docusate acid.

| Lot # | Drug theoretical loading (wt %) | Organic phase [solids] (wt %) | [Docusate] % | Acid:Drug addition ratio (mol:mol) | EA % | Drug Loading wt % | Mean size (nm) |
|---|---|---|---|---|---|---|---|
| 250-130-6: | 35 | 22.5 | 30 | 1.06 | 70 | 4.61% | 85 |

Figure 5:
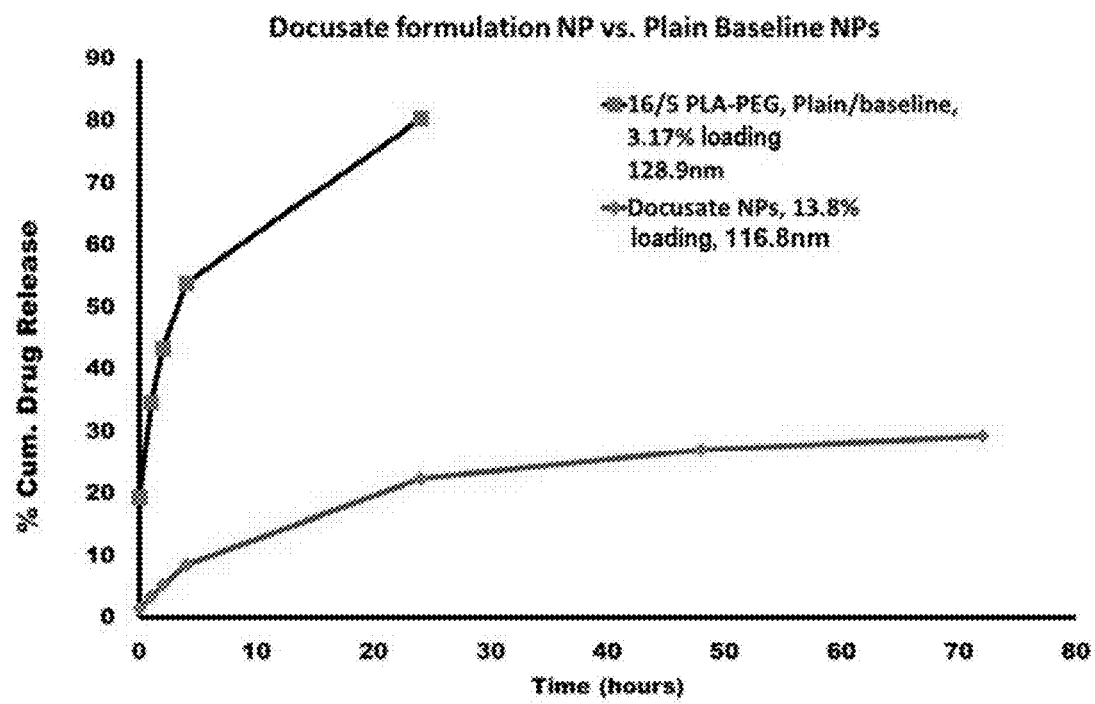
FIG. 5 depicts in vitro release profiles for a docusate acid nanoparticle formulation versus a control therapeutic nanoparticle formulation.

FIG. 5 shows in vitro therapeutic agent release showing controlled and slow/sustained release of drugs from docusate acid NPs compared to that from control NPs without docusate counter-ions.

The table below describes the composition (by percent weight) of each component in the particle of a particular nanoparticle formulation, which is referred to herein as "Formulation F2".

| Component | Weight Percent of the Nanoparticle |
|---|---|
| 16/5 PLA-PEG | 80% |
| Docusate | 10% |
| AZD1152 hqpa | 10% |

Example 3

A formulation containing cholic acid is described below. This formulation is referred to herein as "Formulation E".

| COMPONENT | Percent of particle mass (nominal) |
|---|---|
| AZD1152 hqpa | 5 |
| PLA-PEG 16/5 | 90 |
| Cholic acid | 5 |

Cholic Acid Nanoparticle Preparation Procedure
1. Preparation of polymer solution
   1.1 To 20 mL glass vial add polymer-PEG, 350 mg.
   1.2 Add 8.11 g of ethyl acetate to glass vial and vortex overnight to give a polymer-EA solution.
2. Preparation of drug solution
   2.1 To make 3% TFA/BA, add 63 mg of TFA into 2.03 g of BA in 20 ml scintillation vial based on the recipe table.
   2.2 Weigh 150 mg of therapeutic agent in 20 ml scintillation vial.
   2.3 Add above 3% TFA in BA to the drug and mix for 15-30 mins to get clear drug solution.
   2.4 Right before formulation, combine drug and polymer solution.
3. Preparation of Aqueous Solution:
   0.52% Sodium Cholate, 4% Benzyl Alcohol in Water.
   3.1 To 1 L bottle add 5.2 g sodium cholate and 954.8 g of DI water and mix on stir plate until dissolved.
   3.2 Add 40 g of benzyl alcohol to sodium cholate/water and mix on stir plate until dissolved.
4. Formation of emulsion. Ratio of Aqueous phase to Organic phase is 5:1
   4.1 Pour organic phase into aqueous solution and homogenize using hand-held rotor/stator homogenizer for 10 seconds at room temperature to form coarse emulsion.
   4.2 Feed solution through high pressure homogenizer (110S) with pressure set at ~11,000 psi on gauge for 1 discreet passes to form nanoemulsion.
5. Formation of nanoparticles
   Pour emulsion into Quench (D.I. water) at <5° C. while stirring on stir plate. Ratio of Quench to Emulsion is 10:1.
6. Add 35% (w/w) polysorbate 80 sold under the trademark Tween® 80 in water to quench at ratio of 100:1 polysorbate 80 sold under the trademark Tween® 80 to drug by weight.
7. Concentrate nanoparticles through TFF
   7.1 Concentrate quench on TFF with 300 kDa Pall cassette (2×0.1 m² membranes) to ~200 mL.
   7.2 Diafilter ~20 diavolumes (4 liter) using cold DI water.
   7.3 Bring volume down to minimal volume.
   7.4 Add 100 mL of cold water to vessel and pump through membrane to rinse.
   7.5 Collect material in glass vial, ~100 mL.
8. Determination of solids concentration of unfiltered final slurry:
   8.1 To tared 20 mL scintillation vial add a volume of final slurry and dry under vacuum on lyo/oven.
   8.2 Determine weight of nanoparticles in the volume of slurry dried down.
9. Determination of solids concentration of 0.45 µm filtered final slurry:
   9.1 Filter about a portion of the final slurry sample before addition of sucrose through 0.45 µm syringe filter.
   9.2 To tared 20 mL scintillation vial add a volume of filtered sample and dry under vacuum on lyo/oven.
10. Add 1 part of sucrose to final 9 parts of slurry sample to attain 10% sucrose by weight.
11. Freeze remaining sample of unfiltered final slurry with sucrose.

Example 4

A further formulation was prepared by a similar process to the dioctyl sulfosuccinic acid formulation processes in Example 1. This further formulation is detailed in the table below and is referred to herein as "Formulation B".

| COMPONENT | Percent of particle mass (nominal) |
|---|---|
| AZD1152 hqpa | 10 |
| PLA-PEG 16/5 | 85 |
| Oleic acid | 5 |

Example 5—Therapeutic Index

Data generated in the SW620 human tumour xenograft model in rat and mouse. The SW620-bearing female nude rat model is known to be susceptible to spontaneous tumour regressions which are more prevalent in longer duration xenograft studies and are not shown.

Rat Therapeutic Index Studies (SW620 in Female Nude Rat)

Female nude rats were bred at AstraZeneca, and put into study at a minimum weight of 150 g. Animals were inoculated in the flank with SW620 human tumour cells and dosing started when tumours had reached 0.4-0.9 cm³. Compounds were dosed intravenously (IV) at 5 ml/kg with either control, AZD1152 or AZD1152 hqpa nanoparticle formulation B or E. AZD1152 was dosed in tris buffer vehicle (days 1-4 IV, each dose at 25 mg/kg) and AZD1152 hqpa nanoparticle formulation was dosed in physiological saline (dosed 25 mg/kg on each of days 1 and 3 IV). At the time points indicated animals were sacrificed and tumour, blood and femur/bone marrow samples taken. Effects of the treatments on the tumour and the bone marrow were scored by a pathologist assessment of haematoxylin and eosin stained sections derived from the femur.

Figure 6B:
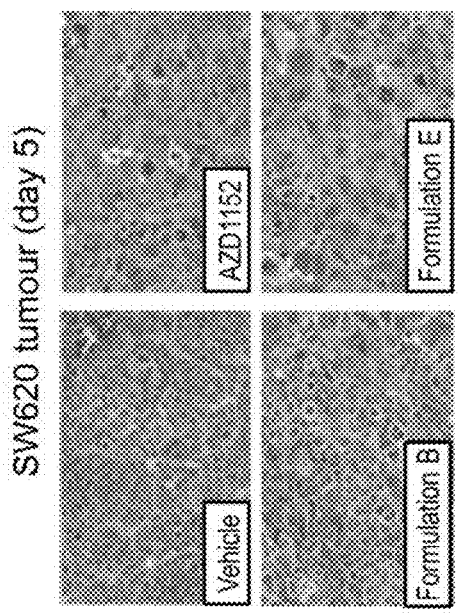
FIGS. 6A, 6B and 6C depict the results from SW620 human colorectal xenograft model in female nude rats.
Figure 6C:
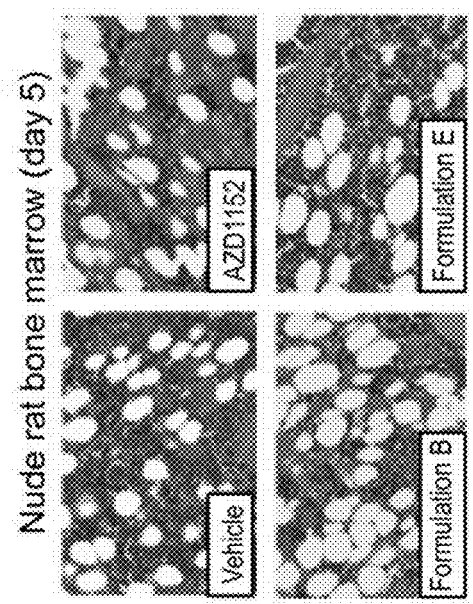
Figure 6A:
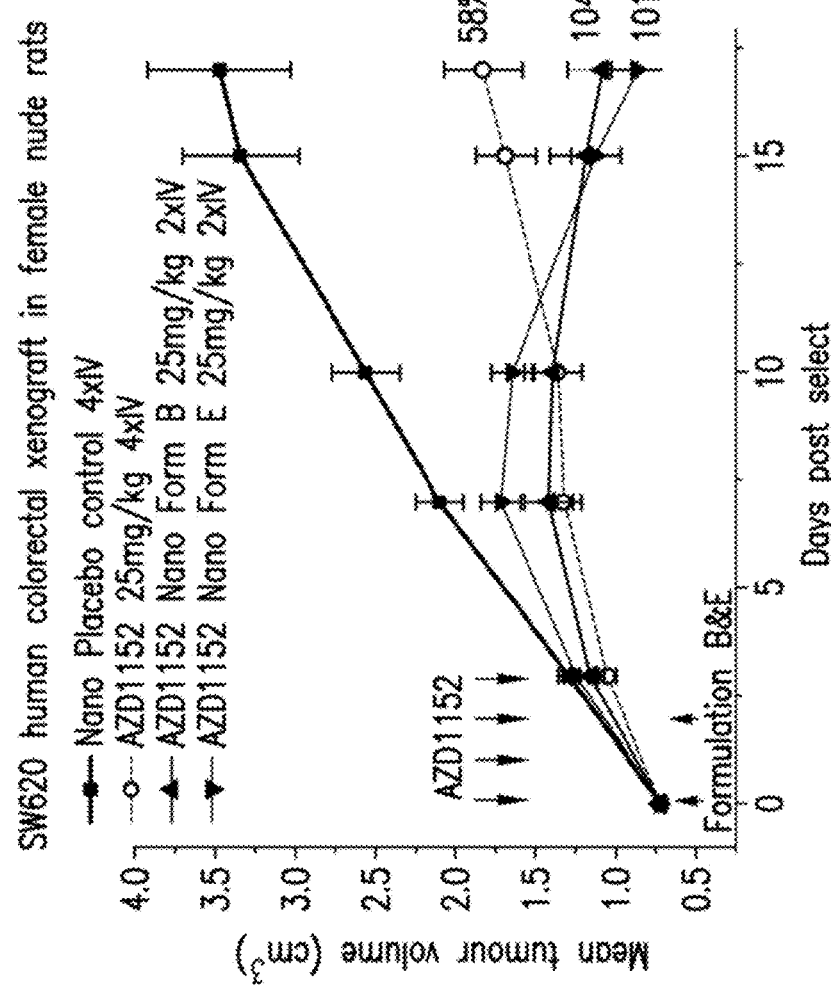

Effects of AZD1152 and AZD1152 nanoparticle formulations B and E in the tumour are characterized by the presence of enlarged polyploidy nuclei. FIGS. 6A, 6B and 6C show representative images of the tumour following treatment with each therapy from samples obtained at day 5. Effects of AZD1152 and AZD1152 hqpa nanoparticle formulations B and E on the bone marrow are characterized by the loss of cells from the bone marrow. FIGS. 6A, 6B and 6C show representative images of the tumour following treatment with each therapy from samples obtained at day 5.

FIGS. 6A, 6B and 6C show that Formulation E, delivered at half the dose intensity of AZD1152, has greater efficacy (FIG. 6A), induces a similar spectrum of tumour pathology changes (FIG. 6B) yet spares bone marrow (FIG. 6C).

Mouse Anti-Tumour Study (SW620 in Male Nude Mouse)

Male nude mice were bred at AstraZeneca. Animals were inoculated in the flank with SW620 human tumour cells, and then randomized onto study when tumours reached approximately 0.25 cm³. AZD1152 was dosed in tris buffer vehicle at the concentration indicated. AZD1152 hqpa nanoparticle formulation E was dosed in physiological saline. Previous pre-clinical work and methodologies with AZD1152 are published in Wilkinson et al, Clinical Cancer Research 2007 (13) 3682.

Data generated in the SW620 human tumour xenograft model in rat and mouse suggested that delivery of AZD1152 IV at 25 mg/kg for 4 days give maximal efficacy (100 mg/kg total dose).

In the SW620 model in mouse, the nanoparticles from Example 3 demonstrated equivalent efficacy to AZD1152 IV at 100 mg/kg and this efficacy was achieved at lower doses of only 25 mg/kg as a single dose, or even 5 mg/kg at day 1 and 3 (10 mg/kg equivalent) showing that efficacy may be delivered using a variety of different schedules and much lower doses using the nanoparticulate formulation of AZD1152 hqpa than an IV formulation of AZD1152.

Hence the claimed AZD1152 hqpa nanoparticulate formulation showed equivalent or improved tumour efficacy when delivered at a lower dose intensity. This may result in fewer side effects, for example less bone marrow toxicity.

Maximum activity was achieved with a 50 mg/kg dose equivalent of AZD1152 hqpa nanoparticulate formulation versus 100 mg/kg IV AZD1152. By using the formulations of the present invention, it may be possible to provide more active ingredient to the patient for the same adverse effects as previous maximum tolerated dose of AZD1152 dosed IV. Thus the risk/benefit profile of the formulations of the present invention might be improved.

Figure 7:
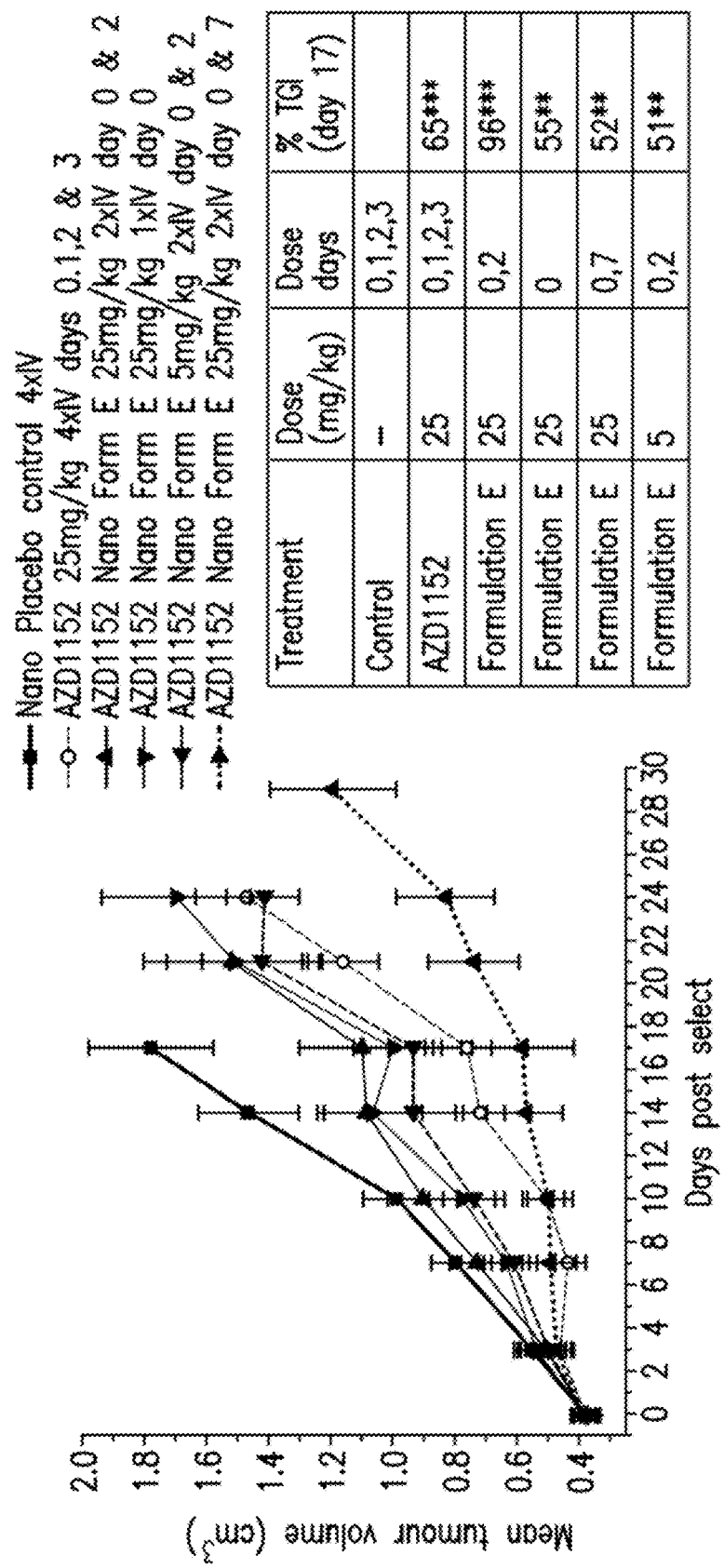
FIG. 7 depicts results from a dosing schedule study with one AZD1152 hqpa nanoparticulate formulation.

FIG. 7 shows data from efficacy/dose scheduling studies with Formulation E in SW620 xenograft in nude mouse. In this study AZD1152 was dosed on day 0-3 at 25 mg/kg (total 100 mg/kg). Formulation E was dosed at a variety of different schedules as described above.

Example 6

Figure 8:
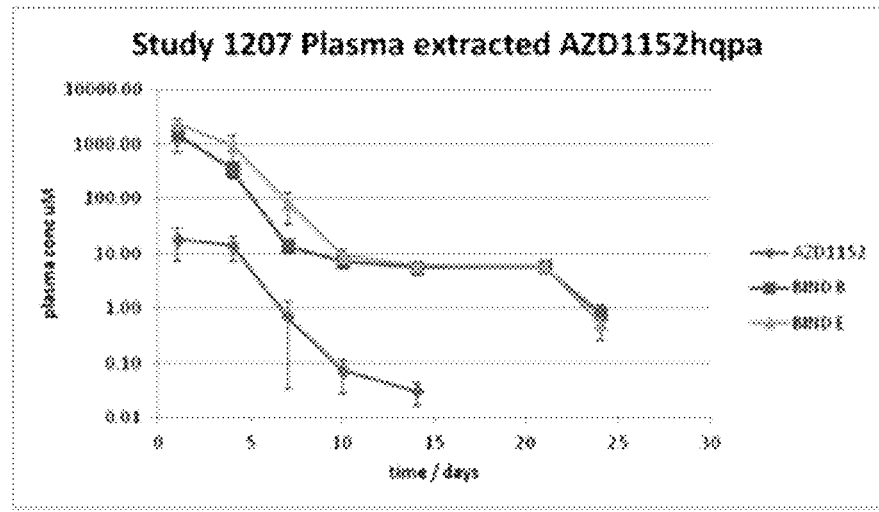
FIG. 8 depicts a comparison of plasma concentration of AZD1152 hqpa nanoparticles against AZD1152 IV in an in-vivo exposure study.
Figure 8:
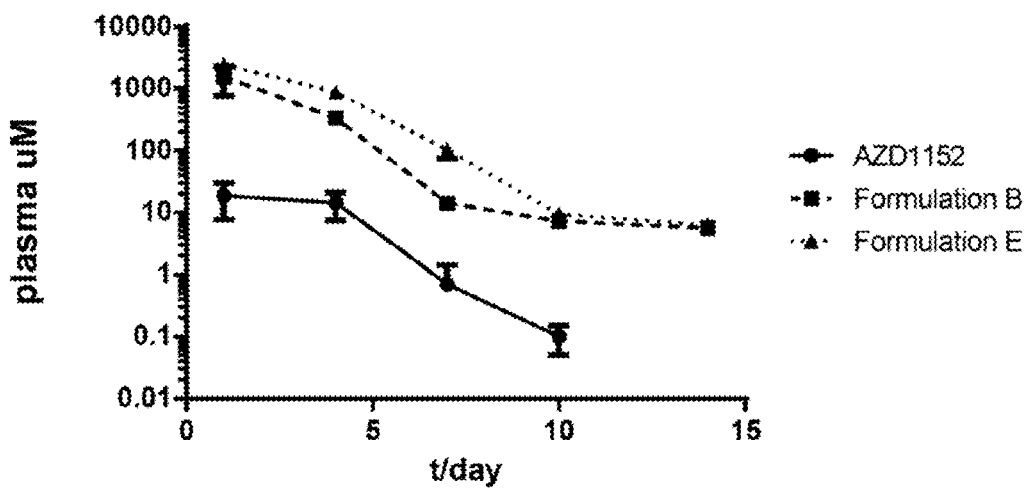

In-vivo exposure was examined comparing AZD1152 IV (dosed 4×25 mg/kg) days 1-4 IV) with Formulations B (dosed 2×25 mg/kg on days 1& 3 IV) and E (dosed 2×25 mg/kg days 1 and 3 IV) from the study in nude rats described in Example 5. The results are shown (averaged value from several data points) in FIG. 8. The concentrations measured following the AZD1152 IV dose are for the drug AZD1152 hqpa.

The data show the total AZD1152 hqpa extracted from the sample (within the nanoparticles and released from them) at the sampling point and thus show how long either drug or encapsulated drug is still present in the body over this time course, ie the longevity of exposure to the AZD1152 hqpa after dosing. The data show that a lower dose intensity gave higher total drug concentration in blood, sustained for a longer period if delivered as a nanoparticulate formulation rather than as intravenous active drug.

Summary of Bioanalytical Method to Measure Total Drug from In-Vivo Samples Dosed with Nanoparticles.

This is a multi step process which must be carried out on ice wherever possible to halt further release of drug from the nanoparticles.

Total Drug Extraction method:

Dissolve solid parent drug in DMSO to 2 mM concentration.

Aliquot 50 µl of each plasma samples, using appropriate dilution factor, into 96 well plate.

Prepare at standard calibration curve using the Hamilton Star Robot from the 2 mM stock in DMSO (see appendix 1 for preparation details)

Add 150 µl of acetonitrile with internal standard.

Shake the plate to mix the samples.

Spin in centrifuge at 4500 rpm for 10 minutes.

Transfer 50 µl of supernatant to clean 96 well plate.

Add 300 µl of water.

Analyse via LC-MS/MS (liquid chromatography–mass spectrometry/tandem mass spectrometry).

Appendix 1—Standard Curve Preparation Details

The robot will first add suitable diluent into the microplate for the dilutions before serially diluting the stocks from right to left in the microplate, one row per compound (see table A below):

TABLE A showing the 11 dilutions from right to left (columns 12-1) of the dilution plate for a 2 mM starting stock in column 12 of the dilution microplate. 2.5 µl from columns 1-11 are then spiked left to right into wells 2-12 of a matrix plate to result in an eleven point curve (Table B).

| Column of predilution plate | Final conc µM | Volume of conc to be diluted µL | Volume of DMSO diluent µL | dilution factor |
|---|---|---|---|---|
| 12 | 2000 | — | — | — |
| 11 | 200 | 25 µL from Col. 12 | 225 | 10 |
| 10 | 100 | 125 µL from Col. 11 | 125 | 2 |
| 9 | 40 | 100 µL from Col. 10 | 150 | 2.5 |

TABLE A-continued showing the 11 dilutions from right to left (columns 12-1) of the dilution plate for a 2 mM starting stock in column 12 of the dilution microplate. 2.5 µl from columns 1-11 are then spiked left to right into wells 2-12 of a matrix plate to result in an eleven point curve (Table B).

| Column of predilution plate | Final conc µM | Volume of conc to be diluted µL | Volume of DMSO diluent µL | dilution factor |
|---|---|---|---|---|
| 8 | 20 | 125 µL from Col. 9 | 125 | 2 |
| 7 | 10 | 125 µL from Col. 8 | 125 | 2 |
| 6 | 2 | 50 µL from Col. 7 | 200 | 5 |
| 5 | 1 | 125 µL from Col. 6 | 125 | 2 |
| 4 | 0.4 | 100 µL from Col. 5 | 150 | 2.5 |
| 3 | 0.2 | 125 µL from Col. 4 | 125 | 2 |
| 2 | 0.1 | 125 µL from Col. 3 | 125 | 2 |
| 1 | 0.02 | 50 µL from Col. 2 | 200 | 5 |

TABLE B

Table demonstrating the calibration curve generated following the spiking of the robot-generated dilution series.

| Final Concentration (nM) | Volume of matrix (µL) | Volume spiked (µL) | DMSO Working Solution (µM) | Column of Plasma Prep plate |
|---|---|---|---|---|
| 0 | 47.5 | 2.5 µL DMSO | | 1 |
| 1 | 47.5 | 2.5 | 0.02 | 2 |
| 5 | 47.5 | 2.5 | 0.1 | 3 |
| 10 | 47.5 | 2.5 | 0.2 | 4 |
| 20 | 47.5 | 2.5 | 0.4 | 5 |
| 50 | 47.5 | 2.5 | 1 | 6 |
| 100 | 47.5 | 2.5 | 2 | 7 |
| 500 | 47.5 | 2.5 | 10 | 8 |
| 1000 | 47.5 | 2.5 | 20 | 9 |
| 2000 | 47.5 | 2.5 | 40 | 10 |
| 5000 | 47.5 | 2.5 | 100 | 11 |
| 10000 | 47.5 | 2.5 | 200 | 12 |

Columns 1-11 from Table A are spiked into columns 2-12 of the matrix plate to produce the eleven-point calibration curve as above

LC-MS/MS Parameters

| | |
|---|---|
| Mass Spec | Waters Xevo TQS (serial No.-186005453) |
| Column | Phenomenex Kinetex C18 50 × 2.1, 2.6 u |
| Solvent A | 95% Water + 0.1% Formic acid |
| Solvent B | 95% MeOH + 0.1% Formic acid |

| Gradient | Time (min) | % A | % B |
|---|---|---|---|
| | 0 | 95 | 5 |
| | 0.3 | 95 | 5 |
| | 1.9 | 5 | 95 |
| | 2.3 | 5 | 95 |
| | 2.31 | 95 | 5 |
| | 2.5 | 95 | 5 |

| | |
|---|---|
| Flow | 0.75 ml/min |
| Run time | 2.5 min, use a divert valve for initial 0.3 minutes |

Optimisation Parameters

| Compound | Ionisation mode | Polarity | Parent ion | Daughter ion | Cone voltage (v) | Collison Energy | Retention Time (min) |
|---|---|---|---|---|---|---|---|
| AZD1152 | ESI | Positive | 588.941 | 491.13 | 20 | 16 | 1.07 |
| AZD1152 hqpa | ESI | Positive | 509.042 | 129.74 | 40 | 16 | 0.98 |
| Compound A | ESI | Positive | 405.588 | 173.81 | 80 | 22 | 1.35 |

Compound A: 2-ethyl-4-{[2'-(1H-tetrazol-5-yl)biphenyl-4-yl]methoxy}quinoline (internal standard). See for example WO92/02508 and WO92/13853.

Example 7 (Using a Nominal 1 g Batch)

Pamoic Acid Nanoparticle Procedure
Nanoparticles of AZD1152 hqpa with pamoic acid were prepared according to the process set out below.
Composition (of Formulation Described Herein after as Formulation G1):

| Component | Weight Percent of the Nanoparticle | Molar Percent of the Nanoparticle |
|---|---|---|
| 16/5 PLA-PEG | 73.1% | 5.8% |
| PLA | 54.8% | 4.4% |
| PEG | 18.3% | 1.5% |
| AZD1152 hqpa | 17.0% | 53.5% |
| Pamoic acid | 9.9% | 40.7% |

7.1 Preparation of pamoic acid solution. A 29% (w/w) solution of pamoic acid in DMSO was prepared by mixing 2.9 g of pamoic acid with 7.1 g of DMSO in a container. The container was heated in a heating oven at 70-80° C. until all of the pamoic acid was dissolved.

7.2 Preparation of 8% TFA/7.5% water/84.5% benzyl alcohol (wt %) solution. Trifluoroacetic acid (TFA) (3.2 g), deionized (DI) water (3.0 g), and benzyl alcohol (BA) (33.8 g) were combined to prepare the 8% TFA/7.5% water/84.5% benzyl alcohol (wt %) solution.

7.3 Buffer preparation:
To make 1000 ml of 0.17 M Phosphate (pKa2=7.2) Buffer: pH=6.5, Formulate two stock buffers: A. dissolve 13.26 g of Sodium phosphate monobasic, anhydrous $NaH_2PO_4H_2O$ (Mr=119.98) in 650 ml of pure water and B. dissolve 10.82 g of Sodium phosphate dibasic, anhydrous $NaH_2PO_4$ (Mr=141.96) in 650 ml of pure water. Add buffer B to buffer A while mixing until the pH=6.50 at the lab temperature of 25° C.

Alternative:
To make 1000 ml of 0.17 M sodium phosphate buffer at pH 6.5: Into ~800 ml of DI water, dissolve 16.26 g of sodium phosphate monobasic, dihydrate ($NaH_2PO_4$-$2H_2O$; FW=156.01) and 11.70 g of sodium phosphate dibasic, dihydrate ($Na_2HPO_4$-$2H_2O$; FW=177.99) and add sufficient extra water to make 1000 ml, at the lab temperature of 25° C.

7.4 Preparation of polymer solution
  To 20 mL glass vial add polymer-PEG, 700 mg
  Add 7078 mg of ethyl acetate to glass vial and vortex overnight to give a polymer-EA solution.

7.5 Preparation of Aqueous Solution:
  0.12% polyoxyethylene (100) stearyl ether sold under the trademark Brij®100, 4% Benzyl Alcohol in Water
  To 1 L bottle add 1.2 g polyoxyethylene (100) stearyl ether sold under the trademark Brij® 100 and 958.8 g of DI water and mix on stir plate until dissolved.

Add 40 g of benzyl alcohol to polyoxyethylene (100) stearyl ether sold under the trademark Brij®/water and mix on stir plate until dissolved.

7.6 Preparation of drug solution

Weigh 300 mg of AZD1152 hqpa in 20 ml scintillation vial

Add 2399 mg of above 8% TFA/7.5% water/BA solution to AZD1152

Add 634 mg of above 29% pamoic/DMSO solution to the drug solution and vortex to get clear drug solution Right before formulation, combine drug and polymer solution.

7.7 Formation of emulsion. Ratio of Aqueous phase to Organic phase is 5:1

Pour organic phase into aqueous solution and homogenize using hand-held rotor/stator homogenizer for 10 seconds at room temperature to form coarse emulsion. Store in ice for 10-15 minutes.

Feed solution through high pressure homogenizer (110S) with pressure set at ~9000 psi on compressed air inlet gauge for 1 discreet passes to form nanoemulsion Formation of Nanoparticles Pour emulsion into Quench (0.17M Sodium phosphate, pH 6.5) at <5 C while stirring on stir plate. Ensure at least 5 minutes has passed since the beginning of collection, before quenching. Ratio of Quench to Emulsion is 10:1

Add 35% (w/w) polysorbate 80 sold under the trademark Tween® 80 in water to quench at ratio of 100:1 polysorbate 80 sold under the trademark Tween® 80 to drug by weight.

Concentrate nanoparticles through tangential flow filtration (TFF)

Concentrate quench on TFF with 300 kDa Pall cassette (3×0.1 $m^2$ membranes) to ~200 mL.

Diafilter ~20 diavolumes (4 liter) using cold DI water.

Bring volume down to minimal volume

Add 100 mL of cold water to vessel and pump through membrane to rinse.

Collect material in glass vial, ~100 mL 7.8 Determination of solids concentration of unfiltered final slurry:

To tared 20 mL scintillation vial add a volume of final slurry and dry under vacuum on lyo/oven.

Determine weight of nanoparticles in the volume of slurry dried down 7.9 Determination of solids concentration of 0.45 μm filtered final slurry:

Filter a portion of the final slurry sample before addition of sucrose through 0.45 μm syringe filter To tared 20 mL scintillation vial add a volume of filtered sample and dry under vacuum on lyo/oven.

7.10 Add 1 part of sucrose to final 9 parts of slurry sample to attain 10% sucrose.

7.11 Freeze remaining sample of unfiltered final slurry with sucrose

Figure 9:
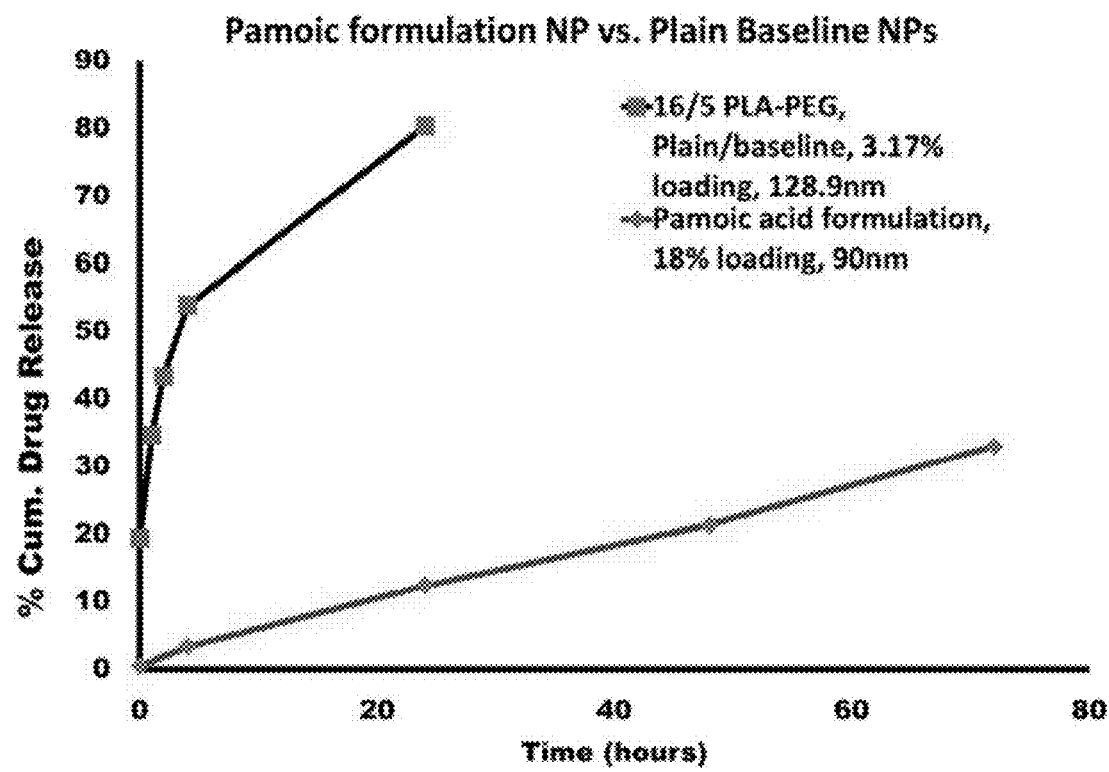
FIG. 9 depicts in vitro release profiles for a pamoic acid nanoparticle formulation versus a control therapeutic nanoparticle formulation.

FIG. 9 shows representative AZD1152 hqpa in vitro release demonstrating controlled and slow/sustained release of drugs from pamoic acid nanoparticles compared to that from baseline nanoparticles without pamoic acid counter-ions (made as described for control formulations in Example 2). Another pamoic acid formulation, referred to hereinafter as formulation G2 was prepared as follows: (Using a nominal 1 g batch)

Composition:

| Component | Weight Percent of the Nanoparticle | Molar Percent of the Nanoparticle |
|---|---|---|
| 16/5 PLA-PEG | 67.7% | 4.5% |
| PLA | 50.7% | 3.4% |
| PEG | 16.9% | 1.1% |
| AZD1152 hqpa | 19.4% | 51.1% |
| Pamoic acid | 12.9% | 44.4% |

Example 7a 7a.1 Preparation of pamoic acid solution. A 29% (w/w) solution of pamoic acid in DMSO was prepared by mixing 2.9 g of pamoic acid with 7.1 g of DMSO in a container. The container was heated in a heating oven at 70-80° C. until all of the pamoic acid was dissolved.

7a.2 Preparation of 8% TFA/7.5% water/84.5% benzyl alcohol (wt %) solution. Trifluoroacetic acid (TFA) (3.2 g), deionized (DI) water (3.0 g), and benzyl alcohol (BA) (33.8 g) were combined to prepare the 8% TFA/7.5% water/84.5% benzyl alcohol (wt %) solution.

7a.3 Buffer preparation:

To make 1000 ml of 0.17 M Phosphate ($pK_a2$=7.2) Buffer: pH=6.5, Formulate two stock buffers: A. dissolve 13.26 g of Sodium phosphate monobasic, anhydrous $NaH_2PO_4H_2O$ (Mr=119.98) in 650 ml of pure water and B. dissolve 10.82 g of Sodium phosphate dibasic, anhydrous $NaH_2PO_4$ (Mr=141.96) in 650 ml of pure water. Add buffer B to buffer A while mixing until the pH=6.50 at the lab temperature of 25° C.

Alternative:

To make 1000 ml of 0.17 M sodium phosphate buffer at pH 6.5: Into ~800 ml of DI water, dissolve 16.26 g of sodium phosphate monobasic, dihydrate ($NaH_2PO_4$-$2H_2O$; FW=156.01) and 11.70 g of sodium phosphate dibasic, dihydrate ($Na_2HPO_4$-$2H_2O$; FW=177.99) and add sufficient extra water to make 1000 ml, at the lab temperature of 25° C.

7a.4 Preparation of polymer solution

To 20 mL glass vial add polymer-PEG, 700 mg

Add 6572 mg of ethyl acetate to glass vial and vortex overnight to give a polymer-EA solution.

7a.5 Preparation of Aqueous Solution:

0.15% polyoxyethylene (100) stearyl ether sold under the trademark Brij®100, 4% Benzyl Alcohol in Water To 1 L bottle add 1.5 g polyoxyethylene (100) stearyl ether sold under the trademark Brij®100 and 958.5 g of DI water and mix on stir plate until dissolved.

Add 40 g of benzyl alcohol to polyoxyethylene (100) stearyl ether sold under the trademark Brij®/water and mix on stir plate until dissolved.

7a.6 Preparation of drug solution

Weigh 300 mg of AZD1152 hqpa in 20 ml scintillation vial

Add 2746 mg of above 8% TFA/7.5% water/BA solution to AZD1152

Add 792 mg of above 29% pamoic/DMSO solution to the drug solution and vortex to get clear drug solution Right before formulation, combine drug and polymer solution.

7a.7 Formation of emulsion. Ratio of Aqueous phase to organic phase is 5:1

Pour organic phase into aqueous solution and homogenize using hand-held rotor/stator homogenizer for 10 seconds at room temperature to form coarse emulsion. Store in ice for 10 minutes.

Feed solution through high pressure homogenizer (110S) with pressure set at ~9000 psi on compressed air inlet gauge for 1 discreet passes to form nanoemulsion Formation of nanoparticles Immediately pour emulsion into Quench (0.17M Sodium phosphate, pH 6.5) at <5° C. while stirring on stir plate. Ratio of Quench to Emulsion is 10:1

Add 35% (w/w) polysorbate 80 sold under the trademark Tween® 80 in water to quench at ratio of 100:1 polysorbate 80 sold under the trademark Tween® 80 to drug by weight.

Concentrate nanoparticles through tangential flow filtration (TFF)

Concentrate quench on TFF with 300 kDa Pall cassette ($3\times0.1$ $m^2$ membranes) to ~200 mL.

Diafilter ~20 diavolumes (4 liter) using cold DI water.

Bring volume down to minimal volume

Add 100 mL of cold water to vessel and pump through membrane to rinse.

Collect material in glass vial, ~100 mL 7a.8 Determination of solids concentration of unfiltered final slurry:

To tared 20 mL scintillation vial add a volume of final slurry and dry under vacuum on lyo/oven.

Determine weight of nanoparticles in the volume of slurry dried down 7a.9 Determination of solids concentration of 0.45 μm filtered final slurry:

Filter a portion of the final slurry sample before addition of sucrose through 0.45 μm syringe filter To tared 20 mL scintillation vial add a volume of filtered sample and dry under vacuum on lyo/oven.

7a.10 Add 1 part of sucrose to final 9 parts of slurry sample to attain 10% sucrose by weight.

7a.11 Freeze remaining sample of unfiltered final slurry with sucrose

Example 7b

A further process to make a formulation G1 (nominal 1 g batch) is described below:

7b.1 Preparation of pamoic acid solution. A 29% (w/w) solution of pamoic acid in DMSO was prepared by mixing 2.9 g of pamoic acid with 7.1 g of DMSO in a container. The container was heated in a heating oven at 70-80° C. until all of the pamoic acid was dissolved.

7b.2 Preparation of 8% TFA/7.5% water/84.5% benzyl alcohol (wt %) solution. Trifluoroacetic acid (TFA) (3.2 g), deionized (DI) water (3.0 g), and benzyl alcohol (BA) (33.8 g) were combined to prepare the 8% TFA/7.5% water/84.5% benzyl alcohol (wt %) solution.

7b.3 Buffer preparation:

To make 1000 ml of 0.17 M Phosphate (pKa2=7.2) Buffer: pH=6.5, Formulate two stock buffers: A. dissolve 13.26 g of Sodium phosphate monobasic, anhydrous $NaH_2PO_4H_2O$ (Mr=119.98) in 650 ml of pure water and B. dissolve 10.82 g of Sodium phosphate dibasic, anhydrous $NaH_2PO_4$ (Mr=141.96) in 650 ml of pure water. Add buffer B to buffer A while mixing until the pH=6.50 at the lab temperature of 25° C.

Alternative:

To make 1000 ml of 0.17 M sodium phosphate buffer at pH 6.5: Into ~800 ml of DI water, dissolve 16.26 g of sodium phosphate monobasic, dihydrate ($NaH_2PO_{4-2}H_2O$; FW=156.01) and 11.70 g of sodium phosphate dibasic, dihydrate ($Na_2HPO_{4-2}H_2O$; FW=177.99) and add sufficient extra water to make 1000 ml, at the lab temperature of 25° C.

7b.4 Preparation of polymer solution

To 20 mL glass vial add polymer-PEG, 591.3 mg

Add 5978.6 mg of ethyl acetate to glass vial and vortex overnight to give a polymer-EA solution.

7b.5 Preparation of Aqueous Solution:

0.12% polyoxyethylene (100) stearyl ether sold under the trademark Brij®100, 4% Benzyl Alcohol, 5.7% DMSO in Water To 1 L bottle add 1.4 g polyoxyethylene (100) stearyl ether sold under the trademark Brij® 100, and 901.6 g of DI water and mix on stir plate until dissolved.

Add 40 g of benzyl alcohol and 57 g of DMSO to polyoxyethylene (100) stearyl ether sold under the trademark Brij®/water and mix on stir plate until dissolved.

7b.6 Preparation of drug solution

Weigh 253.4 mg of AZD1152 hqpa in 20 ml scintillation vial

Add 2026.8 mg of above 8% TFA/7.5% water/BA solution to AZD1152

Add 535.5 mg of above 29% pamoic/DMSO solution to the drug solution and vortex to get clear drug solution Right before formulation, combine drug and polymer solution.

7b.7 Formation of emulsion. Ratio of Aqueous phase to organic phase is 5.5:1

Pour organic phase into aqueous solution and homogenize using hand-held rotor/stator homogenizer for 10 seconds at room temperature to form coarse emulsion. Store in ice for 10-15 minutes.

Feed solution through high pressure homogenizer (110S) with pressure set at ~9,000 psi on compressed air inlet gauge for 1 discreet passes to form nanoemulsion Formation of Nanoparticles Pour emulsion into Quench (0.17M Sodium phosphate, pH 6.5) at <5° C. while stirring on stir plate. Ensure at least 5 minutes has passed since the beginning of collection, before quenching. Ratio of Quench to Emulsion is 3:1 by weight.

Add 35% (w/w) polysorbate 80 sold under the trademark Tween® 80 in water to quench at ratio of 20:1 polysorbate 80 sold under the trademark Tween® 80 to drug by weight.

Concentrate nanoparticles through tangential flow filtration (TFF)

Concentrate quench on TFF with 300 kDa Pall cassette ($3\times0.1$ $m^2$ membranes) to ~200 mL.

Diafilter ~20 diavolumes (4 liter) using ambient temperature DI water.

Bring volume down to minimal volume

Add 100 mL of DI water to vessel and pump through membrane to rinse.

Collect material in glass vial, ~100 mL 7b.8 Determination of solids concentration of unfiltered final slurry:

To tared 20 mL scintillation vial add a volume of final slurry and dry under vacuum on lyo/oven.

Determine weight of nanoparticles in the volume of slurry dried down.

7b.9 Determination of solids concentration of 0.45 μm filtered final slurry:

Filter a portion of the final slurry sample before addition of sucrose through 0.45 μm syringe filter To tared 20 mL scintillation vial add a volume of filtered sample and dry under vacuum on lyo/oven.
7b.10 Add 1 part of sucrose to final 9 parts of unfiltered slurry sample to attain 10% sucrose by weight.
7b.11 Freeze remaining sample of unfiltered final slurry with sucrose Example 8: Comparison of Formulations E, F1 and F2

Figure 10:
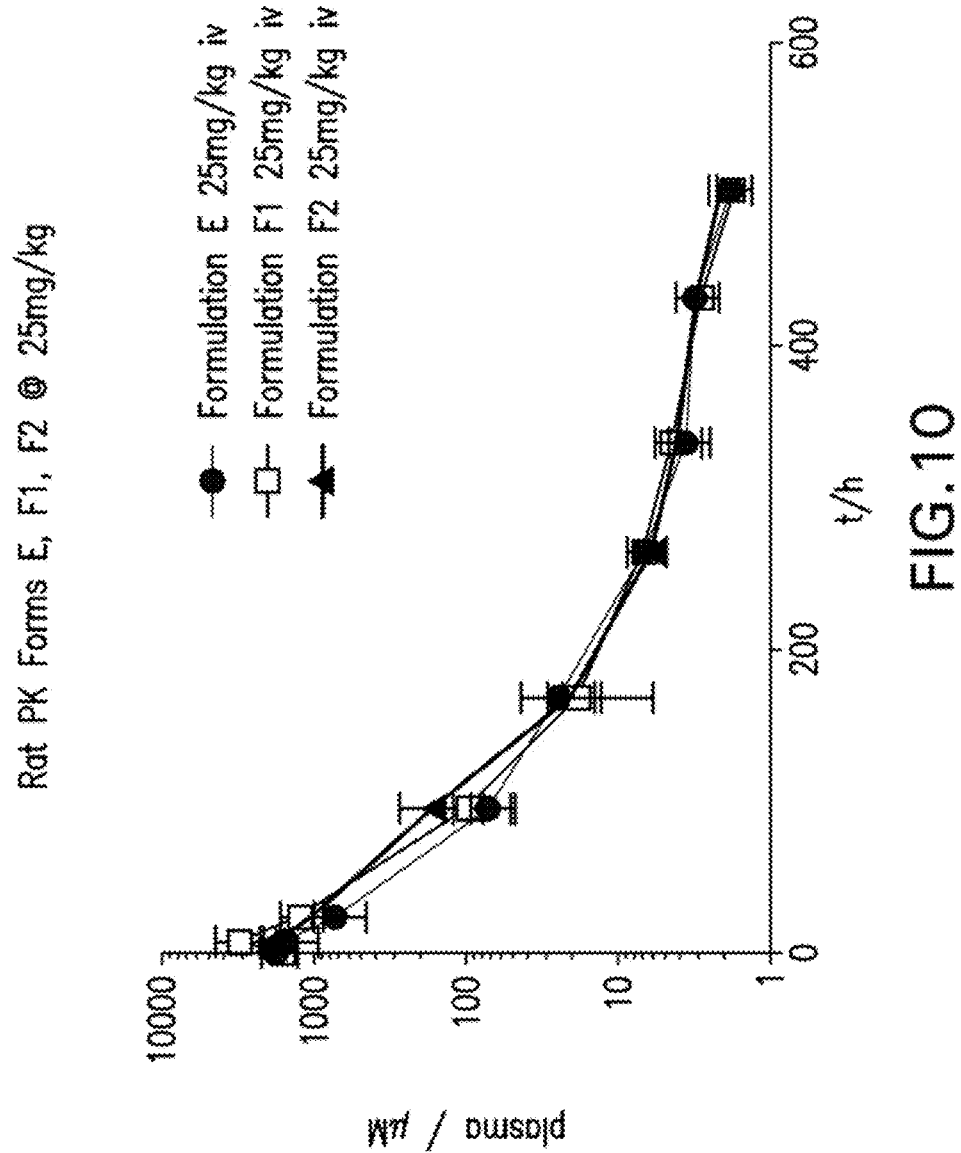
FIG. 10 depicts comparative pharmacokinetic profiles for three nanoparticulate formulations.
Figure 11:
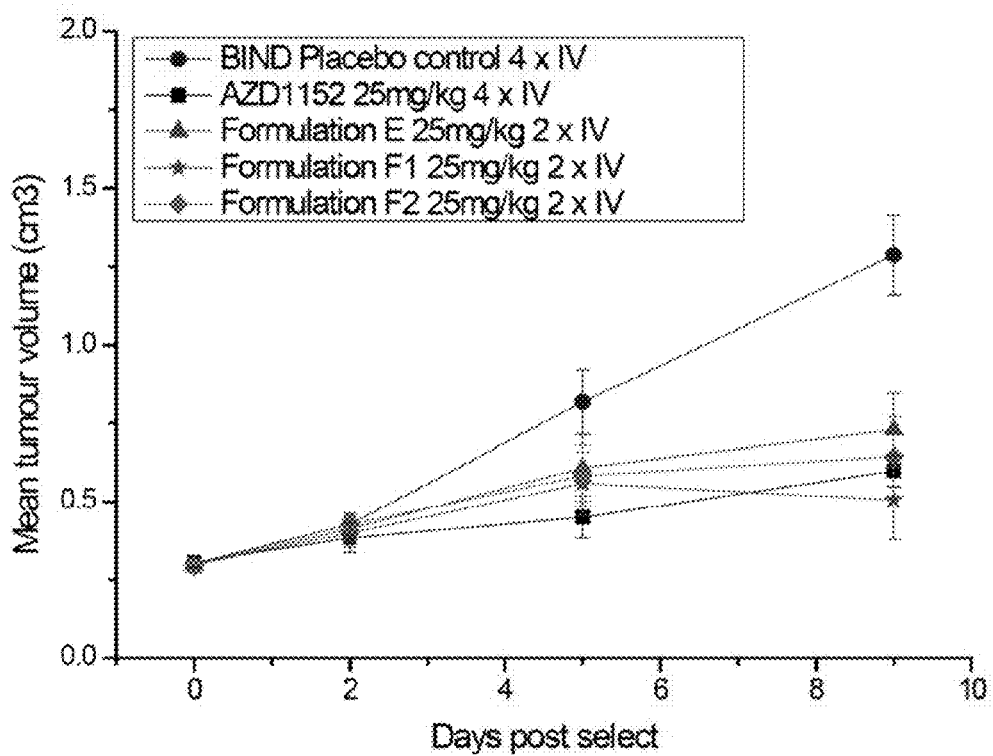
FIG. 11 depicts a comparison of results from an SW620 study.

Formulation E was described in Example 3. Formulations F1 and F2 were described in Example 2.
In-Vivo Exposure
FIG. 10 shows a comparison of in-vivo exposure in rat for formulations E, F1 and F2. The experiments were carried out as single doses of 25 mg/kg in rats and analysed by an analogous method to that described in Example 6.
In-Vivo Efficacy Data
The data shown in FIG. 11 show that Formulations E, F1 and F2 give equivalent efficacy following short term dosing in of nude rats with established SW620 tumour xenografts. The experiments were carried out according to the methods as described in Example 5. Rats bearing SW620 tumours were dosed with AZD1152 at 25 mg/kg daily for 4 days, or Formulation E, F1 and F2 at 25 mg/kg on days 0 and 2. Formulation E, F1 and F2 gave equivalent efficacy. Efficacy was equivalent to AZD1152 and comparable to that seen in previous studies with AZD1152 and Formulation E at this time point. The study was terminated at day 9 to enable analysis of tumour pharmacodymanic markers and bone marrow. These data demonstrate that formulations E, F1 and F2 give equivalent efficacy.
Comparison of Nanoparticle Formulations E, F1 and F2 on Tumour Phospho-Histone H3 Biomarkers
This experiment compares the effect of Formulation E, F1 and F2 on a phospho-histone H3 phosphorylation (pHH3) in SW620 tumours. AZD1152 was included as a positive control. The activity was measured as an inhibition of histone H3 phosphorylation on $Ser^{10}$ (pHH3 as a sensitive, highly dynamic surrogate marker of Aurora B kinase activity). Average level of pHH3 positivity [%] was calculated for the cells in G2/M phase of the cell cycle for each treatment group at 24 hrs and 96 hrs post $1^{st}$ dose and compared to the pHH3 level observed for the cells in G2/M cell cycle phase that were extracted from the tumours treated with BIND Placebo (referred here as 100%). Statistical significance was calculated using Student t-test assuming unequal variances (*p<0.05,  p<0.01, * p<001, n.s. P>0.05).
Formulations (Formulation E, F1 and F2) were dosed as described above to SW620 colon xenografts established in nude female rats. Rats were injected IV with BIND Placebo (0 mg/kg), or AZD1152 or AZD1152 hqpa Formulation E/F1/F2 at 25 mg/kg on day 1, and terminated on day 2 (24 hrs post $1^{st}$ dose) or on day 5 (96 hrs post $1^{st}$ dose). Frozen tumours were disaggregated using Medimachine (BD Biosystems), fixed with 80% ethanol for a minimum of 12 hrs and prepared for DNA content (PI staining) and pHH3 analysis by flow cytometry using BD FACSCanto analyser (pHH3 primary antibody: Millipore 06-570; secondary antibody: FITC Anti rabbit IgG fluorescein conjugated secondary antibody Millipore AP307F) as previously described by Wilkinson, R W et al., Clin Cancer Res, 2007; 13(12).

Figure 12:
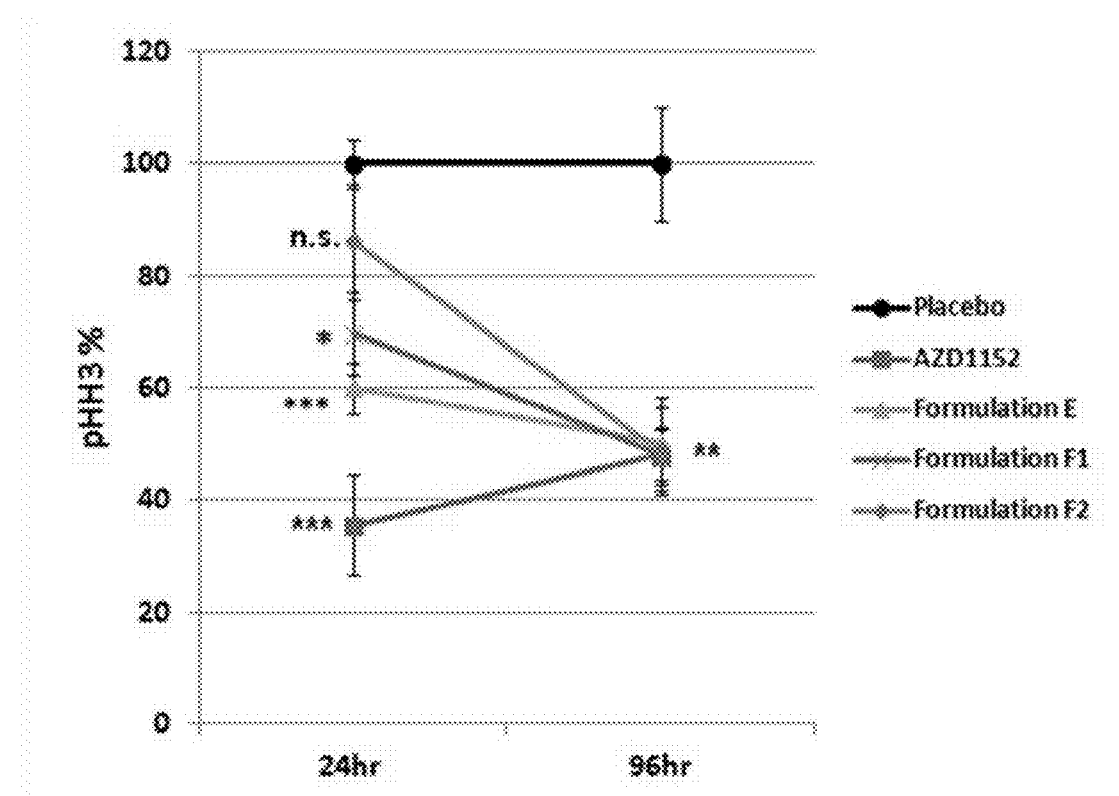
FIG. 12 depicts a further comparison of results from an SW620 study.

FIG. 12 shows that the proportion of pHH3-positive cells within the G2/M phase of the cell cycle was maximally suppressed by AZD1152 at 24 hours. Tumours exposed to Formulations E or F1, F2 showed less reduction in pHH3 at 24 hrs post single dose compared with animals receiving AZD1152. At 96 hours levels of pHH3 reduction were comparable across all groups.

Figure 13:
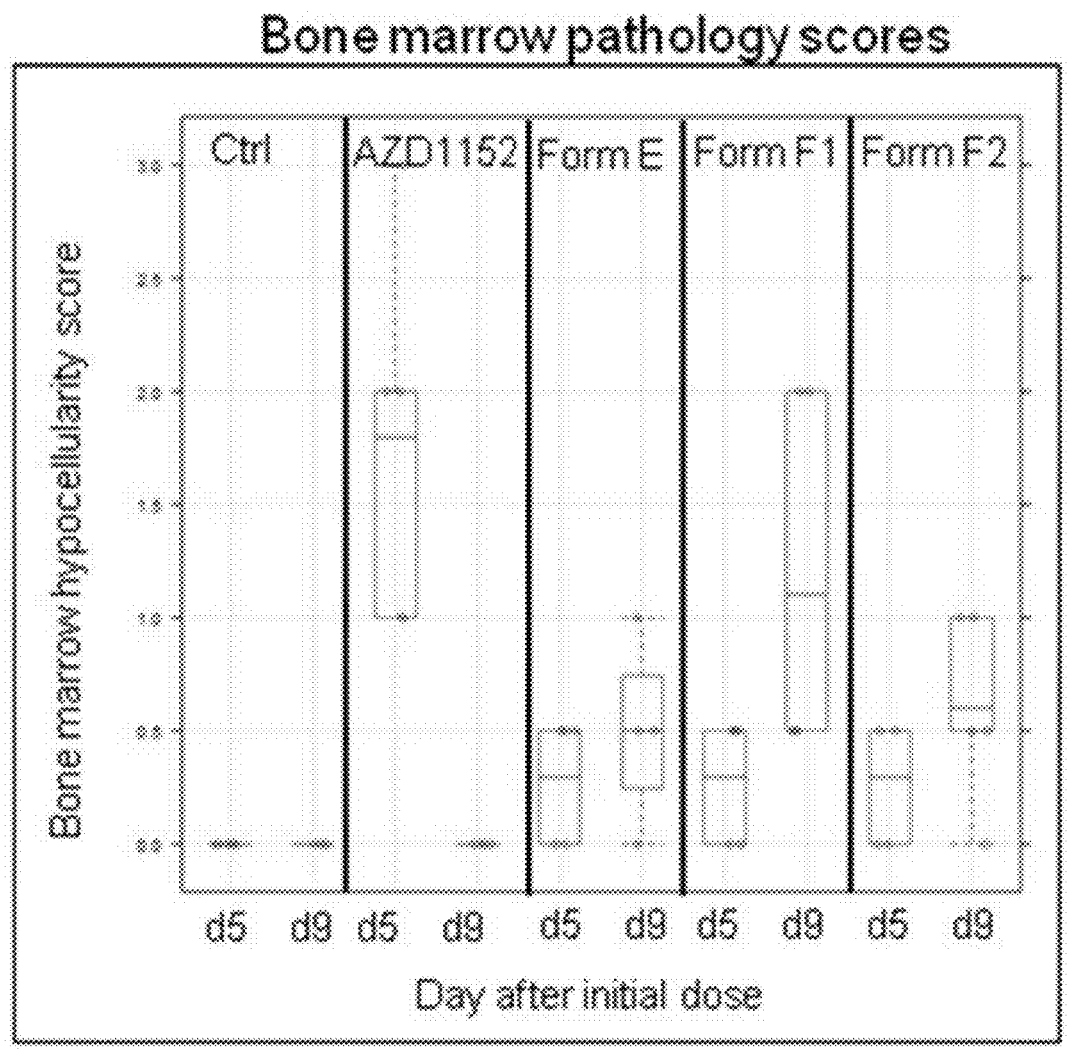
FIG. 13 depicts bone marrow effects of certain nanoparticulate formulations.

These data show that Formulations E, F1 and F2 give equivalent suppression of pHH3 and hence Aurora kinase B activity over a single dose time course.
Effects of Formulations E, F1 and F2 on Bone Marrow.
This example shows the effects of the Formulations on the bone marrow assessed by two independent measures.
Rats were injected IV with BIND Placebo (0 mg/kg), or AZD1152/AZD1152 hqpa Formulation E/F1/F2 at 25 mg/kg at the times indicated and sacrificed at the times indicated.
Bone marrows samples were extracted from each animal. Firstly samples of bone marrow were processed for pathological assessment. Femuro-tibial joints were taken to 10% Buffered Formalin, decalcified using standard procedures, paraffin embedded and stained with haemotoxylin and eosin. Pathological assessment of bone marrow hypo-cellularity was carried out by a pathologist (FIG. 13). Bone marrow integrity was scored by the pathologist. A bone marrow hypocellularity score was generated based on a scoring system of 0-4, with 0 representing no bone marrow effect and 4 representing maximal effect on the bone marrow. The figures show the Median, the 95% confidence intervals and the range for each group of animals at day 5 and 9. The data show that while AZD1152 has a large impact on bone marrow, each of the tested nanoparticulate formulations of AZD1152 hqpa show equivalent minimal effects on bone marrow.

Figure 14:
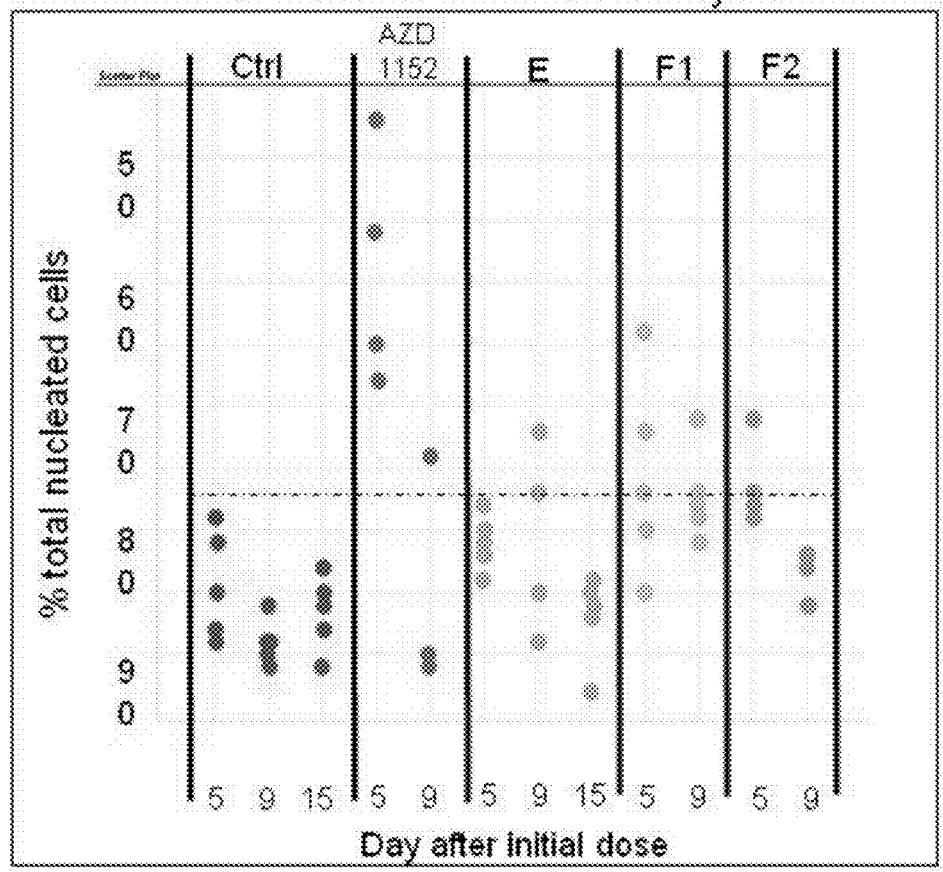
FIG. 14 depicts bone marrow effects of certain nanoparticulate formulations.

Secondly bone marrow flushes taken to examine bone marrow cellularity by FACs. At termination bone marrow from each Femur was taken into 50% FBS and 50% PBS on ice. Cells were pelleted by centrifugation at 4° C. and re-suspended in PBS. Cells were pelleted again at 4° C. and re-suspended in PBS. 50 μl of LDS-751 (0.5 mg/ml in methanol) was added and cells vortexed. Finally the cells were filtered through a 50 micron filter into a FACS tube. Samples were analysed on a FACS Canto (Beckton Dickinson). The results are shown in FIG. 14. A bone marrow hypocellularity is represented as a total of nucleated cells relative to untreated controls. The percentage cellularity of each bone marrow sample in each individual animal are shown. The dotted line represents the lowest percentage total nucleated cell value seen in animals receiving only vehicle (empty nanoparticle). The results show that while AZD1152 has a large impact on bone marrow, each of the tested nanoparticulate formulations of AZD1152 hqpa show equivalent minimal effects on bone marrow.

Example 9: Data for Formulations G

Comparison of Nanoparticle Formulations G1 and G2 on Tumour Phospho-Histone H3 Biomarkers
This experiment compares the effect of Formulation G1 and G2 on a phospho-histone H3 phosphorylation (pHH3) in SW620 tumours. AZD1152 was included as a positive control.
The activity was measured as an inhibition of histone H3 phosphorylation on $Ser_{10}$ (pHH3 as a sensitive, highly dynamic surrogate marker of Aurora B kinase activity). Average level of pHH3 positivity [%] was calculated for the cells in G2/M phase of the cell cycle for each treatment group at 24, 48, 72, 96 and 120 hrs post 1 dose and compared to the pHH3 level observed for the cells in G2/M cell cycle phase that were extracted from the tumours treated with BIND Placebo (referred here as 100%).
Formulations (Formulation G1 and G2) were dosed as described above to SW620 colon xenografts established in nude female rats. Rats were injected IV with BIND Placebo (0 mg/kg), or AZD1152 or AZD1152 hqpa Formulation G1 or G2 at 25 mg/kg on day 1, and terminated on day 2 (24 hrs post $1^{st}$ dose), day 3 (48 hrs post $1^{st}$ dose), day 4 (72 hrs after $1^{st}$ dose), day 5 (96 hrs post $1^{st}$ dose) and day 6 (120 hrs post $1^{st}$ dose). Frozen tumours were disaggregated using Medimachine (BD Biosystems), fixed with 80% ethanol for a minimum of 12 hrs and prepared for DNA content (PI staining) and pHH3 analysis by flow cytometry using BD FACSCanto analyser (pHH3 primary antibody: Millipore 06-570; secondary antibody: FITC Anti rabbit IgG fluorescein conjugated secondary antibody Millipore AP307F) as previously described by Wilkinson, R W et al., Clin Cancer Res, 2007; 13(12).

Figure 15:
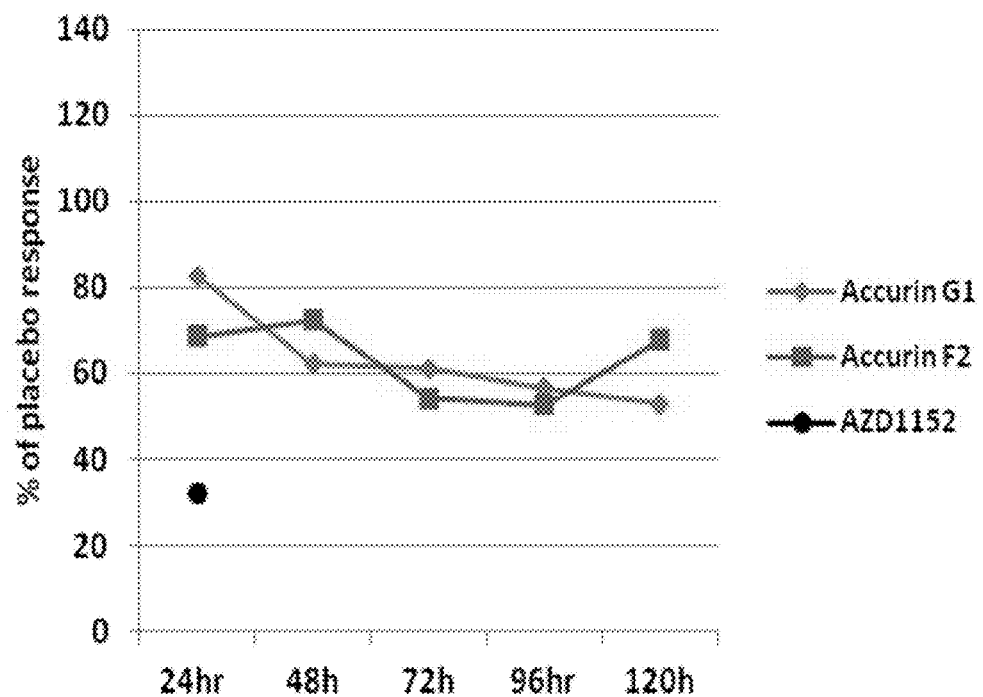
FIG. 15 depicts in vivo activity of AZD1152 and AZD1152 hqpa nanoparticle Formulations G1 and G2.

FIG. 15 shows that the proportion of pHH3-positive cells within the G2/M phase of the cell cycle was maximally suppressed by AZD1152 at 24 hours. Tumours exposed to Formulations G1 or G2 showed less reduction in pHH3 at 24 hrs post single dose compared with animals receiving AZD1152. Maximum reduction in pHH3 activity occurs between 72 and 120 hrs after the $1^{st}$ dose of formulations G1 or G2. These data show that Formulations G1 and G2 suppression pHH3 and hence Aurora kinase B activity over a single dose time course.

Effects of Formulations G1 and G2 on Bone Marrow.

This example shows the effects of the Formulations on the bone marrow.

Rats were injected IV with BIND Placebo (0 mg/kg), or AZD1152 hqpa Formulation G1 or G2 at 25 mg/kg on days 1 and day 3 and sacrificed at the times indicated.

Figure 16:
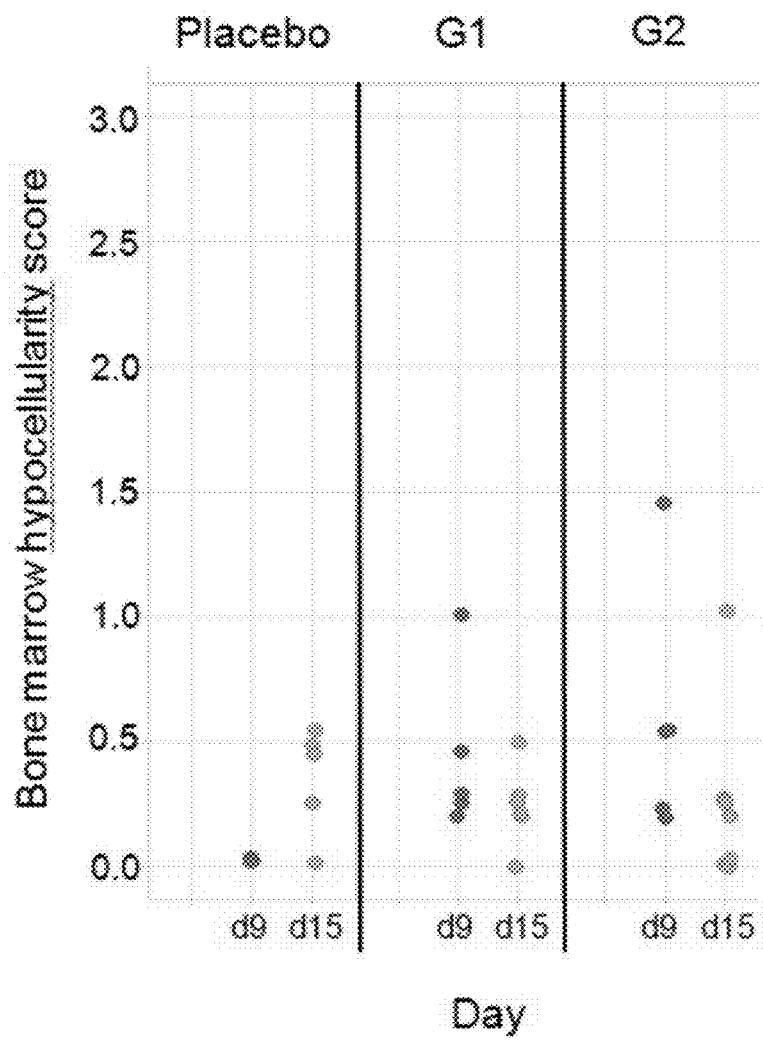
FIG. 16 depicts effects of Formulations G1 and G2 on bone marrow integrity.

Bone marrow samples were extracted from each animal and processed for pathological assessment. Femuro-tibial joints were taken to 10% Buffered Formalin, decalcified using standard procedures, paraffin embedded and stained with haemotoxylin and eosin. Pathological assessment of bone marrow hypo-cellularity was carried out by a pathologist (FIG. 16). Bone marrow integrity was scored by the pathologist. A bone marrow hypocellularity score was generated based on a scoring system of 0-4, with 0 representing no bone marrow effect and 4 representing maximal effect on the bone marrow. The figures show the scores for individual animals in each group of animals at day 5 and 9. The data show that each of the tested nanoparticulate formulations of AZD1152 hqpa show minimal to mild hypocellularity of the bone marrow at day 5 which has returned to similar levels as the BIND placebo by day 9.

U2932 Diffuse Large B Cell Xenograft Efficacy Study

Female scid mice were bred at Charles River. Animals were inoculated in the flank with U2932 human tumour cells, and then randomized onto study when tumours reached approximately 0.25 cm³. AZD1152 was dosed in tris buffer vehicle at the concentration indicated. AZD1152 hqpa nanoparticle formulation G1 was dosed in physiological saline. In the U2932 model in mouse, the nanoparticle formulation G1 demonstrated equivalent efficacy to AZD1152 IV at a total dose of 100 mg/kg and this efficacy was achieved at the lower total dose of only 50 mg/kg showing that lower doses of the nanoparticulate formulation of AZD1152 hqpa are equivalent to an IV formulation of AZD1152.

Figure 17:
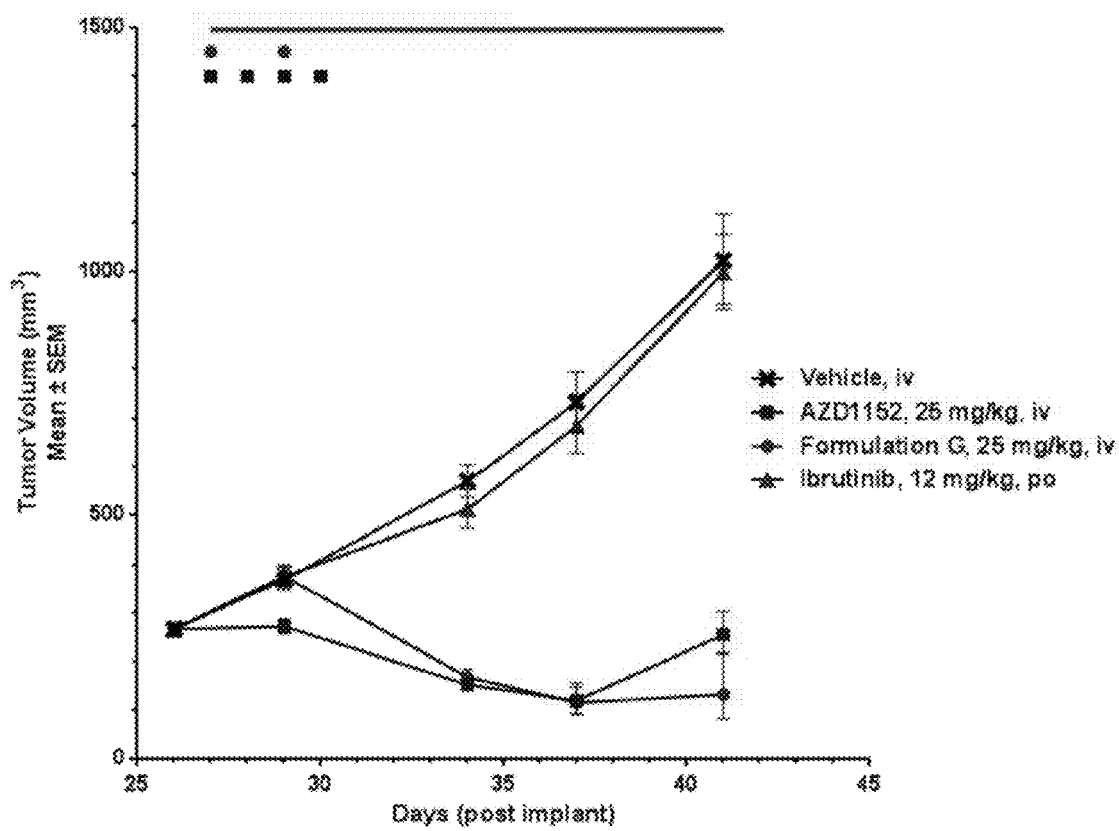
FIG. 17 depicts a comparison between the tumour control from Formulation G1 and that from AZD1152 in mice bearing U2932 tumours.

FIG. 17 shows data from an efficacy study with Formulation G1 in U2932 xenograft in the scid mouse. Mice bearing U2932 tumours were dosed intravenously with AZD1152 at 25 mg/kg daily on days 26-30 post tumour implant (total dose 100 mg/kg), or Formulation G1 25 mg/kg on days 26 and 28 post tumour implant (total dose 50 mg/kg). This data demonstrate that formulation G1 gives equivalent efficacy to AZD1152 at only half the dose.

SC-61 SCLC Patient Derived Explant Efficacy Study

Female nude mice were bred at Harlan. Animals were inoculated in the flank with SC-61 human tumour fragments, and then randomized onto study when tumours reached approximately 0.2 cm³. AZD1152 was dosed in tris buffer vehicle at the concentration indicated. AZD1152 hqpa nanoparticle formulation G1 was dosed in physiological saline. In the SC-61 model in mouse, the nanoparticle formulation G1, at a total dose of 50 mg/kg demonstrated equivalent efficacy to AZD1152 IV at a total dose of 100 mg/kg.

Figure 18:
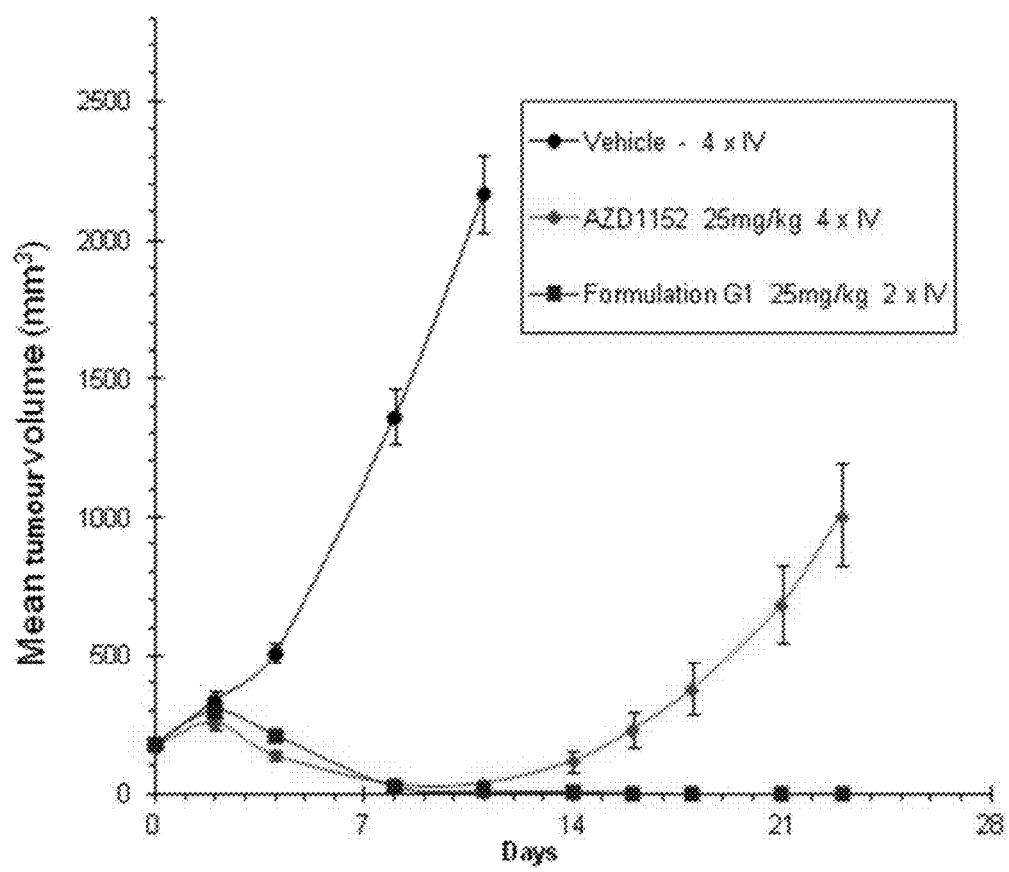
FIG. 18 depicts a comparison between the tumour control from Formulation G1 and that from AZD1152 in mice bearing SC-61 primary tumours.

FIG. 18 shows data from an efficacy study with Formulation G1 in SC-61 patient-derived explant in the nude mouse. Mice bearing SC-61 tumours were dosed intravenously with AZD1152 at 25 mg/kg daily on days 0-3 post randomization (total dose 100 mg/kg), or Formulation G1 25 mg/kg on days 0 and 2 post tumour randomisation (total dose 50 mg/kg).

This data demonstrate that formulation G1, at only half the dose, gives longer tumour control than AZD1152 in this model.

In-Vivo Exposure of Formulations G1 and G2

Figure 19:
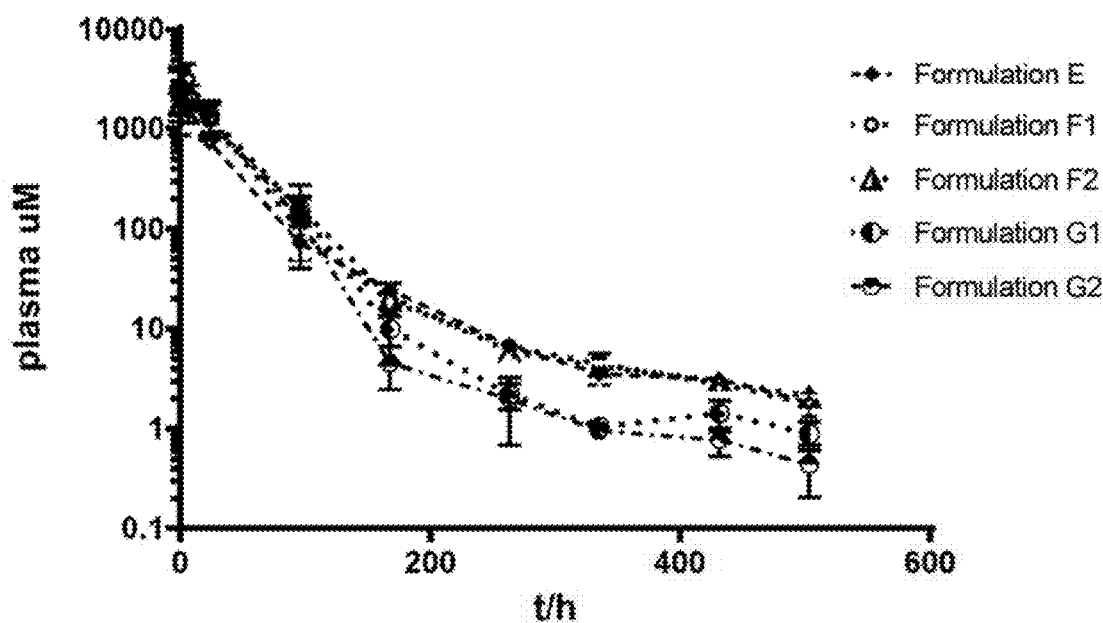
FIGS. 19 and 19a to 19e depict comparative pharmacokinetic profiles for formulations E to G.
Figure 19A:
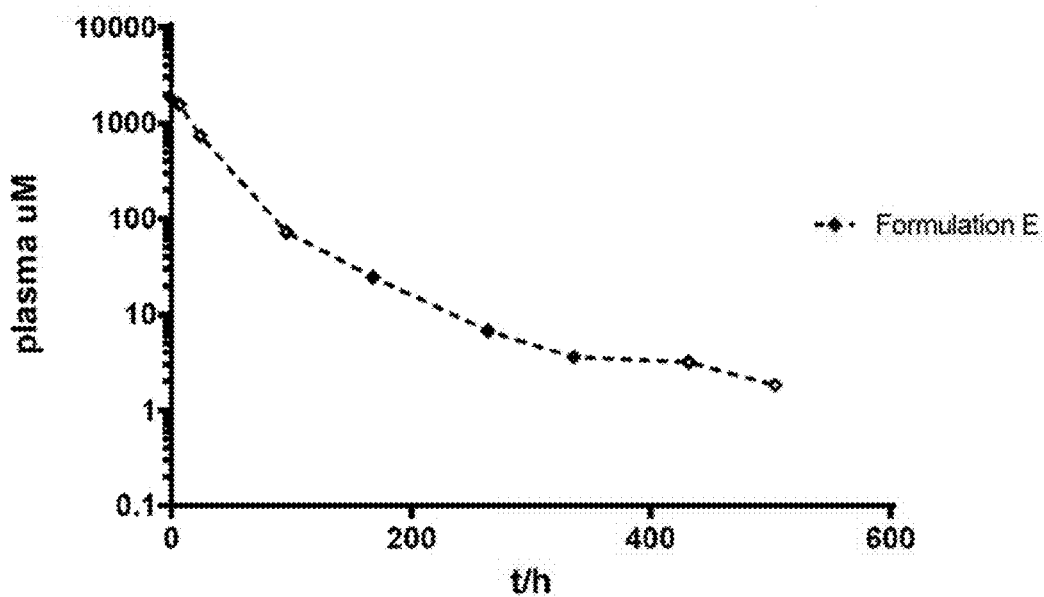
Figure 19B:
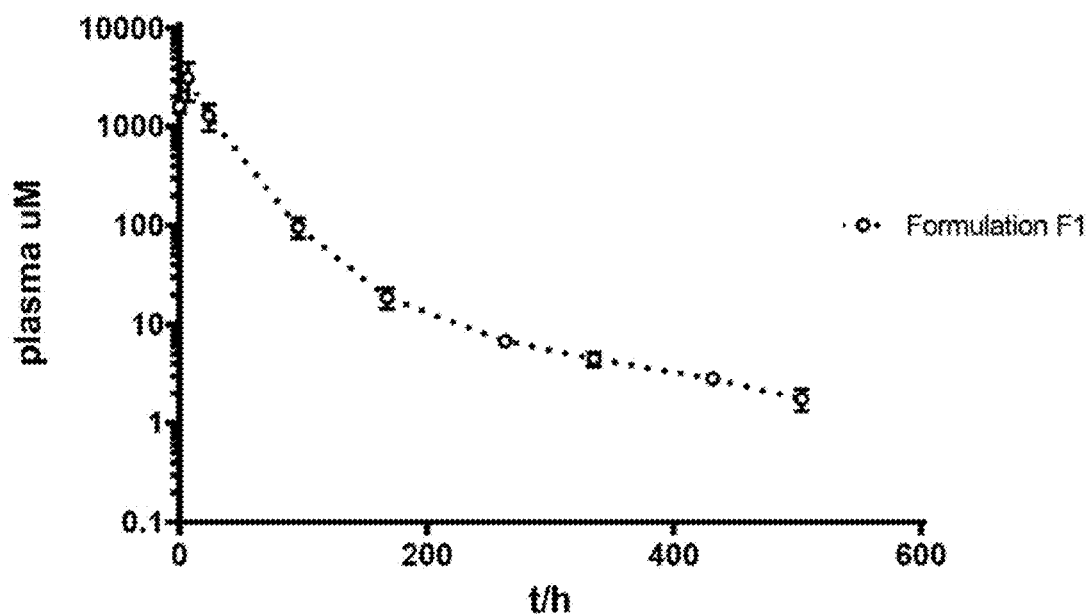
Figure 19C:
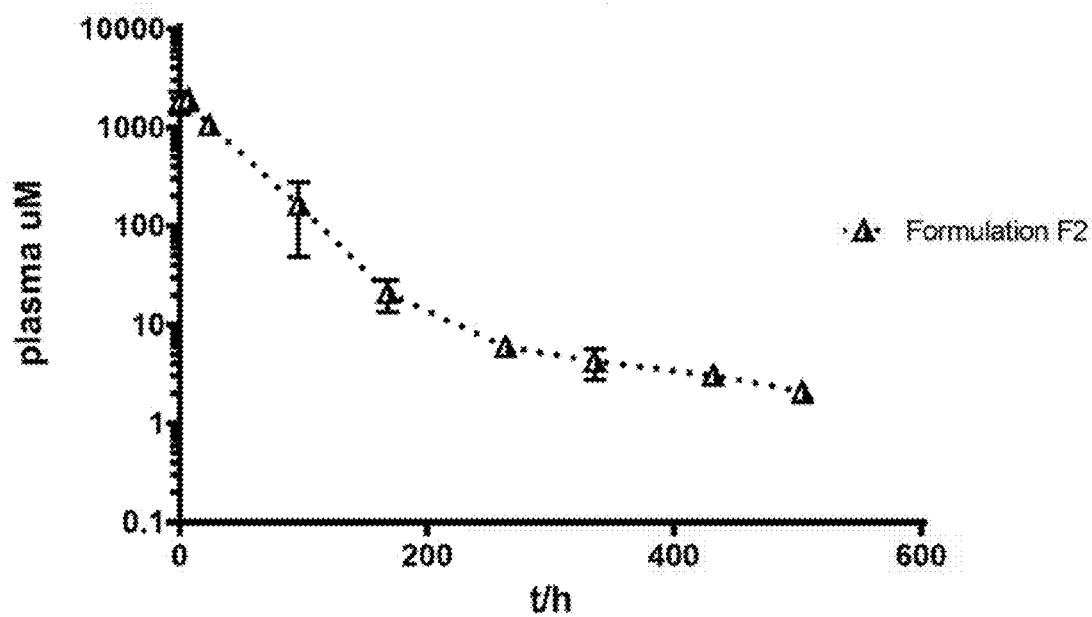
Figure 19D:
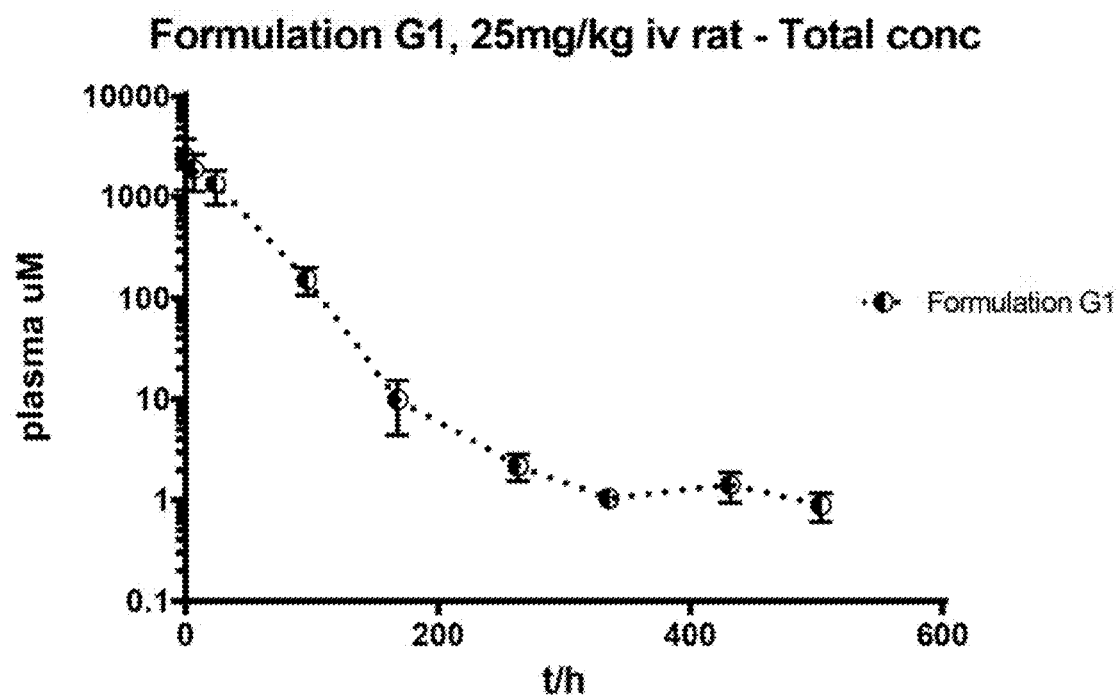
Figure 19E:
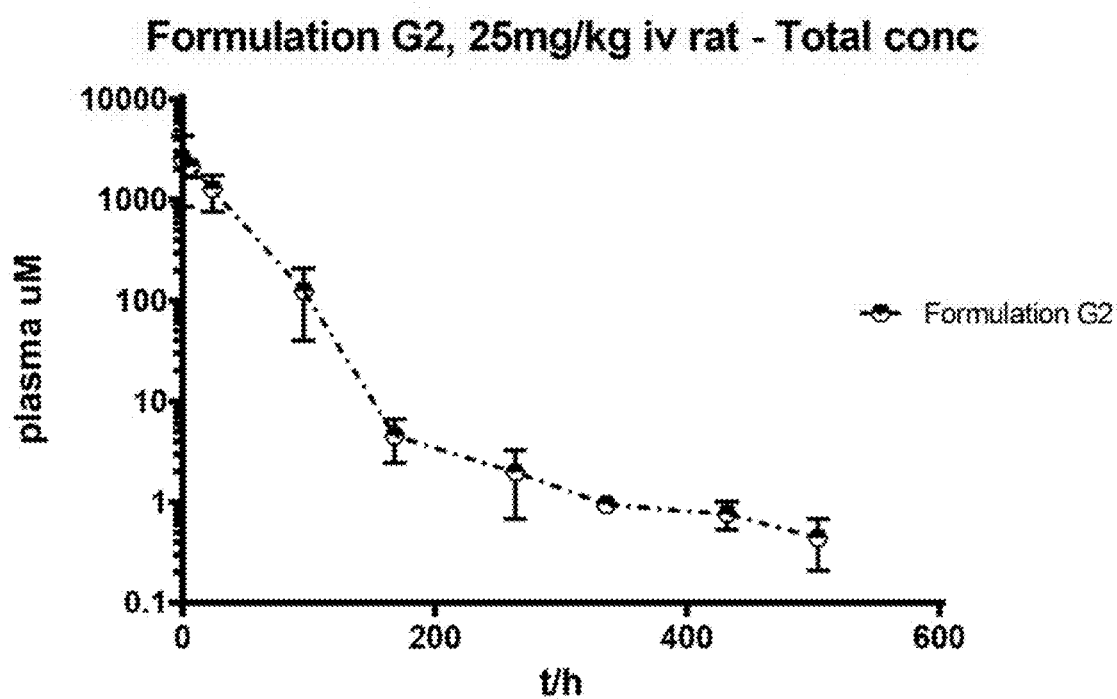

FIG. 19 shows in-vivo exposure data for Formulations G1 and G2, superimposed on those for Formulations E and F from FIG. 10. All data were generated from a single dose of the relevant formulation at 25 mg/kg in rat and analysed by an analogous method to that described in Example 6. FIGS. 19a-19e show each of the individual data lines separately.

Example 10

Suitable HPLC Conditions for Measuring In-Vitro Release

Instrument Parameters

| | |
|---|---|
| Flow rate | 0.300 mL/min |
| Sample loop | 20 μL |
| Injection volume | 5 μL |
| Autosampler Temperature | 5° C. |
| Column Temperature | 30° C. |
| Detector wavelength | 240 nm |
| Sampling rate | 20 points/second |
| Run time | 8 min |

Pump Gradient Program

| Time | Mobile Phase A (%) | Mobile Phase B (%) | Gradient Slope |
|---|---|---|---|
| 0.0 | 85 | 15 | 6 |
| 4.0 | 80 | 20 | 6 |
| 5.0 | 50 | 50 | 6 |
| 6.0 | 15 | 85 | 6 |
| 6.1 | 85 | 15 | 6 |
| 8 | 85 | 15 | 6 |

Mobile Phase-A: 0.10% TFA in water: Fill a 2-L glass media bottle with 2 L purified water. Add 2.0±0.1 mL of TFA and mix.

Mobile Phase-B: 0.08% TFA in acetonitrile: Fill a 2 L glass media bottle with 2 L acetonitrile. Add 1.6±0.1 mL of TFA and mix.

HPLC Column: Waters Acquity CSH C18, 2.1×150 mm, 3 μm (P/N 186005298)

Example 11

Batch data for 3 batches of Formulations G1 containing pamoic acid are shown below. Particle size was measured by dynamic light scattering.

| Lot | AZD1152 hqpa Load (%) | Mean Particle size (nm) | Pamoic: AZD1152 hqpa ratio |
|---|---|---|---|
| A | 17.0 | 87.9 | 0.76 |
| B | 19.9 | 98.4 | 0.60 |
| C | 19.0 | 85.1 | 0.73 |
| Mean | 18.6 | 90.5 | 0.70 |
| Std | 1.5 | 7.0 | 0.09 |
| +3 STD | 23.1 | 111.5 | 0.95 |
| −3 STD | 14.2 | 69.4 | 0.44 |

Figure 20:
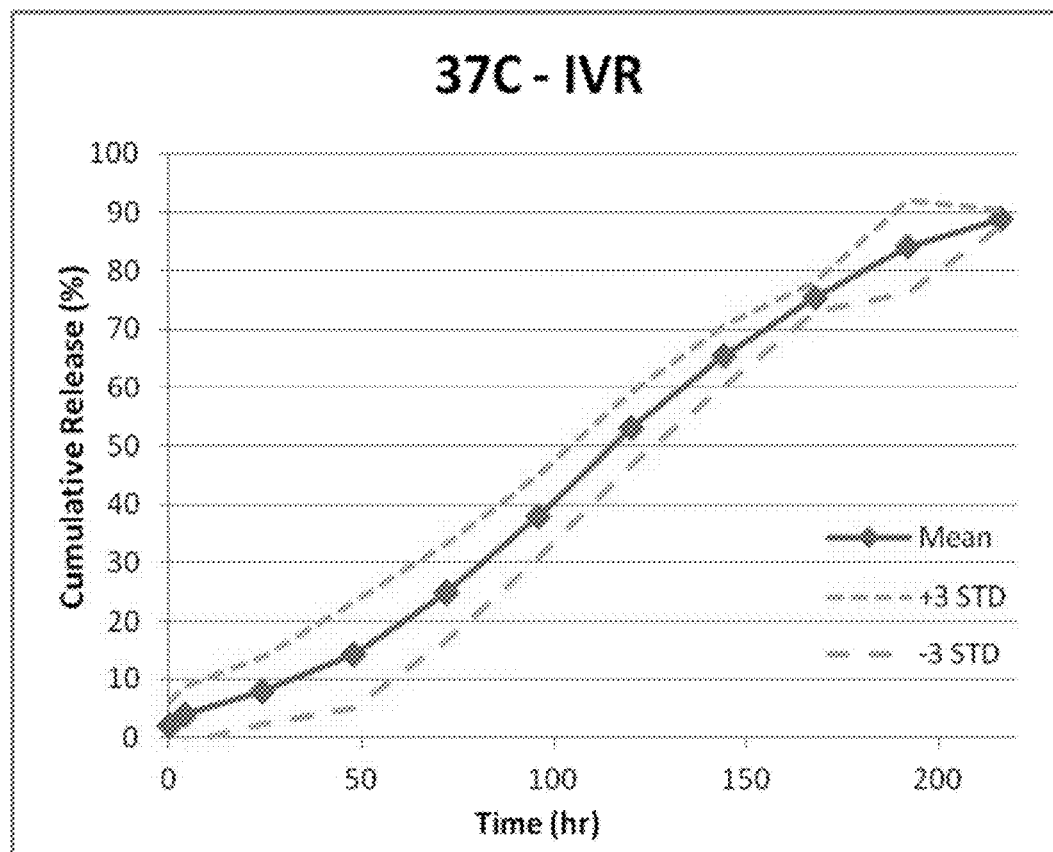
FIG. 20 depicts in-vitro release at 37° C. of Formulation G1 batches shown in Example 11.

In-vitro release profiles at 37° C. for these batches are shown in FIG. 20.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

The invention claimed is:

1. A therapeutic nanoparticle comprising
   about 15 to about 25 weight percent of 2-(3-((7-(3-(ethyl(2-hydroxyethyl)amino)propoxy)quinazolin-4-yl)amino)-1H-pyrazol-5-yl)-N-(3-fluorophenyl)acetamide,
   about 7 to about 15 weight percent of pamoic acid, and
   a diblock poly(lactic) acid-poly(ethylene)glycol copolymer; wherein the diblock poly(lactic) acid-poly(ethylene)glycol copolymer has a poly(lactic acid) block having a number average molecular weight of about 16 kDa and a poly(ethylene)glycol block having a number average molecular weight of about 5 kDa; wherein the poly(ethylene)glycol block comprises about 10 to 30 weight percent of the therapeutic nanoparticle.

2. A pharmaceutically acceptable composition comprising a plurality of therapeutic nanoparticles of claim 1 and one or more pharmaceutically acceptable excipients, diluents and/or carriers.

3. A composition comprising the pharmaceutically acceptable composition as claimed in claim 2 in combination with an anti-tumour agent.

4. A kit of parts comprising:
   a) a lyophilized pharmaceutical composition comprising nanoparticles as claimed in claim 1; and
   b) instructions for use.

5. The therapeutic nanoparticle of claim 1, which has a hydrodynamic diameter of 70-140 nm.

* * * * *